United States Patent
Tang et al.

(10) Patent No.: US 11,634,493 B2
(45) Date of Patent: Apr. 25, 2023

(54) TUMOR IMMUNOTHERAPY TARGET AND APPLICATION THEREOF

(71) Applicant: BEIJING PROTEOME RESEARCH CENTER, Beijing (CN)

(72) Inventors: Li Tang, Beijing (CN); Fuchu He, Beijing (CN); Di Liu, Beijing (CN); Qian Lu, Beijing (CN)

(73) Assignee: BEIJING PROTEOME RESEARCH CENTER, Beijing (CN)

( * ) Notice: Subject to any disclaimer, the term of this patent is extended or adjusted under 35 U.S.C. 154(b) by 799 days.

(21) Appl. No.: 16/346,316

(22) PCT Filed: Nov. 2, 2017

(86) PCT No.: PCT/CN2017/109031
§ 371 (c)(1),
(2) Date: Jul. 15, 2019

(87) PCT Pub. No.: WO2018/082590
PCT Pub. Date: May 11, 2018

(65) Prior Publication Data
US 2021/0163598 A1 Jun. 3, 2021

(30) Foreign Application Priority Data

Nov. 2, 2016 (CN) .......................... 201610952945.2
Nov. 2, 2016 (CN) .......................... 201610953057.2

(51) Int. Cl.
| C07K 14/705 | (2006.01) |
| C07K 19/00 | (2006.01) |
| A61K 38/17 | (2006.01) |
| A61P 35/00 | (2006.01) |
| C07K 16/28 | (2006.01) |
| A61P 35/02 | (2006.01) |
| C12N 15/113 | (2010.01) |
| A61K 39/00 | (2006.01) |

(52) U.S. Cl.
CPC .......... *C07K 16/2827* (2013.01); *A61P 35/02* (2018.01); *C12N 15/113* (2013.01); *A61K 2039/505* (2013.01); *C07K 2317/14* (2013.01); *C07K 2317/76* (2013.01); *C07K 2319/30* (2013.01); *C12N 2310/122* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| 2003/0004124 A1* | 1/2003 | Rothman | ......... C07K 14/43545 |
| | | | 514/44 R |
| 2004/0053307 A1* | 3/2004 | Wood | ............... C07K 14/70503 |
| | | | 435/372 |
| 2007/0077553 A1* | 4/2007 | Bentwich | ............... C12Q 1/703 |
| | | | 435/5 |
| 2014/0322235 A1* | 10/2014 | Olive | ................. C07K 16/2896 |
| | | | 530/389.6 |
| 2018/0147257 A1* | 5/2018 | Corey | ............ A61K 39/001129 |
| 2021/0163598 A1* | 6/2021 | Tang | ....................... A61P 35/02 |

FOREIGN PATENT DOCUMENTS

| CN | 101732715 A | 6/2010 |
| CN | 104906575 A | 9/2015 |
| CN | 105457024 A | 4/2016 |

OTHER PUBLICATIONS

Dominguez-Soto et al. (2007) The DC-SIGN-related lectin LSECtin mediates antigen capture and pathogen binding by human myeloid cells. Blood 109 (12): 5337-5345.*
Xu et al. (2014) LSECtin Expressed on Melanoma Cells Promotes Tumor Progression by Inhibiting Antitumor T-cell Responses. Cancer Res 74 (13): 3418-3428.*
Palakodeti et al. (2012) The Molecular Basis for Modulation of Human Vγ9Vδ2 T Cell Responses by CD277/Butyrophilin-3 (BTN3A)-specific Antibodies. Immunology 287 (39): 32780-32790.*
Messal et al. (2011) Differential role for CD277 as a co-regulator of the immune signal in T and NK cells. Eur. J. Immunol. 41: 3443-3454.*
Arnett et al. (2014) Immune modulation by butyrophilins. Nature Reviews Immunology 14: 559-569.*
UniProt Entry 000478 (1997), 7 pages.*
UniProt Entry 2DTS_A (2012), 3 pages.*
Liu et al. (2019) Cell Research 29(5): 365-378 [reference provided by applicant].*
Sandstrom A., "The Intracellular B30.2 Domain of Butyrophilin 3A1 Binds Phosphoantigens to Mediate Activation of Human Vγ9Vδ2 T Cells", Immunity 40:490-500 (Apr. 17, 2014).
Yamashiro H., "Stimulation of Human Butyrophilin 3 Molecules Results in Negative Regulation of Cellular Immunity", Journal of Leukocyte Biology 88:757-767 (Oct. 2010).
International Search Report dated Feb. 7, 2018 received in International Application No. PCT/CN2017/109031, together with an English-language translation.
Davie S.A. et al., "Effects of FVB/NJ and C57B1/6J Strain Backgrounds on Mammary Tumor Phenotype in Inducible Nitric Oxide Synthase Deficient Mice", Transgenic Res 16:193-201 (2007).

(Continued)

*Primary Examiner* — Ilia I Ouspenski
(74) *Attorney, Agent, or Firm* — Scully, Scott, Murphy & Presser, P.C.

(57) ABSTRACT

The present invention provides a tumor immunotherapy target and use thereof, specifically provides use of the LSECtin expressed by infiltrating tumor-associated macrophage and BTN3A3 expressed by tumor solely or in combination as a target in tumor immunotherapy, and further provides a substance capable of inhibiting the activity of LSECtin expressed by infiltrating tumor-associated macrophage, the activity of BTN3A3 expressed by tumor, or the interaction of the LSECtin with BTN3A3, including RNA molecules, fusion protein BTN3A3-Ig, and monoclonal antibody 5E08, which can be used as an active ingredient to prepare a tumor immunotherapy drug, and is suitable for industrial applications.

2 Claims, 13 Drawing Sheets
Specification includes a Sequence Listing.

(56) References Cited

OTHER PUBLICATIONS

Liu B. et al., "Liver Sinusoidal Endothelial Cell Lectin Inhibits CTL-Dependent Virus Clearance in Mouse Models of Viral Hepatitis", The Journal of Immunology 190:doi:10.4049 (Mar. 13, 2013).
Peedicayil A. et al., "Risk of Ovarian Cancer and Inherited Variants in Relapse-Associated Genes", PLoS One 5(1):e8884 (Jan. 2010).
Tang L. et al., "The DC-SIGN Family Member LSECtin is a Novel Ligand of CD44 on Activated T Cells", European Journal of Immunology 40:1185-1191 (2010).
Tang L. et al., "Liver Sinusoidal Endothelial Cell Lectin, LSECtin, Negatively Regulates Hepatic T-Cell Immune Response", Gastroenterology 137:1498-1508 and Supplementary Material (2009).
Xu F. et al., "LSECtin Expressed on Melanoma Cells Promotes Tumor Progression by Inhibiting Antitumor T-Cell Responses", Cancer Research 74(13):3418-3428 and Supplementary Material (Jul. 1, 2014).
Zhao D. et al., "The Myeloid LSECtin is a DAP12-Coupled Receptor that is Crucial for Inflammatory Response Induced by Ebola Virus Glycoprotein", PLoS Pathog 12(3):e1005487 (Mar. 4, 2016).
Zuo Y. et al., "Novel Roles of Liver Sinusoidal Endothelial Cell Lectin in Colon Carcinoma Cell Adhesion, Migration and In-Vivo Metastasis to the Liver", Gut 62(8):1169-1178 and Supplementary Material (Aug. 2013).

\* cited by examiner (a)

(b)

(c)

(d)

(a)

(b)

(c)

(d)

(e)

(a)
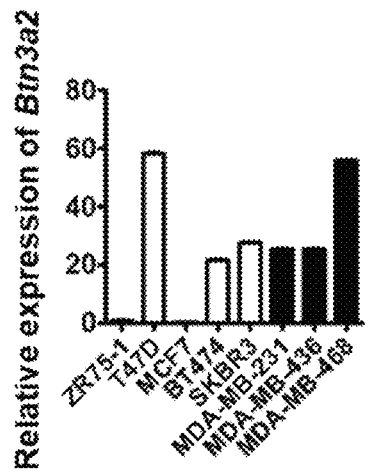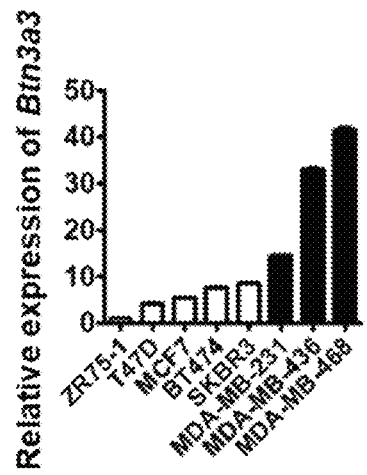
(b)
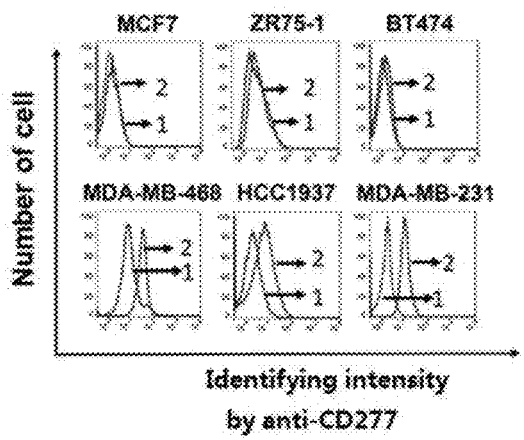
1- Control
2- Experimental group
(c)
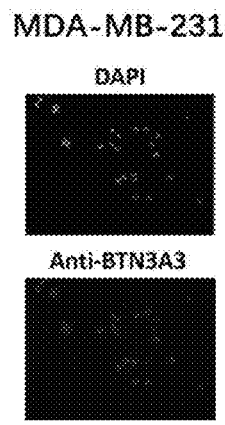
Figures 5a-5c (a)

(b)

(c)

(a)

(b)

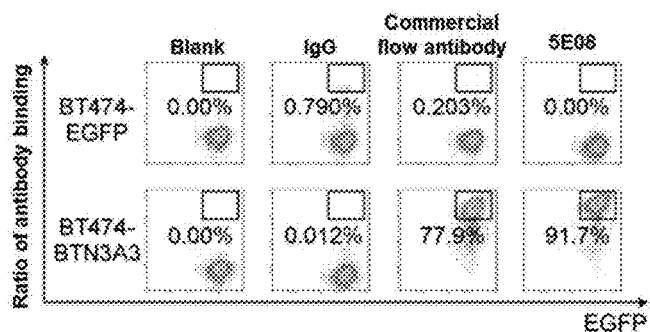
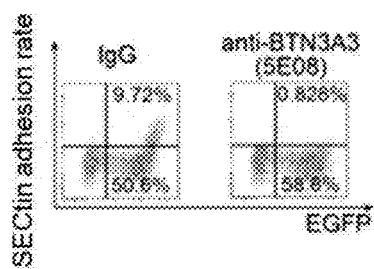
Figure 23　　　　　　　　Figure 24
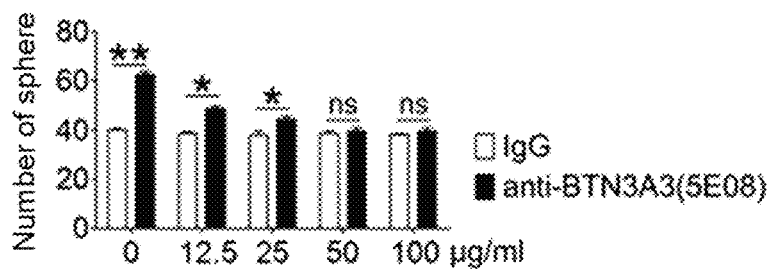
Figure 25
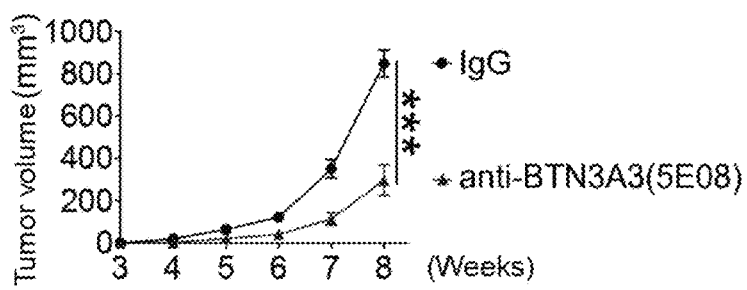
Figure 26
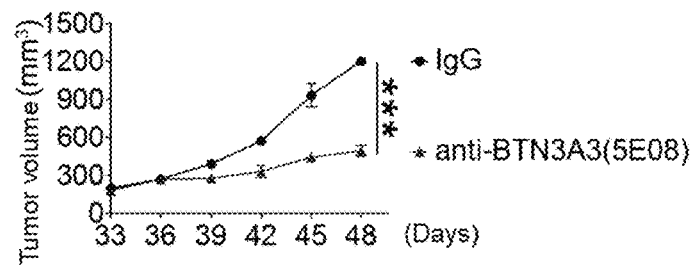
Figure 27

TUMOR IMMUNOTHERAPY TARGET AND APPLICATION THEREOF

FIELD OF THE INVENTION

The invention belongs to the field of biotechnology, and particularly relates to targets of tumor immunotherapy for tumor-associated macrophages.

BACKGROUND OF THE INVENTION

Since the late 1970s, the global incidence of tumor has been on the rise. So far, the treatment of tumor includes surgery, radiotherapy, chemotherapy, Endocrine therapy, targeted therapy, auxiliary treatment of traditional Chinese medicine and so on. Drug resistance and recurrence are the root causes that impede the treatment of tumor. Studies show that the maintenance and advance of the tumor cell sternness are the root causes of drug resistance and recurrence. Therefore, the targeted therapy of tumor cell sternness has become a research hotspot increasingly.

The tumor cell sternness is regulated by gene diversity, epigenetics and tumor microenvironment. Because of the high heterogeneity of the tumor cells, it is difficult to propose effective treatment from the view of the gene diversity or epigenetics. On the contrary, the interaction between immune cells infiltrated by tumor microenvironment and tumor cells can promote and maintain the tumor cell sternness and has become a focus of studies because of its strong application prospects. On the basis of the tumor immunotherapy principles, the targeted drugs to block the interaction between immune cells and tumor cells are hopeful to enhance the immunogenicity of the tumor cells and sensibility to effector cells killing, stimulate and enhance the anti-tumor immune response, and coordinate the immune system of the body, to inhibit tumor growth, metastasis and recurrence applying the immunological principles and methods.

Tumor microenvironment factors can promote the tumor cell sternness to rely on the interaction between cells, and the tumor microenvironment is consisted of stromal infiltrating immune cells and other cells. Blockade of the interaction between these cells and tumor cells is expected to reduce the tumor cell sternness and further inhibit tumor initiation and progression. Among these cells, tumor-associated macrophage, the general name for the macrophage in the tumor microenvironment, is an important component of the infiltrating immune cells in the tumor microenvironment Studies have shown that tumor-associated macrophage can promote tumor progression through many different ways, including inhibition of tumor immune response, promotion of immunotolerant tumor microenvironment formation, and promotion of tumor angiogenesis and so on. In view of the fact that tumor-associated macrophages promote tumor progression, clearing tumor-associated macrophages and promoting the transformation of tumor-associated macrophages into immune activation have become potential methods for tumor treatment.

SUMMARY OF THE INVENTION

The present invention aims to provide an use of LSECtin expressed by infiltrating tumor-associated macrophage together with BTN3A3 expressed by tumor cells as a target in the tumor immunotherapy.

The above-mentioned use is based on the mechanism that LSECtin expressed by infiltrating tumor-associated macrophage can interact with the BTN3A3 expressed on the surface of tumor cells, thereby promoting the sternness of tumor cells and promoting the occurrence and development of tumors. The two targets LSECtin or BTN3A3 can be used to develop or design drugs for tumor immunotherapy.

Here, the above-mentioned tumor is a tumor in which the tumor-associated macrophages express LSECtin and the tumor cells express BTN3A3, including but is not limited to breast cancer, myeloma, liver cancer, gastric cancer, colorectal cancer, lung cancer, giant-cell tumor, renal cancer, laryngo cancer and parotid gland cancer.

The present invention also aims to provide an use of LSECtin expressed by infiltrating tumor-associated macrophage or BTN3A3 expressed by tumor cells as a target solely in the tumor immunotherapy.

The above-mentioned use is based on the characteristics that both the LSECtin expressed by infiltrating tumor-associated macrophage and the BTN3A3 expressed on the surface of tumor cells promote the tumor cell sternness and promote the the occurrence and development of tumors. LSECtin or BTN3A3 can be used as a target to develop or design inhibitors to inhibit the occurrence and development of tumors and obtain drugs for tumor immunotherapy.

The tumor of these uses is anyone of the following tumors: c1) tumor in which infiltrating tumor-associated macrophages express LSECtin; c2) tumor expressing BTN3A2 and/or BTN3A3, and c3) tumor satisfying both c1) and c2). The above-mentioned tumors include, but are not limited to breast cancer, myeloma, liver cancer, gastric cancer, colorectal cancer, lung cancer, giant-cell tumor, renal cancer, laryngo cancer and parotid gland cancer.

As the uses to develop or design drugs, the above-mentioned drugs have at least anyone of the functions described in (1)-(5) below:

(1) treating and/or preventing tumor;
(2) inhibiting the growth of tumor cells;
(3) inhibiting the maintenance or promotion of tumor cell sternness;
(4) inhibiting the expression of the tumor cell sternness-related characteristic molecules; and
(5) inhibiting STAT3 phosphorylation in the tumor cells.

Here, the above-mentioned tumor cell sternness-related characteristic molecules are Oct4, and/or Nanog, and/or Sox; the above-mentioned inhibiting the growth of tumor cells is reflected in reducing the tumor formation rate of tumor cells and/or reducing the volume of tumor.

The present invention also aims to provide substance which inhibits the activity of LSECtin expressed by the infiltrating tumor-associated macrophage, the activity of BTN3A3 expressed by the tumor cells or blocks the interactions between the above-mentioned LSECtin and BTN3A3. These substances include, but are not limited to: RNA molecules that interfere with BTN3A2 or BTN3A3 expression, anti-LSECtin antibody, small molecule inhibitor of LSECtin, LSECtin soluble protein, anti-BTN3A2 antibody, small molecule inhibitor of BTN3A2, BTN3A2 soluble protein, RNA molecules that interfere with BTN3A2 expression, anti-BTN3A3 antibody, small molecule inhibitor of BTN3A3, BTN3A3 soluble protein and RNA molecules that interfere with BTN3A3 expression.

The first kind substance is a RNA molecule that interferes with BTN3A2 and BTN3A3 expression, or a RNA molecule that interferes with BTN3A3 expression, and the subtance is anyone of b1) to b4) described below:

b1) a shRNA molecule shown in SEQ ID NO: 4;

b2) a nucleic acid molecule obtained by deleting or adding or changing one or more nucleotides in SEQ If) NO: 4, and having the same function with SEQ ID NO: 4;

3) a shRNA molecule shown in SEQ ID NO: 5; and b4) a nucleic acid molecule obtained by deleting or adding or changing one or more nucleotides in SEQ ID NO: 5, and having the same function with SEQ ID NO: 5.

The secondary kind substance is fusion protein, which has an activity of inhibiting tumor progression, and can block the interactions between LSECtin and BTN3A3, named BTN3A3-Ig, which is a recombinant protein obtained by ligating human BTN3A3 to human IgG1 through a linker peptide.

The above-mentioned fusion protein BTN3A3-Ig is anyone of the amino acid sequence below:

1) SEQ ID NO: 9 in the Sequence Listing;

2) a protein obtained by substituting, deleting or adding one or more amino acid residues in the amino acid sequence of SEQ ID NO: 9 in the Sequence Listing, with an activity of inhibiting tumor progression;

3) a protein obtained by substituting, deleting or adding amino acid residues in the amino acid sequence of SEQ ID NO: 9 in the Sequence Listing, with an activity of inhibiting tumor progression, and the new protein having at least 80% sequence homology with SEQ ID NO: 9.

The Sequence 9 in the Sequence Listing consists of 489 amino acid residues. The first amino acid from the amino (N) terminus is a start codon, and the 2-15 amino acid from the amino terminus is a signal peptide, the 16-262 amino acid from the amino terminus is human BTN3A3, the 263-266 amino acid from the amino terminus is a linker, and the 267-489 amino acid from the amino terminus is human IgG1.

The present invention also includes the encoding gene BTN3A3-Ig of fusion protein BTN3A3-Ig. The sequence of the gene BTN3A3-Ig encoding the fusion protein BTN3A3-Ig is anyone of the nucleotide sequence below:

1) the DNA sequence of SEQ ID NO: 10;

2) a DNA sequence encoding SEQ ID NO: 9;

3) a nucleotide sequence having one or more base changes with the DNA sequence encoding SEQ ID NO: 9, and having an activity of inhibiting tumor progression;

4) a nucleotide sequence having at least 80% sequence homology with SEQ ID NO: 10, and having an activity of inhibiting tumor progression;

5) a nucleotide sequence hybridizing with the DNA sequence defined by SEQ ID NO: 10 under high stringency conditions.

SEQ ID NO: 10 consisted of 1470 bps. The 1-1470 bp from the 5'-terminus is the encoding sequence, which encodes the protein having the amino acid sequence shown in SEQ ID NO: 9. The 46-786 bp from the 5'-terminus is human BTN3A3-encoding sequence. The 787-798 bp from the 5'-terminus is the linker-encoding sequence. The 799-1470 bp from the 5'-terminus is the human IgG1-encoding sequence.

The present invention also includes the expression vector or the transgenic cell lines or host strains of the fusion gene BTN3A3-Ig.

The present invention also includes the primers to amplify any part of the fusion gene BTN3A3-Ig.

The present invention provides the methods to prepare the fusion protein BTN3A3-Ig, including the following steps:

1) Constructing recombinant expression vector: ligating the fusion gene BTN3A3-Ig into an expression vector to obtain a recombinant expression vector containing the fusion gene BTN3A3-Ig;

2) Expressing fusion protein BTN3A3-Ig: transforming or transfecting the recombinant expression vector containing the fusion gene BTN3A3-Ig (pIRES2-EGFP-BTN3A3-Ig) into host cell and progeny cell thereof to obtain recombinant host cell, and culturing the recombinant host cell to make the fusion gene BTN3A3-Ig express, to obtain recombinant expression protein.

3) Purification: purifing the recombinant expression protein to obtain the fusion protein BTN3A3-Ig.

The fusion gene BTN3A3-Ig in the Step 1) is ligated into the sequence between Nhe I and Sal I of the pIRES2-EGFP vector to obtain the recombinant expression vector, named pIRES2-EGFP-BTN3A3-Ig.

The host cell in the Step 2) is a cell which are capable of expressing heterologous genes, including 293T cell, 293 cell or CHO-S cell; the medium to culture recombinant host cell containing the fusion gene BTN3A3-Ig in the Step 2) is a medium suitable for the host cell growth, including serum-free medium M293TI, M2931I, CD CHO or CD OptiCHO™; preferably the serum-free medium M293TI; the cell culture condition of the recombinant host cell containing the fusion gene BTN3A3-Ig in the Step 2) is a culture condition suitable for the host cell, i.e. culturing at 36.5-37.5° C. for 24-120 hours; preferably culturing at 37° C. for 96 hours.

Protein G Sepharose column, Protein A/G Sepharose column or Protein A Sepharose column can be used to purify the recombinant expression protein in the Step 3); preferably Protein G Sepharose column. The method to purify is as follow: adding equilibrium buffer (20 mM PBS, 150 mM NaCl, pH 8.0) into the culture supernatant of the cells (the recombinant host cell containing the fusion gene BTN3A3-Ig) to the pH 8.0; adding the mixed culture supernatant into the Protein G Sepharose equilibrated by the equilibrium buffer; washing the column with the equilibrium buffer until no hybridprotein is detected in the effluent; eluting the column with elution buffer (0.1M glycine, pH 3.0); collecting effluent and neutralizing by neutralizing buffer (1M Tris HCl, pH 9.0). After dialysis by pH 7.2 0.01M PBS with 72 hours, the fusion protein BTN3A3-Ig is obtained.

The fusion protein BTN 3A3-Ig provided by the present invention can be prepared into pharmaceutical composition by combining with pharmaceutical carrier which is pharmaceutically acceptable and suitable for administration. The suitable pharmaceutical carriers are familiar for those skilled in the art, including but are not limited to the normal saline, phosphate buffer, water, liposome, and Nanometer carrier. The pharmaceutical carriers containing the fusion protein BTN3A3-Ig can be prepared by the conventional method.

The pharmaceutical composition containing the fusion protein BTN3A3-Ig provided by the present invention can be administered at an effective dose into human or other mammals through various common ways. The ways to administer include, but are not limited to intravenous injection (iv). intravenous drip (infusion), intramuscular injection (im), subcutaneous injection (sc), and oral (po). Different ways to administer can be choosed for different diseases.

The administration dose of the fusion protein BTN3A3-Ig is about 0.5-2.5 μg/g based on the mouse models in the present invention and the course of the treatment is about 15-30 days. The administration dose and the course of the treatment can be adjusted according to the actual situation.

The third kind substance is the monoclonal antibody having an activity of inhibiting tumor progression, which can block the interactions between LSECtin and BTN3A3.

The heavy chain variable region of the monoclonal antibody is the polypeptide as shown in SEQ ID NO: 13, a polypeptide obtained by substituting, deleting or adding one to ten amino acid residues in the amino acid sequence of SEQ ID NO: 13 and specific for binding to human BTN3A3, or a polypeptide having at least 80% sequence homology with SEQ ID NO: 13 and specific for binding to human BTN3A3. The light chain variable region of the monoclonal antibody is the polypeptide as shown in SEQ ID NO: 14, a polypeptide obtained by substituting, deleting or adding one to ten amino acid residues in the amino acid sequence of SEQ ID NO: 14 and specific for binding to human BTN3A3, or a polypeptide having at least 80% sequence homology with SEQ ID NO: 14 and specific for binding to human BTN3A3.

SEQ ID NO: 13 is consisted of 141 amino acid residues. SEQ ID NO: 14 is consisted of 130 amino acid residues.

The encoding sequence of the heavy chain variable region of the monoclonal antibody is anyone of the following sequences: a DNA sequence having SEQ ID NO: 15, a DNA sequence encoding SEQ ID NO: 13, a sequence having one or more base changes with the DNA sequence encoding SEQ ID NO: 13, a sequence having at least 80% sequence homology with SEQ ID NO: 15, and a sequence which hybridizes to the DNA sequence defined by SEQ ID NO: 15 under high stringency conditions.

The encoding sequence of the light chain variable region of the monoclonal antibody is anyone of the following sequences: a DNA sequence having SEQ ID NO: 16, a DNA sequence encoding SEQ ID NO: 14, a sequence having one or more base changes with the DNA sequence encoding SEQ ID NO: 14, a sequence having at least 80% sequence homology with SEQ ID NO: 16, and a sequence which hybridizes to DNA sequence defined by SEQ ID NO: 16 under high stringency conditions.

The high stringency conditions are hybridizing and washing of the membrane in a solution of 0.1×SSPE (or 0.1× SSC), 0.1% SDS at 65° C.

SEQ ID NO: 15 is consisted of 423 bps, encoding the protein with the amino acid sequence of SEQ ID NO: 13. SEQ ID NO: 16 is consisted of 390 bps, encoding the protein having the amino acid sequence of SEQ ID NO: 14.

The present invention also includes the expression vector, the transgenic cell lines or host cells having the gene 5E08.

The present invention also includes the primers to amplify any part of the gene 5E08.

The present invention also includes the hybridoma cell line that can secrete monoclonal antibody to block the interactions between LSECtin and BTN3A3, which is prepared as follows: immunizing mice with immunogen which is fusion protein (named BTN3A3-mIg) obtained by ligating human BTN3A3 with mouse IgG2a through a linker peptide and obtaining the hybridoma cell line which can continuously and stably secrete monoclonal antibody with the activity to inhibit tumor progression.

The sequence of the fusion protein BTN3A3-mIg is anyone of the following amino acid sequences: 1) SEQ ID NO: 11; 2) a sequence obtained by substituting, deleting or adding one or more amino acid residues in the amino acid sequence of SEQ ID NO: 11 and having anti-BTN3A3 immunogenicity; 3) a sequence obtained by substituting, deleting or adding amino acid residues in the amino acid sequence of SEQ ID NO: 11 and having anti-BTN3A3 immunogenicity, and the new protein having at least 80% sequence homology with SEQ ID NO: 11.

The amino acid sequence of SEQ ID NO: 11 is consisted of 499 amino acid residues. The first amino acid from the N-terminus is start codon, the 2-15 amino acid from the N-terminus is the signal peptide, the 16-262 amino acid from the N-terminus is human BTN3A3, the 263-266 amino acid from the N-terminus is a linker, the 267-498 amino acid from the N-terminus is mouse IgG2a, and the 499 amino acid from the N-terminus is termination codon.

The present invention also includes the coded gene of the fusion protein BTN3A3-mIg, named BTN3A3-mIg.

The sequence coding the fusion protein BTN3A3-mIg is the anyone of the following nucleotide sequences: 1) the DNA sequence of SEQ ID NO: 12; 2) a DNA sequence coding SEQ ID NO: 11; 3) a nucleotide sequence having one or more base changes with the DNA sequence coding SEQ ID NO: 11 and having anti-BTN3A3 immunogenicity; 4) a nucleotide sequence having at least 80% sequence homology with SEQ ID NO: 12, and having anti-BTN3A3 immunogenicity; 5) a nucleotide sequence which hybridizes to DNA sequence defined by SEQ ID NO: 12 under high stringency conditions.

The high stringency conditions were washing the membrane in a solution of 0.1×SSPE (or 0.1×SSC), 0.1% SD S at 65° C. after hybridizing.

SEQ ID NO: 12 is consisted of 1497 bps. The 1-1497 bp from the 5'-terminus is the encoding sequence encoding the protein having the amino acid sequence shown in SEQ ID NO: 11. The 1-3 bp from the 5'-terminus is start codon. The 4-45 bp from the 5'-terminus is signal peptide. The 46-786 bp from the 5'-terminus is human BTN3A3-encoding sequence. The 787-798 bp from the 5'-terminus is the linker. The 799-1494 bp from the 5'-terminus is mouse IgG2a-encoding sequence, The 1495-1497 bp from the N-terminus is termination codon.

The present invention also includes the expression vector or the transgenic cell lines or host cells containing the fusion gene BTN3A3-mIg.

The present invention also includes the primers to amplify any part of the fusion gene BTN3A3-mIg.

The present invention also provides the methods to express the fusion protein BTN3A3-mIg, including the following steps: 1) Constructing recombinant expression vector: ligating the fusion gene BTN3A3-mIg into an expression vector to obtain a recombinant expression vector containing the fusion gene BTN3A3-mIg; 2) Expressing fusion protein BTN3A3-mIg: transforming or transfecting the recombinant expression vector containing the fusion gene BTN3A3-mIg into host cells and their progeny cells to obtain recombinant host cells, and culturing the recombinant host cells to make the fusion gene BTN3A3-mIg express, to obtain recombinant expression protein. 3) Purification: purifing the recombinant expression protein to obtain the fusion protein BTN3A3-mIg.

The hybridoma cell line, named anti-P3(5E08), that can continuously and stably secrete monoclonal antibody having the activity to inhibit tumor progression, is prepared by the method as follows: immunizing the mice with the fusion protein BTN3A3-mIg as immunogen. The hybridoma cell line anti-P3(5E08) has been preserved in the China General Microbiological Culture Collection Center (CGMCC) on Sep. 26, 2017. The correspondence address of CGMCC is as follows: NO.3, yard 1, West Beichen Road, Chaoyang District, Beijing 100101, China, and the perservation number is CGMCC No.14723.

The present invention also includes the monoclonal antibody named 5E08, which comes from mice (*Mus musculus*), secreted from the hybridoma cell line anti-P3 (5E08) that can block the interactions between LSECtin and BTN3A3 and has the activity to inhibit tumor progression.

The present invention provides the methods to obtain the hybridoma cell line that secrets the monoclonal antibody to block the interactions between LSECtin and BTN3A3, including the following steps: 1) Immunizing animal with fusion protein BTN3A3-mIg as immunogen; 2) Separating splenocytes from the immunized animal and fusing that with myeloma cells to obtain hybridoma cells; 3) Screening the hybridoma cells to obtain the hybridoma cell line anti-P3 (5E08).

In the method to obtain the the hybridoma cell line anti-P3 (5E08), the concentration of the fusion protein BTN3A3-mIg in the Step 1) is about 100-400 µg/ml and the priority selection is 400 µg/ml. The animals to be immunized include mouse, rat, rabbit, goat, sheep, pig, donkey, horse and other mammals and the priority selection is mouse.

In the Step 2), the splenocytes are isolated and prepared as a single cell suspension, when the serum antibody level of the immunized animal reaches a peak. If necessary, the splenocyte can be screened using ELISA methodand fused with myeloma cells (preferably mouse myeloma cells SP2/0) under the induction of a suitable fusion agent (such as polyethylene glycol) to form a hybridoma, The Step 3) can be cultured in a selective medium (such as HAT medium) to screen the fused hybridoma cells, and the positive resistant cell lines can be further identified by flow cytometric analysis, Western blots, immuno-precipitation and other methods.

On the basis of the above steps, the methods to obtain the monoclonal antibody 5E08 in the present invention also include the following steps:

4) The monoclonal antibody 5E08 can be collected and purified from the culture fluid or animal ascites of the hybridoma cell line anti-P3 (5E08).

In the Step 4), the hybridoma cell line anti-P3 (5E08) secreting the specificmonoclonal antibody 5E08 having the activity to inhibit tumor progression can be cultured in vitro (such as tissue culture flasks or porous fiber reactors) or in vivo (mouse ascites). The monoclonal antibody 5E08 can be collected and purified from the cell culture fluid or mouse ascites.

Or, the monoclonal antibody 5E08 having an activity of inhibiting tumor progression can be obtained by the following method: constructing the expression of the monoclonal antibody 5E08 using the above-mentioned amino acid sequence or DNA sequence of the heavy chain variable region and light chain variable region of the monoclonal antibody 5E08 and obtaining the 5E08 through conventional protein expression method.

The present invention also aims to provide an use of the above-mentioned RNA molecules, fusion protein BTN3A3-Ig, fusion gene BTN3A3-mIg, expression vector of fusion gene BTN3A3-Ig, transgenic cell lines or host cells, monoclonal antibody 5E08, immunogen (fusion protein BTN3A3-mIg) and its encoding gene BTN3A3-mIg in the preparation of a product having at least one of the following functions described in (b1)-(b5): (b1) treating tumor and/or preventing tumor; (b2) inhibiting tumor progression; (b3) inhibiting the maintenance or advance of tumor cell sternness; (b4) inhibiting the expression of the tumor cell sternness-associated characteristic molecules; and (b5) inhibiting STAB phosphorylation in the tumor cells. The tumor is a tumor in which the tumor-associated macrophage expresses LSECtin and the tumor cell expresses BTN3A3, including but is not limited to breast cancer, myeloma, liver cancer, gastric cancer, colorectal cancer, lung cancer, giant-cell tumor, renal cancer, laryngo cancer and parotid gland cancer.

The present invention proposes an use of infiltrating tumor-associated macrophage-expressed. LSECtin and tumor cell-expressed. BTN3A3 can be used as a target solely or in combination in the tumor immunotherapy. The present invention further proposes a substance to inhibit the activity of LSECtin expressed by infiltrating tumor-associated macrophage or to inhibit the activity of BTN3A3 expressed by tumor cell, or a substance to block the interactions between LSECtin and BTN3A3, including RNA molecule, fusion protein BTN3A3-Ig, monoclonal antibody 5E08, which can be used to prepare tumor immunotherapeutic drugs as active ingredient. Experiments have shown that LSECtin, BTN3A2 and BNT3A3 promote tumor progression by promoting the maintenance of tumor cell sternness, which is embodied in promoting tumor cell sphere-formation, expression of sternness transcription factors, and promotion of tumor progression in mouse tumor models; inhibition of the interaction between LSECtin and BTN3A2 or LSECtin and BTN3A3 can effectively slow down the tumor progression, which is embodied in reducing tumor incidence and slowing tumor volume growth. Blocking experiments also have shown that the fusion protein BTN3A3-Ig has binding activity to LSECtin protein, and the fusion protein BTN3A3-Ig can block the interaction between LSECtin and BTN3A3 expressed on cell surface: The fusion protein BTN3A3-Ig can block the promotion of the tumor cells sternness conducted by LSECtin, inhibit tumor progression, and inhibit tumor progression dependent on LSECtin. Experiments also have shown that the hybridoma cell line anti-P3 (5E08) CGMCC No.14723 can secrete monoclonal antibody 5E08, which has binding activity to BTN3A3 protein, and monoclonal antibody 5E08 can block the interaction between LSECtin and BTN3A3, block LSECtin to promote the tumor cells sternness, and monoclonal antibody 5E08 can inhibit tumor growth. The present invention provides new ideas for tumor immunotherapy and has broad use prospects.

DRAWINGS

FIG. 1 shows that LSECtin promotes tumor initiation in Example 1, wherein:

FIG. 1(*a*) is the detection result curves of tumor volume in spontaneous breast cancer mouse models, showing the comparison of the mouse mammy tumor volume of LSECtin$^{+/+}$PyMT mice with LSECtin$^{-/-}$PyMT mice;

FIG. 1(*b*) is the detection result curves of the number of tumor foci in spontaneous breast cancer mouse models, showing the comparison of the number of breast cancer tumor foci between each LSECtin$^{+/+}$PyMT mouse and each LSECtin$^{-/-}$PyMT mouse in the MMTV-PyMT spontaneous breast cancer model;

FIG. 1(*c*) is a detection result bar chart of the number of lung tumor metastasis foci in spontaneous breast cancer mouse models, showing the comparison of the number of lung tumor metastasis foci between each LSECtin$^{+/+}$PyMT mouse and each LSECtin$^{-/-}$PyMT muse in the MMTV-PyMT spontaneous breast cancer models;

FIG. 1(*d*) is the detection result curves of tumor volume in human breast cancer xenografts in nude mice showing the comparison of the tumor growth between LSECtin$^{+/+}$ Nude$^{-/-}$ mice and LSECtin $^{-/-}$Nude$^{-/-}$ mice.

FIG. 2 shows the detection of LSECtin expression levels in the tumor microenvironment in Example 2, whernin:

FIG. 3 shows that the clinical sample tumor cells express BTN3A3 in Example 4, wherein:

FIG. 4 shows that various tumor cell lines express BTN3A3 in Example 5, wherein:

FIG. 5 shows that BTN3., h. or BTN3A3 expresson the breast cancer cells in Example 6, wherein:

FIG. 5(a) is a histogram of qPCR detection results of BTN3A2 and BTN3A3, showing that breast cancer cell lines express BTN3A2 and BTN3A3, FIG. 5(b) is a peak diagram of BTN3A expression level in breast cancer cell lines by flow cytometric analysis, showing that BTN3A expresses on the surface of the breast cancer cells.

FIG. 5(c) is immunofluorescence staining of cells, showing the localization of BTN3A3 is on the surface membrane of breast cancer cells.

FIG. 6 shows that BTN3A3 expressed by tumor cells promotes tumor formation in Example 7, wherein:

FIG. 7 is the adhesion scatter diagram of recombinant protein LSECtin and BTN3A3 expressed by tumor cell by the flow cytometric analysis, showing direct and specific interaction exist between human or murine LSECtin and BTN3A3, wherein:

FIG. 8 shows LSECtin promotes tumor cell sternness by interacting with tumor cell-expressed BTN3A3 in Example 9, wherein:

Figure 8A:
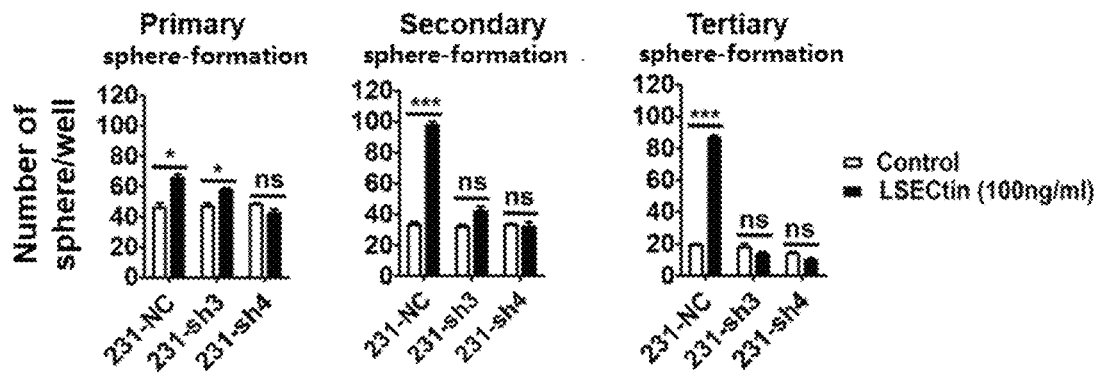
Figure 8B:
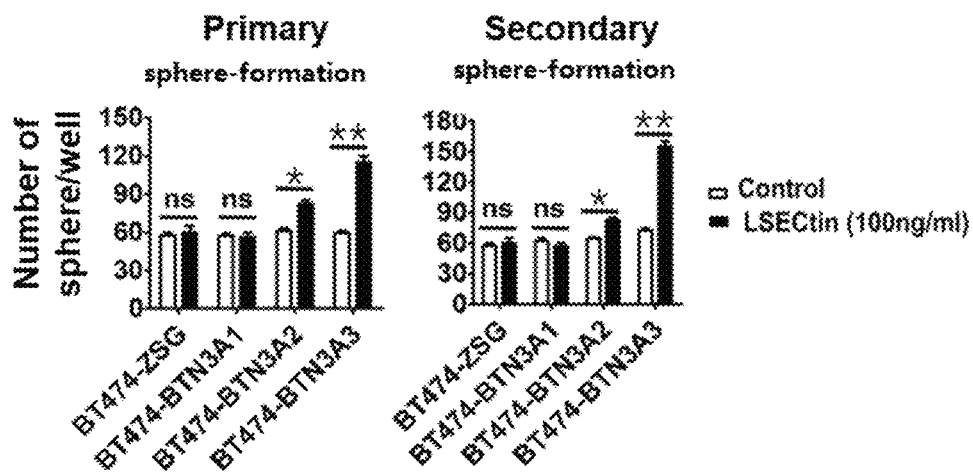

FIG. 8(a) and FIG. 8(b) are histograms of the sphere numbers, showing the ability of LSECtin/BTN3 A3 to promote sphere-formation of MDA-IAMB-231 tumor cell.

Figure 8C:
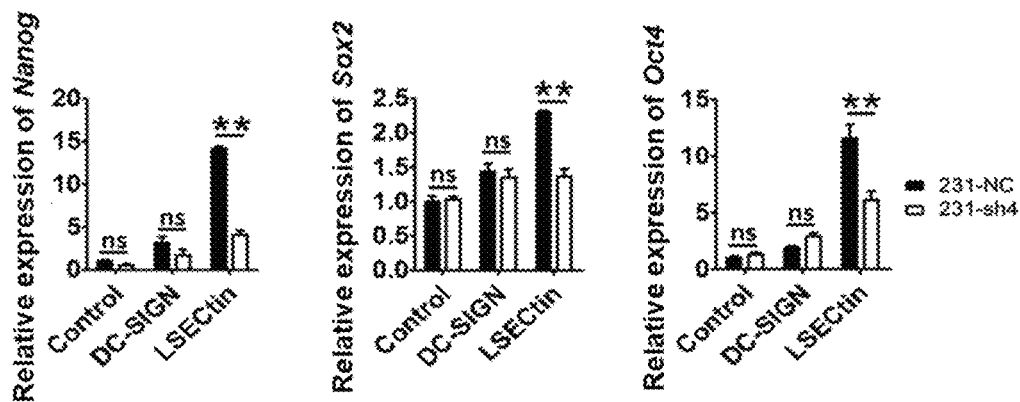

FIG. 8(c) is a histogram of OCR detection of sternness transcription factor expression levels, showing the interaction between LSECtin and BTN3A3 promotes upregulation of tumor cell sternness transcription factor.

Figure 9A:
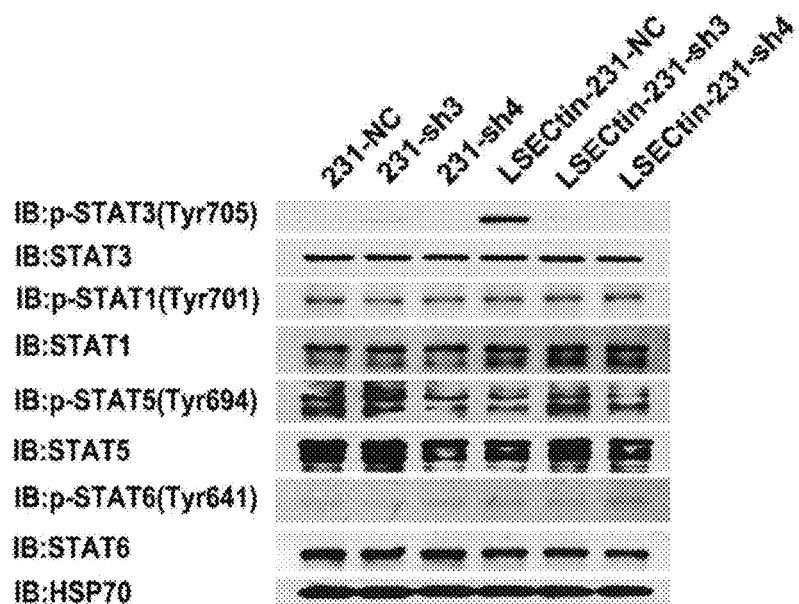

FIG. 9 shows the result that the interaction between LSECtin and tumor cell-expressed BTN3A3 promotes STAT3 phosphorylation in tumor cell and promotes maintenance of tumor cell sternness in Example 10, wherein:

FIG. 9(a) is Western blot results showing that LSECtin-BTN3A3 interactions promote STAT3 phosphorylation of tumor cell, indicating no activation of other STATS.

Figure 9B:
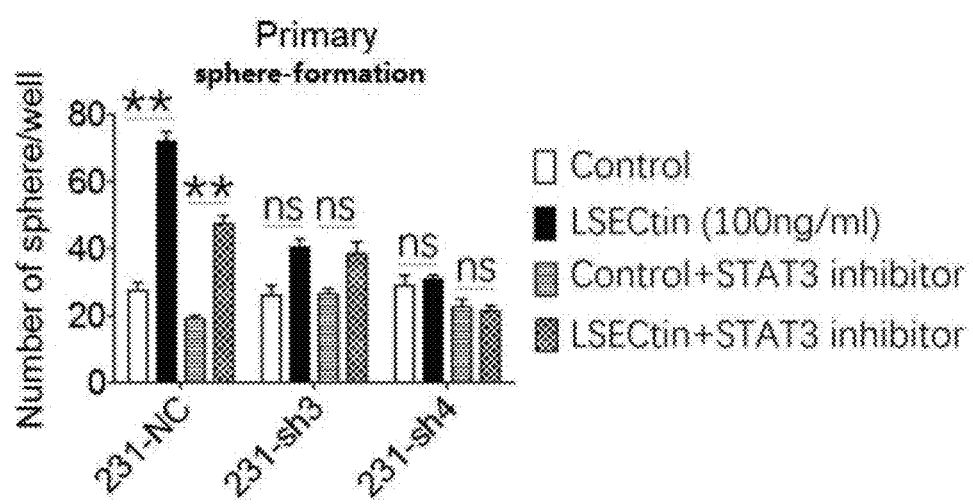

FIG. 9(b) is a histogram of the number of spheres in which LSECtin/BTN3A3 promotes tumor cell sphere-formation, indicating that STAT3 inhibitors can block LSECtin/BTN3A3 to promote tumor cell sphere-formation.

Figure 10:
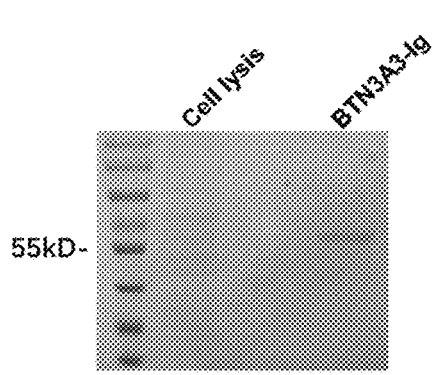

FIG. 10 is Coomassie bright blue staining results of recombinantly expressed fusion protein BTN3A3-11g.

Figure 11:
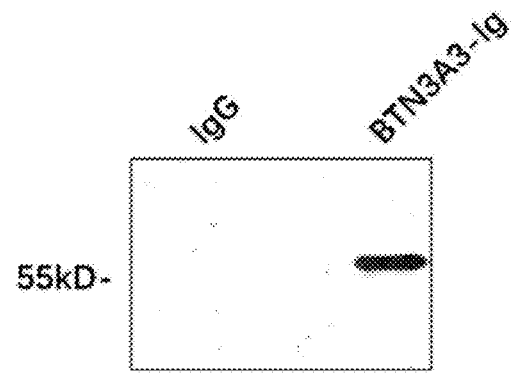

FIG. 11 is Western blot results of recombinantly expressed fusion protein BTN3A3-Ig.

Figure 12:
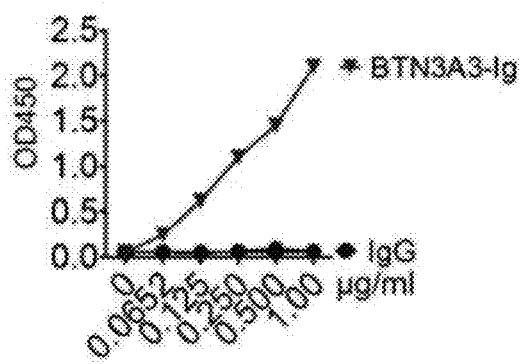

FIG. 12 is Elisa detection result curve of the binding activity of the fusion protein BTN3A3-Ig to the LSECtin protein.

Figure 13:
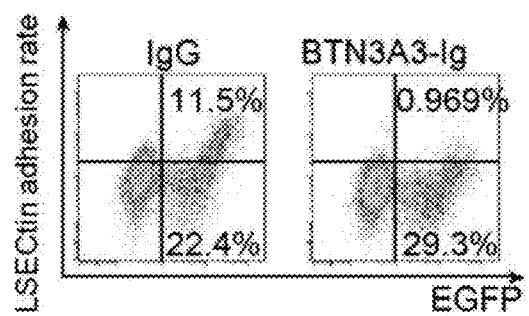
Figure 14:
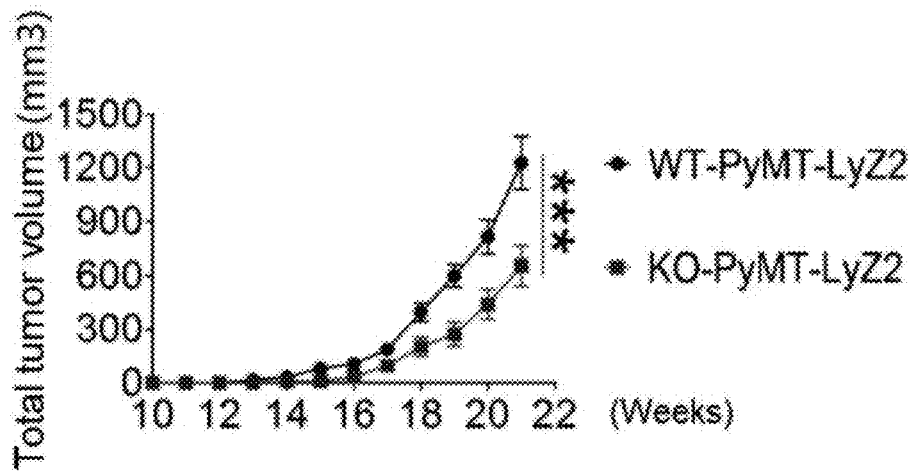
Figure 15:
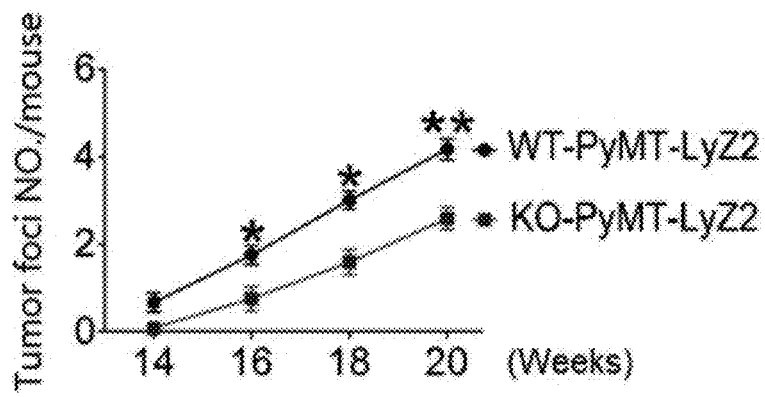

FIG. 13 is a scatter diagram of adhesion assay of the fusion protein BTN3A3-Ig blocking the interaction between the LSECtin protein and the membrane form BTN3A3, FIG. 14 is the detection curve of tumor volume of macrophage-specific LSECtin-knockout spontaneous breast cancer mouse model FIG. 15 is the detection curve of the tumor foci in macrophage-specific LSECtin-knockout spontaneous breast cancer mouse model.

Figure 16:
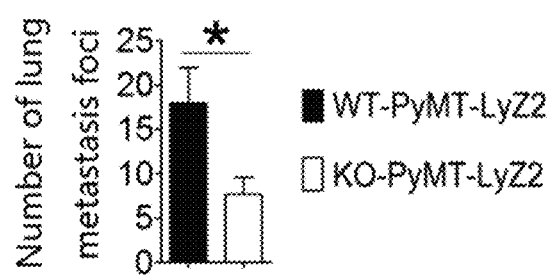

FIG. 16 is the detection histogram of the number of lung tumor metastasis foci in macrophage-specific LSECtin-knockout spontaneous breast cancer mouse model.

Figure 17:
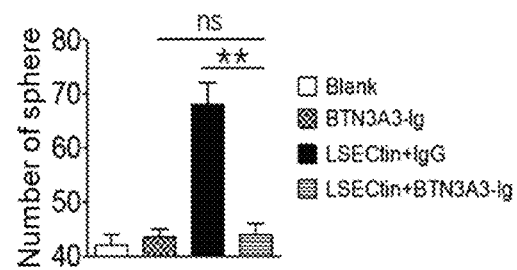

FIG. 17 is a histogram of detection result, showing that the fusion protein BTN3A3-Ig block LSECtin to promote tumor cell sternness.

Figure 18:
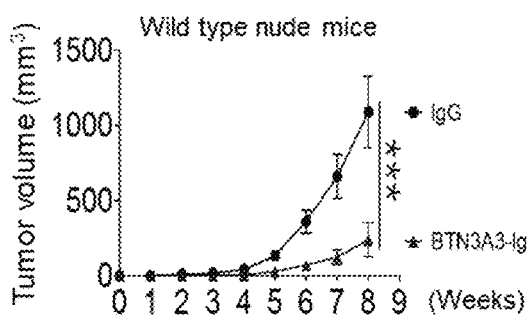
Figure 19:
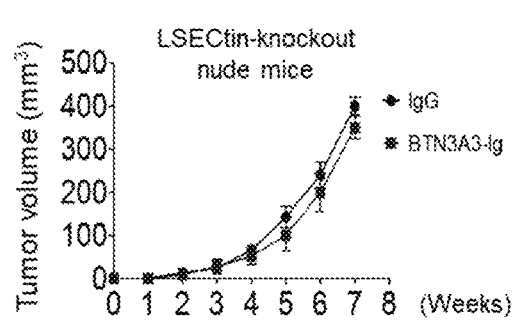

FIG. 18 is the detection result curve of fusion protein BTN3A3-Ig inhibiting tumor progression, FIG. 19 is the detection result curve of fusion protein BTN3A3-Ig inhibiting tumor progression-dependent on LSECtin.

Figure 20:
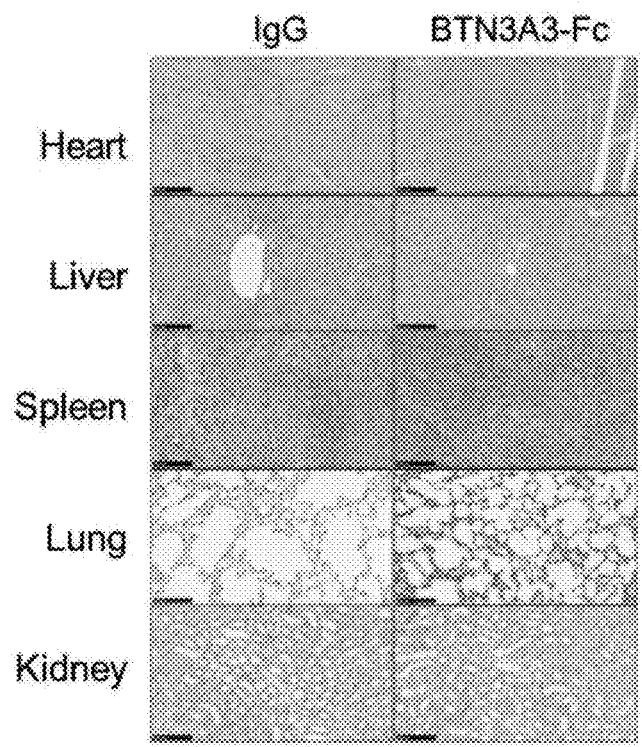
Figure 21:
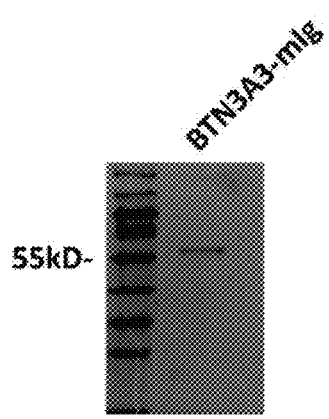

FIG. 20 is a diagram showing the sections of heart, liver, spleen, lung and kidney after the action of the experimental drug of Example 16. showing the detection result that the fusion protein BTN3A3-Ig inhibits tumor without toxic side effects, FIG. 21 is coomassie bright blue staining results of recombinantly expressed fusion protein BTN3A3-mIg.

Figure 22:
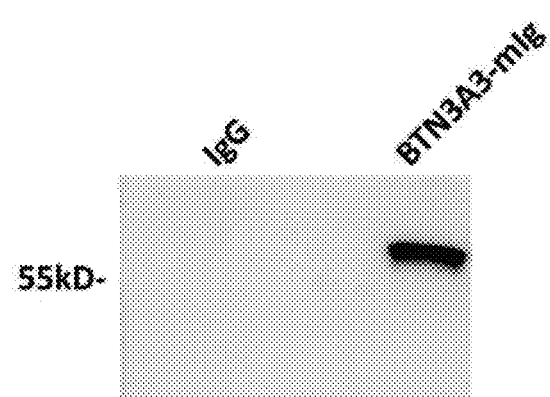

FIG. 22 is Western blot results of recombinantly expressed fusion protein BTN3A3-mIg.

FIG. 23 is a detection result of flow cytometre analysis, showing the ratio of binding of monoclonal antibody 5E08 secreted by hybridoma cells to BTN3A3.

FIG. 24 is a detection result of adhesion assay, showing that monoclonal antibody 5E08 blocks the interactions between protein LSECtin and membrane form BTN3A3.

FIG. 25 is a histogram of detection result, showing that monoclonal antibody 5E08 blocks LSECtin to promote tumor cell sternness.

FIG. 26 is the the detection result curve of a mouse prophylactic model for the inhibitory effect of monoclonal antibody 5E08 on tumor progression.

FIG. 27 is the the detection result curve of a mouse therapeutic model for the inhibitory effect of monoclonal antibody 5E08 on tumor progression.

Figure 28:
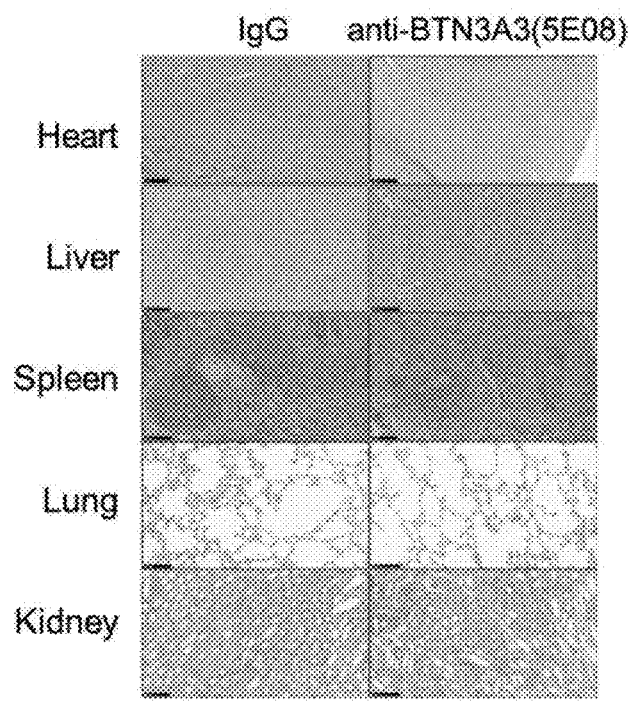

FIG. 28 is a diagram showing the sections of heart, liver, spleen, lung and kidney after the action of the experimental drug of Example 26, showing that the monoclonal antibody 5E08 has no toxic side effects on the mouse prophylactic model.

Figure 29:
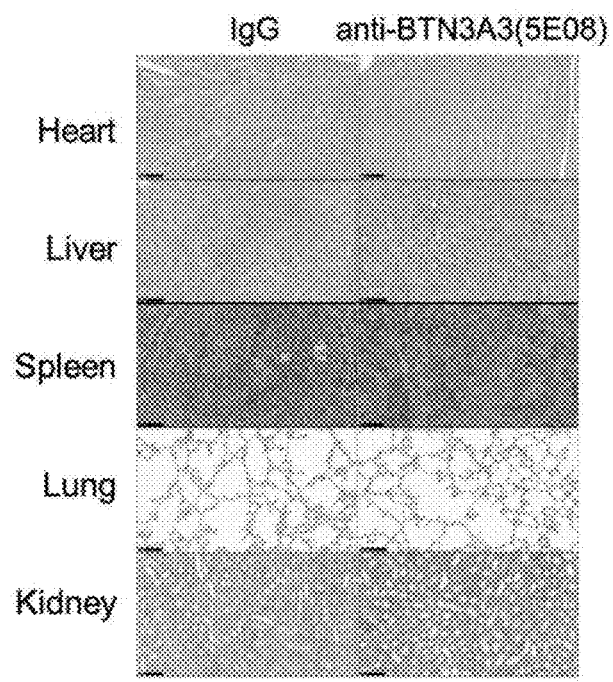

FIG. 29 is a diagram showing the sections of heart, liver, spleen, lung and kidney after the action of the experimental drug of Example 26, showing that the monoclonal antibody 5E08 has no toxic side effects on the mouse therapeutic model.

DETAILED EMBODIMENTS

In the study of tumor immunotherapy, it is known that LSECtin protein function includes negatively regulating T cell immune response in melanoma, promoting inflammatory reaction induced by Ebola virus, inhibiting CTL-dependent HBV virus clearance, promoting colon cancer tumor cell liver Shift. The inventors He Fuchu, Tang Li et at found that LSECtin may be used as a target for melanoma immunotherapy (CN104906575A, 2014100898325), and also found that LSECtin or a fusion protein containing LSECtin can he used to prepare drugs that inhibit cancer cells to tranfer to the liver, LSECtin Proteins and their fusion proteins can adhere to colon cancer cells and inhibit the homing migration of colon cancer cells to the liver, and become a new target for anti-adhesion treatment of tumor liver metastasis (CN101732715A, 2008102257147).

However, the functions of the LSECtin protein present in tumor cells or in metastatic organs disclosed in these prior art do not give an indication of whether LSECtin affects the formation and development of tumors in the case where the tumor cells themselves do not express LSECtin. In a recent study, the inventors unexpectedly discovered that tumor-associated macrophages also express LSECtin protein, and that the LSECtin protein expressed by the tumor-associated macrophage has characteristics of promoting tumor formation and development. The mechanism by which LSECtin protein exerts this property is to mediate the direct contact of tumor-associated macrophages with tumor cells and to promote the maintenance of tumor cell sternness. In view of this, it has been experimentally verified that the present invention first proposes that LSECtin proteins expressed by tumor-associated macrophages can be used as targets for immunotherapy of such tumors.

LSECtin (Liver Sinusoidal Endothelial Cells lectin) is a type II transmembrane glycoprotein, located on human 19p13.3, and is a new member of the C-type lectin family.

Based on the above research result, in view of the fact that the function of LSECtin protein promoting tumor occurrence and development depends on the direct contact with tumor cells and the maintenance of tumor cell sternness, the inventors further explored the interaction membrane protein of LSECtin and screened substances inhibiting the interaction between LSECtin and this kind of membrane protein, providing a new idea for the targeted treatment of tumor cell sternness.

After intensive research, the inventors first discovered that LSECtin can interact with BTN3A3 (Butyrophilin subfamily 3 member A3) expressed on the surface of tumor cells, thereby promoting the sternness of tumor cells and promoting the occurrence and development of tumors.

BTN3A3 (Butyrophilin subfamily 3 member A3) is a type I transmembrane glycoprotein, located on human 6p22.2, and is a member of the B7 superfamily. It is known that BTN3A3 protein may negatively regulate lymphocyte activity, and mutations of gene encoding BTN3A3 protein are associated with tumor susceptibility (Peedicayil, A., et al. Risk of ovarian cancer and inherited variants in relapse-associated genes. *PLoS One* 5, e8884 (2010).). In view of the tumor-expressed BTN3A3, the inventors have experimentally verified that it can be used as a target in tumor immunotherapy in the present invention.

Further, based on the discovery that the interaction between LSECtin and BTN3A3 expressed on the surface of tumor cells can promote the sternness of tumor cells, the inventors screened and excavated substances capable of blocking the interaction between LSECtin and BTN3A3, and developed them to be the targeted drugs inhibiting tumor-associated macrophages to promote the development of sternness.

Therefore, the present invention proposes a substance to block the interactions between LSECtin and BTN3A3, The substance can be used to inhibit the occurrence and development of tumors and inhibit tumor progression.

Specifically, the substance provided by the present invention is RNA molecule to interfere the expression of BTN3A2 and BTN3A3, or RNA molecule to interfere the expression of BTN3A3, Specifically, the substance provided by the present invention is a fusion protein, which is mainly consisted of human BTN3A3 and human IgG1 and can block the interaction between LSECtin and BTN3A3 expressed on the surface of cell, and the fusion protein is named BTN3A3-Ig.

Specifically, the substance provided by the present invention is a monoclonal antibody having the activity of inhibiting tumor progression, named 5E08. The present invention also provides the hybridoma cell line secreting the monoclonal antibody 5E08, named anti-P3(5E08).

The present invention will be further described in detail below in conjunction with specific examples. The methods used in the examples are conventional methods unless otherwise specified. For specific steps. see: «Molecular Cloning: A Laboratory Manual» (Sambrook, J., Russell, David W., Molecular Cloning: A Laboratory Manual, 3rd edition, 2001, NY, Cold Spring Harbor).

The percentage concentration is mass/mass (W/W, g/100 g) percentage concentration, mass/volume (W/V, g/100 mL) percentage concentration or volume/volume (V/V, mL/100 mL) percentage concentration unless otherwise specified.

The various biological materials described in the examples are obtained by merely providing an experimentally obtained route for the purpose of specific disclosure and should not be a limitation on the source of the biological material of the present invention. In fact, the sources of biological materials used are extensive, and any biological material that can be obtained without violating laws and ethics can be replaced by the instructions in the examples.

The methods used in the examples are conventional means unless otherwise specified.

The materials, reagent and other products used in the examples are available commercially unless otherwise specified.

The quantitative experiments of the examples are repeated three times and showed as the average results.

The RNA extraction kit, cDNA reverse transcription kit (A3500) and Mix (A6001) of the examples are obtained from Promega.

The cell counting chambers (Cat. 145-0011) of the examples are obtained from Biorad.

The CCK8 cell counting kit (Cat. CK04) of the examples is obtained from Dojido.

The qPCR primers of LSECtin (QT01034446), BTN3A2 (QT00060039) and BTN3A3 (QT00060039) of the examples are obtained from Qiagen.

4-6-week-old female nude mice of the examples are obtained from Beijing Vital River Laboratory Animal Technology Co., Ltd.

Collagenase IV (Cat. 05138) of the examples is obtained from Sigma-Aldrich.

DNase I of the examples is obtained from Seajet Scientific Inc.

Mouse MHC II Percp-cy5.5 of the examples is obtained from Biolegend.

Mouse Ly6G APC-cv7 (Cat. 560600), human CD14 V500mAb (Cat. 561392) and human CD15 PE-CF594 (Cat. 562372) of the examples are obtained from BD Bioscience.

Mouse Ly6C APC7 (Cat.17-5932), CD11b PE-cv7 (Cat. 561392), human CD3 FITC (Cat.11-0038), CD19 FITC (Cat. 11-0199), CD56 FITC (Cat.11-0566) and CD11 b PE-cy7 (Cat. 25-0118) of the examples are obtained from eBioscience.

In the blocking buffer of the examples, the solvent is water and the solute is $Na_2HPO_4$, $KH_2PO_4$, NaCl and dried skimmed milk, whose concentration is 0.02M, 0.0015M, 0.14M and 3% (mass percentage) in the blocking buffer, respectively.

The breast cancer cell line MDA-MB-231 of the examples is obtained from National Infrastructure of Cell Line Resource and is cultured by the manuals provided by the National Infrastructure of Cell Line Resource. The MDA-MB-231 cell line is cultured in the RPM 1640 medium (Thermo Fisher Scientific, Cat. SH130809.01B) with 10% FBS (Gibico, Cat. 10100-147-FBS) at 37° C., 5% $CO_2$.

MMTV-PyMT of the examples is spontaneous breast cancer model mouse. The $LSECtin^{+/+}PyMT$ is wild type spontaneous breast cancer mouse model. The $LSECtin^{-/-}PyMT$ is LSECtin-knockout spontaneous breast cancer mouse model. The detailed methods to obtain are as follows: mating C57B1/6J background wild type MMTV-PyMT spontaneous breast cancer model male mice with C57B1/6J background LSECtin-knockout female mice to obtain spontaneous breast cancer model male mouse in which LSECtin is heterozygous; mating this mouse with C57B1/6J background LSECtin-heterozygosis female mice to obtain $LSECtin^{+/+}PyMT$ (LSECtin-expressing spontaneous breast cancer mouse model) and $LSECtin^{-/-}PyMT$ (LSECtin-knockout spontaneous breast cancer mouse model) by genotype identification. In the above annotations, PyMT represents a spontaneous breast cancer model transgene, +/+ represents wildtype homozygotes, and −/− represents knockout homozygotes. The above C57B1/6J background LSECtin-knockout mice is described in the literature (Tang L, Yang J, Tang X, et al. The DC-SIGN family member LSECtin is a novel ligand of CD44 on activated T cells [J]. European journal of immunology, 2010, 40(4): 1185-1191), and the public can obtain it from Academy of Military Medical Sciences. The above C57B1/6J background wild type MMTV-PyMT spontaneous breast cancer mouse model is described in the literature (Davie S A, Maglione J E, Manner C K, et al. Effects of FVB/NJ and C57BL/6J strain backgrounds on mammary tumor phenotype in inducible nitric oxide synthase deficient mice[J]. Transgenic research, 2007, 16(2): 193-201), and the public can obtain it from Academy of Military Medical Sciences.

$LSECtin^{+/+}Nude^{-/-}$ of the examples is wild type nude mice. $LSECtin^{-/-}Nude^{-/-}$ is LSECtin-knockout nude mice. The detailed methods to obtain are as follows: mating BALB/c background male nude mice $LSECtin^{+/+}Nude^{-/-}$ (Beijing Vital River Laboratory Animal Technology Co., Ltd.) with BALB/c background female $LSECtin^{+/+}Nude^{-/-}$ mice to obtain $LSECtin^{+/-}Nude^{+/-}$ mice; mating male $LSECtin^{+/-}Nude^{+/-}$ mice with female $LSECtin^{+/-}Nude^{+/-}$ mice to obtain $LSECtin^{+/+}Nude^{-/-}$ (LSECtin-expressing wild type nude mice) and $LSECtin^{-/-}Nude^{-/-}$ (LSECtin-knockout nude mice) by genotype identification from their offspring. The above BALB/c background female LSECtin$^{-/-}$Nude$^{+/+}$ mice is described in the literature (Liu B, Wang M, Wang X, et al. Liver sinusoidal endothelial cell lectin inhibits CTL-dependent virus clearance in mouse models of viral hepatitis[J]. The Journal of immunology, 2013, 190(8): 4185-4195), and the public can obtain it from Academy of Military Medical Sciences.

Details of the mouse anti-human LSECtin antibody (Clone CCB059) in the examples have been published in (Zhao I), Han X, Zheng X, et al. The Myeloid LSECtin Is a DAP12-Coupled Receptor That is Crucial for Inflammatory Response induced by Ebola Virus Glycoprotein[J]. PLoS pathogens, 2016, 12(3)), and the public can also obtain it from Academy of Military Medical Sciences.

Details of rabbit anti-mouse LSECtin polyclonal antibody of the examples have been published in (Xu. F, Liu J, Liu D, et al. LSECtin expressed on melanoma cells promotes tumor progression by inhibiting antitumor T-cell responses[J]. Cancer research, 2014, 74(13): 3418-3428), and the public can obtain the antibody from Academy of Military Medical Sciences.

Details of murine LSECtin-Fc of the examples have been published in (Tang L, Yang J, Tang X, et al. The DC-SIGN family member LSECtin is a novel ligand of CD44 on activated T cells[J]. European journal of immunology, 2010, 40(4): 1185-1191), and the public can obtain it from Academy of Military Medical Sciences.

Example 1

LSECtin Promotes Tumor Formation

1. LSECtin Promotes Tumor Formationand Progression in the Spontaneous Breast Cancer Model Mice 1. Detection of the Tumor Volume of the Spontaneous Breast Cancer Model Mice The spontaneous breast cancer mouse model LSECtin$^{+/+}$PyMT and the spontaneous breast cancer mouse model LSECtin$^{-/-}$PyMT were separately raised and propagated in the experimental animal platform of Academy of Military Medical Sciences, Tumor volume was measured starting at 13 weeks. Then, once a week, the long diameter a and the short diameter h of the mouse tumor were measured using a vernier caliper, and the tumor volume was calculated. The calculation formula of the tumor volume was 0.5×ab². The mice were sacrificed until 22 weeks.

Figure 1A:
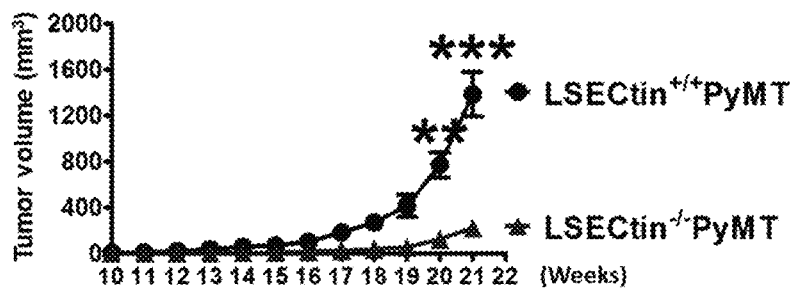

The detection results of tumor volume of the spontaneous breast cancer model mice were shown in the FIG. 1(a). The tumor volume of the LSECtin$^{\pm/+}$-PyMT mice at 11, 12, 13, 14, 15, 16, 17, 18, 19, 20, 21, 22 weeks was 0.000±0.000, 0.000±0.000, 0.000±0.000, 1.553±2.763, 3.566±4.912, 7.049±12.477, 13.867±18.089, 27.189±25.164, 90.020±53.954, 176.631±80.076, 709.085±334.051, 1017.960±434.164 (mm³), respectively; The tumor volume of the LSECtin$^{-/-}$-PyMT mice at 11, 12, 13, 14, 15, 16, 17, 18, 19, 20, 21, 22 weeks was 0.000±0.000, 0.000±0.000, 0.000±0.000, 0,658±1.612, 0.927±2.269, 1.795±4.397, 7.136±7,950, 12.340±13.105, 23.115±27.922, 36.883±41.680, 103.638±91.174, 173,123±112,662 (mm³), respectively. These results demonstrate that the tumor volume of the LSECtin$^{-/-}$-PyMT mice was significantly smaller than the tumor volume of the LSECtin$^{-/-}$-PyMT mice, indicating that LSECtin promoted tumor formation and tumor progression in spontaneous breast cancer in mice.

2. Detection of the Number of Tumor Foci in the Spontaneous Breast Cancer Model Mice A single spontaneous breast cancer mouse model LSECtin$^{+/+}$PyMT and a single spontaneous breast cancer mouse model LSECtin$^{-/-}$PyMT were raised and propagated in the experimental animal platform of Academy of Military Medical Sciences. The number of single tumor foci was counted starting at 14 weeks, and then observed every two weeks until 20 weeks, and the mice were sacrificed.

Figure 1B:
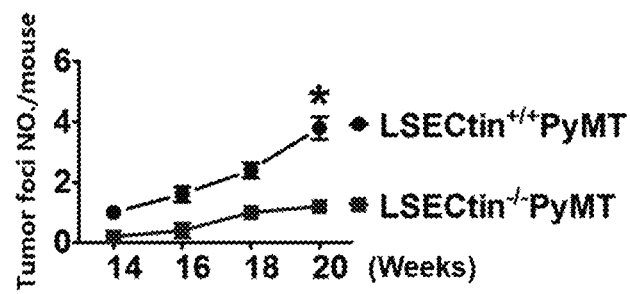

The detection results of the number of tumor foci in spontaneous breast cancer mice were shown in FIG. 1(b). It can be seen from the figure that the number of tumor foci of LSECtin$^{-/-}$-PyMT mice was significantly less than that of LSECtin$^{+/+}$-PyMT mice, indicating that LSECtin promoted tumor formation and tumor progression of spontaneous breast cancer mice.

3. Detection of the Number of Lung Tumor Metastatic Foci in the Spontaneous Breast Cancer Mouse Model A single spontaneous breast cancer mouse model LSECtin$^{+/+}$PyMT and a single spontaneous breast cancer mouse model LSECtin$^{-/-}$PyMT were raised and propagated in the experimental animal platform of Academy of Military Medical Sciences. At 20 weeks, the mice were sacrificed and the lungs were removed. HE staining results were obtained by paraffin embedding, tissue sectioning and staining, and the number of lung metastatic foci per section was obtained by counting.

Figure 1C:
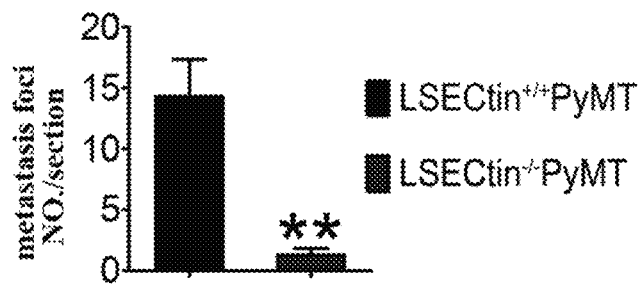

The detection results of lung cancer metastatic foci in spontaneous breast cancer mouse models were shown in FIG. 1(c). It can be seen from the figure that the number of lung tumor metastatic foci of LSECtin$^{-/-}$-PyMT mice was significantly less than that of LSECtin$^{+/+}$-PyMT mice, indicating that LSECtin promoted the transfer of spontaneous breast cancer to the lungs in mice.

II. Establishment of Human Breast Cancer Xenografts in Nude Mice and Observation of Tumor Volume 1000 human breast cancer cells MDA-MB-231, Matrigel (BD, 354230) and PBS (Hyclone, SH30256.01) were mixed to obtain a mixture; the mixture was planted with the mammary gland of 5-week-old female LSECtin$^{+/+}$Nude$^{-/-}$ Nude mice (LSECtin$^{+/+}$Nude$^{-/-}$ group) and LSECtin$^{-/-}$Nude$^{-/-}$nude mice (LSECtin$^{-/-}$Nude$^{-/-}$ group), respectively, to establish human breast cancer xenografts in nude mice. Observed once every other week for two months, the long diameter a and the short diameter h of the mouse tumor were measured using vernier calipers, and the tumor volume and tumor formation rate were calculated. The calculation formula of tumor volume was 0.5×ab², and the formula of tumor formation rate was the number of tumor formation/total number of model mice.

Figure 1D:
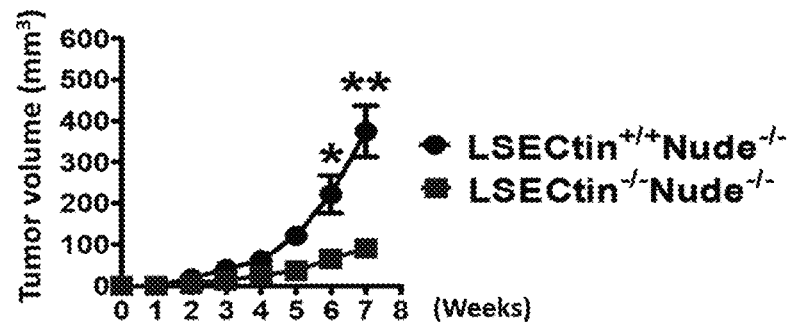

1. Detection of the Tumor Volume of the Human Breast Cancer Xenografts in Nude Mice The detection results of tumor volume in the LSECtin$^{+/+}$Nude$^{-/-}$ group and the LSECtin$^{-/-}$Nude$^{-/-}$ group were shown in FIG. 1(d). The tumor volumes of the LSECtin$^{+/+}$Nude$^{-/-}$ group mice were 0.000±0.000, 0.000±0.000, 23.820±9.802, 49.392±23.256, 73.482±38.720, 129.332±86.165, 228.424±170.106, 329.700±229.062 (mm³) at 0, 1, 2 At 3, 4, 5, 6, and 7 weeks, respectively; and the tumor volumes of the LSECtin$^{-/-}$Nude$^{-/-}$ group mice were 0.000±0.000, 0.000±0,000, 5.953±6.052, 13.096±10.624, 25.466±26.931, 37.257±40.210, 65.645±53.518, and 91.430±59.608 (mm³) at 0, 1, 2, 3, 4, 5, 6, and 7 weeks, respectively. These results demonstrated that the tumor volume of the LSECtin$^{-/-}$Nude$^{-/-}$ mice was significantly smaller than that of the LSECtin$^{+/+}$Nude$^{-/-}$ mice, indicating that LSECtin can promote the tumor formation of breast cancer in mice.

2. Detection of the Tumor Formation Rate of the Human Breast Cancer Xenografts in Nude Mice The detection results of the tumor formation rate of the LSECtin$^{+/+}$Nude$^{-/-}$ group and the LSECtin$^{-/-}$Nude$^{-/-}$ group were shown in Table 1. The tumor formation rate of LSECtin$^{-/-}$Nude$^{-/-}$ mice was significantly lower than that of LSECtin$^{-/-}$Nude$^{-/-}$ mice, indicating that LSECtin can promote the tumor formation of breast cancer in mice.

TABLE 1

Detection results of tumor formation rate in nude mice

| Group | Mouse Number with Tumor/ Total Mouse Number | Tumor formation rate (%) |
|---|---|---|
| LSECtin$^{+/+}$Nude$^{-/-}$ | 5/11 | 46 |
| LSECtin$^{-/-}$Nude$^{-/-}$ | 1/8 | 12 |

Example 2

Detection of LSECtin Expression Level in Tumor Microenvironment

I. Detection of LSECtin Expression Level in Mouse Breast Cancer Microenvironment 1. Isolation of Tumor Infiltrating Myeloid Cells from MMTV-PyMT Spontaneous Breast Cancer Mouse Model, Human Breast Cancer Xenografts in Nude Mice and Clinical Samples (1) Preparation for digestive juice: 20 ml 1640 medium (Hyclone, SH30809), 20 mg type IV collagenase (Sigma-Aldrich Inc.) and 1 mg DNase I (Sigma- Aldrich Inc.) were mixed to obtain the digestive juice, which was filtered through a 0.45 μm filter.

(2) The mammary gland tumor tissues planted for 8 weeks from the mice of MMTV-PyMT spontaneous breast cancer models and human breast cancer xenografts in nude mice, or fresh clinical tumor samples were dissected, minced into small pieces and digested for 40 minutes at 37° C. in the digestive juice as shown in the Step (1) to obtain tumor digestive juice.

(3) The tumor digestive juice was filtered through a 70 μm filter and centrifuged at 250 g for 10 min.

(4) The tumor cells in the tumor digestive juice were washed 3 times with 1640 medium, and the following tumor infiltrating myeloid cells (flow-labeled in parentheses) of each mouse model were obtained by flow sorting: tumor-associated macrophage TAM: (CD45$^+$CD11b$^+$CD11c$^+$MHC II $^+$Ly6C$^-$Ly6G$^-$); monocyte Mo: (CD45$^+$CD11b$^+$CD11c$^-$MHC$^-$Ly6C$^+$Ly6G$^-$); tumor-associated neutrophil TAN: (CD45$^+$CD11b$^+$CD11c$^{+/-}$MHC II $^-$Ly6C$^+$Ly6G$^+$); other myeloid cells CD11b$^-$MHC II$^-$: (CD45$^+$CD11b$^-$MHC II$^-$).

2. Detection of LSECtin Expression Level of MMTV-PyMT Mouse Spontaneous Breast Cancer Microenvironment and Human Breast Cancer Transplantation Microenvironment by qPCR (1) RNA was extracted from the tumor infiltrating myeloid cells of each mouse model obtain in step 1 according to the method of the RNA extraction kit; and the cDNA is synthesized according to the method of the cDNA synthesis kit.

(2) Using the cDNA obtained in the step (1) as a template, the LSECtin and GAPDH were amplified using a realtime fluorescent quantitative nucleic acid amplification detection system, and the relative expression of LSECtin was analyzed by software. Primers sequences were shown below (5' to 3'):

```
Lsectin Forward:
                                (SEQ ID NO: 17)
GGTGCCCATCTGGTGATTGT;

Lsectin Reverse:
                                (SEQ ID NO: 18)
CAGTGGCTGAAGTTGAGTGAGG;

Gapdh Forward:
                                (SEQ ID NO: 19)
AGGTCGGTGTGAACGGATTTG;

Gapdh Reverse:
                                (SEQ ID NO: 20)
TGTAGACCATGTAGTTGAGGTCA.
```

Figures 2A, 2B, 2C, 2D, 2E, 2F, 2G, 2H, 2I, 2J, 2K:
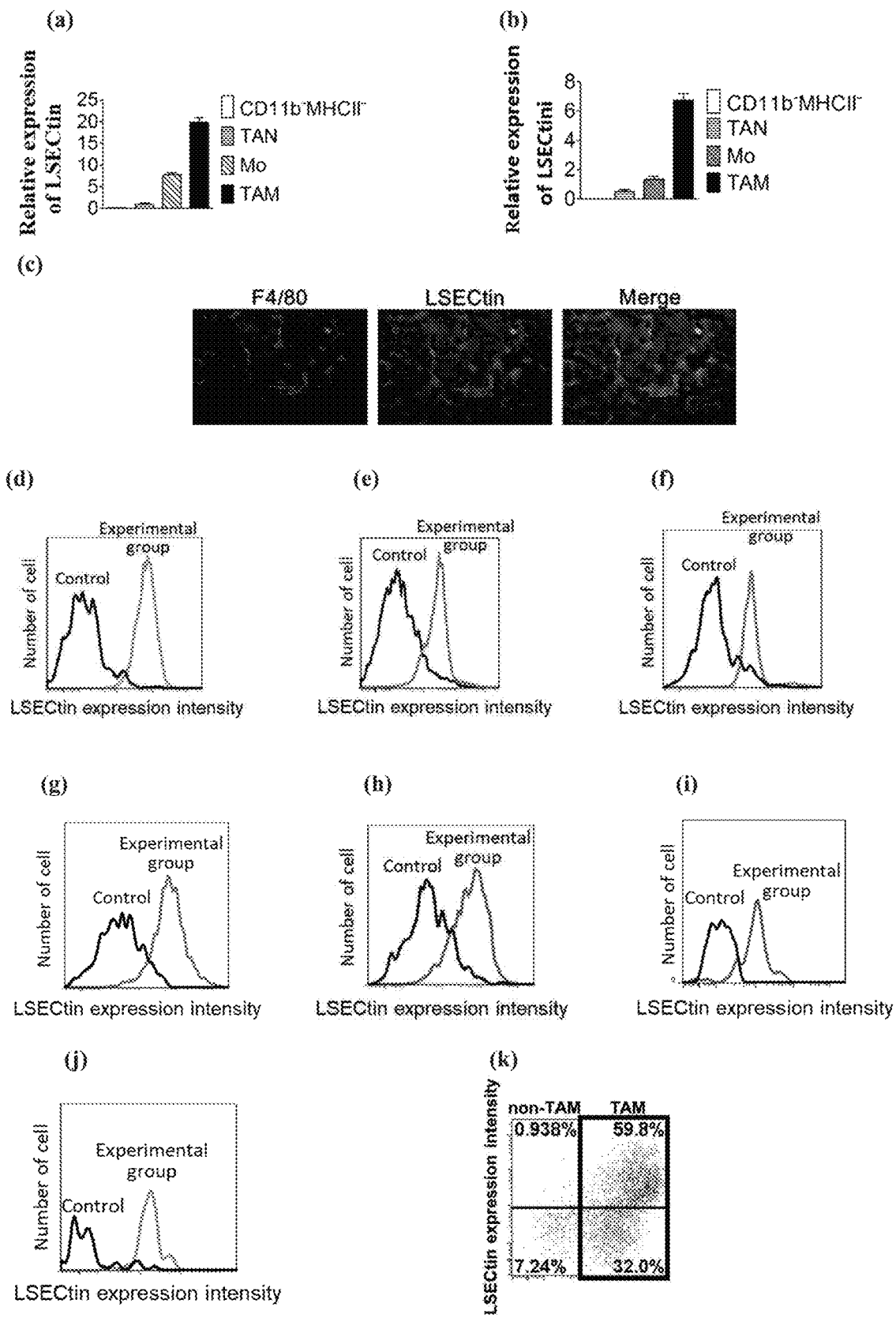
FIG. 2(a) is a histogram of the mRNA expression level, showing the qPCR detection of LSECtin expression level in the tumor microenvironment of MMTV-PyMT spontaneous breast cancer mice, wherein CD11b⁻MHC II⁻ represents lymphocyte, TAM represents tumor-associated macrophage, TAN represents tumor-associated neutrophil and Mo represents monocyte.
FIG. 2(b) is a histogram of the mRNA expression level, showing the qPCR detection of LSECtin expression level in the tumor microenvironment of human breast cancer xenografts in nude mice.
FIG. 2(c) is the result of in situ immunofluorescence staining of the mouse tumor, showing that LSECtin colocalizes with macrophage marker molecule F4/80 in the spontaneous breast cancer microenvironment of MMTV-PyMT mice.
FIG. 2(d) is a peak diagram of LSECtin expression level by flow cytometric analysis, showing the LSECtin expression level on the surface of TAMs from human breast cancer.
FIG. 2(e) is a peak diagram of LSECtin expression level by flow cytometric analysis, showing the LSECtin expression level on the surface of TAMs from myeloma patient.
FIG. 2(f) is a peak diagram of LSECtin expression level by flow cytometric analysis, showing the LSECtin expression level on on the surface of TAMs from lung cancer patient.
FIG. 2(g) is a peak diagram of LSECtin expression level by flow cytometric analysis, showing the LSECtin expression level on the surface of TAMs from colorectal carcinoma patient.
FIG. 2(h) is a peak diagram of LSECtin expression level by flow cytometric analysis, showing the LSECtin expression level on the surface of TANN from giant-cell tumor patient.
FIG. 2(i) is a peak diagram of LSECtin expression level by flow cytometric analysis, showing the LSECtin expression level on the surface of TAMs from renal carcinoma patient.
FIG. 2(j) is a peak diagram of LSECtin expression level by flow cytometric analysis, showing the LSECtin expression level on the surface of TAMs from laryngocarcinoma patient.
FIG. 2(k) is a peak diagram of LSECtin expression level by flow cytometric analysis, showing the LSECtin expression level on the surface of TAMs from parotid gland carcinoma patient.

The results were shown in FIG. 2. FIG. 2(a) showed the qPCR detection result of LSECtin expression in the MMTV-PyMT mouse spontaneous breast cancer microenvironment; FIG. 2(b) showed the qPCR detection result of LSECtin expression in the tumor microenvironment of the human breast cancer xenografts in nude mice. It can be seen from the figures that LSECtin was highly expressed in breast cancer tumor-associated macrophages (TAM) of MMTV-PyMT and human breast cancer xenografts in nude mice, and was lowly expressed in mononuclear infiltrating cells (Mo) and granulocytes (TAN).

3. Detection of LSECtin Expression Level of MMTV-PyMT Mouse Spontaneous Breast Cancer Microenvironment by Immunofluorescence (1) The specimen was added with a small amount of OCT embedding agent, placed in a cryostat, sliced to a section having a thickness of 4-5 μm, and attached to a glass slide for use. Dry at room temperature for 30 min.

(2) Washed with PBS for 5 min×3 times.

(3) Washed in 0.01M PBS for 3 min×3 times.

(4) Incubated with 0.3% Tritonx-100 for 30 minutes (without washing, and sucking out 0.3% Tritonx-100).

0.3%Tritonx-100: First 3% Tritonx-100 10 ml (0.3 ml Trixtonx-100 stock solution. 9.7 ml PBS), and then diluted to 0.3% Tritonx-100.

(5) The section was blocked with 5% goat serum at 37° C. for 30 minutes (without washing, and sucking out serum), and rabbit anti-mouse LSECtin polyoxin diluted to the working concentration with antibody dilution (3% Tritonx-100 0.4 ml, BSA 0.04 g, PBS 3.6 ml) was added. The negative control abeam was replaced with 0.01 M PBS and placed in a humidified box overnight at 4° C.

(6) Washed in 0.01M PBS for 3 min×3 times to remove unconjugated LSECtin polyoxin.

(7) The diluted fluorescein-labeled antibody (the fluorescent antibody could be diluted with 0.01 M PBS (pH 7.4)) was added dropwise, and incubated at room temperature for 1-2 hours or 37° C. for 30 min.

(8) Washed in PBS for 5 min/3 times to remove unconjugated antibody.

(9) Counterstained cell nuclei: Hoechst33258 was incubated at room temperature for

(10) Washed in 0.01M PBS for 3 min/3 times.

(11) Lightly air-dried sections at room temperature.

(12) Observed under a confocal microscope and images were acquired.

The results of in situ immunofluorescence staining of mouse tumors were shown in FIG. 2(c): co-localization of LSECtin and macrophage marker F4/80 in the MMTV- PyMT mouse spontaneous breast cancer microenvironment, indicating that in the MMTV-PyMT mouse spontaneous breast cancer microenvironment, LSECtin is highly expressed in TAM.

II. Detection of LSECtin Expression Level in Tumor Tissues of Patients with Breast Cancer Tissue cells were isolated from fresh clinical patient tumor samples and tumor infiltrating immune cell subpopulations were obtained by flow cytometry. The specific steps were as follows: the living cell population was sequentially passed through SSC-H/FSC-W and SSC-W/FSC-H to remove adhesion cells. SSC-A and FSC-A to remove cell debris, $CD45^+$ to obtain immune cell subpopulations, $CD3^-CD19^-CD56^-$ to obtain myeloid cell enrichment subpopulations, CD14, CD11b and CD15 to define TAM ($CD11b^+CD14^+CD15^+$), resulting in tumor-associated macrophages of $CD45^+CD3^-CD15^-CD19^-CD56^-CD11b^+CD14^+$, which were labeled with the flow antibody as the experimental group; the isotype control antibody was used as the control group, The detectipon result of LSECtin expression level by flow cytometric was shown in FIG. 2(d): LSECtin was highly expressed in tumor-associated macrophages of $CD45^+CD3^-CD15^-CD19^-CD56^-CD11b^+CD14^+$ from breast cancer.

III. Detection of LSECtin Expression Level in Tumor Tissues of Patients with Myeloma Tissue cells were isolated from tumor samples from fresh clinical myeloma patients, and tumor infiltrating immune cell subpopulations were obtained by flow cytometry. The specific steps were as follows: the living cell population was sequentially passed through SSC-H/FSC-W and SSC-W/FSC-H to remove adhesion cells, SSC-A and FSC-A to remove cell debris, $CD45^+$ to obtain immune cell subpopulations. $CD3^-CD19^-CD56^-$ to obtain myeloid cell enrichment subpopulations, CD14, CD11b and CD15 to define TAM ($CD11b^+CD14^+CD15^-$), resulting in tumor associated macrophages of $CD45^+CD3^-CD15^-CD19^-CD56^-CD11b^+CD14^+$, which were labeled with LSECtin flow antibody as the experimental group; the isotype control antibody was used as the control group.

The detectipon result of LSECtin expression level by flow cytometric was shown in FIG. 2(e): LSECtin was highly expressed in tumor-associated macrophages of $CD45^+CD3^-CD15^-CD19^-CD56^-CD11b^+CD14^+$ from myeloma.

IV. Detection of LSECtin Expression Level in Tumor Tissues of Patients with Lung Cancer Tissue cells were isolated from tumor samples from fresh clinical lung cancer patients, and tumor infiltrating immune cell subpopulations were obtained by flow cytometry. The specific steps were as follows: the living cell population was sequentially passed through SSC-H/FSC-W and SSC-W/FSC-H to remove adhesion cells. SSC-A and FSC-A to remove cell debris. $CD45^+$ to obtain immune cell subpopulations, $CD3^-CD19^-CD56^-$ to obtain myeloid cell enrichment subpopulations, CD14, CD11b and CD15 to define TAM ($CD11b^+CD14^+CD15^-$), resulting in tumor associated macrophages of $CD45^+CD3^-CD15^-CD19^-CD56^-CD11b^+CD14^+$, which were labeled with LSECtin flow antibody as the experimental group; the isotype control antibody was used as the control group.

The detectipon result of LSECtin expression level by flow cytometric was shown in FIG. 2(f): LSECtin was highly expressed in tumor-associated macrophages of $CD45^+CD3^-CD15^-CD19^-CD56^-CD11b^+CD14^+$ from lung cancer.

V. Detection of LSECtin Expression Level in Tumor Tissues of Patients with Colorectal Cancer Tissue cells were isolated from tumor samples from fresh clinical colorectal cancer patients, and tumor infiltrating immune cell subpopulations were obtained by flow cytometry. The specific steps were as follows: the living cell population was sequentially passed through SSC-H/FSC-W and SSC-W/FSC-H to remove adhesion cells, SSC-A and FSC-A to remove cell debris, $CD45^+$ to obtain immune cell subpopulations, $CD3^-CD19^-CD56^-$ to obtain myeloid cell enrichment subpopulations. CD14, CD11b and CD15 to define TAM ($CD11b^+CD14^+CD15^-$), resulting in tumor associated macrophages of $CD45^+CD3^-CD15^-CD19^-CD56^-CD11b^+CD14^+$, which were labeled with LSECtin flow antibody as the experimental group; the isotype control antibody was used as the control group.

The detectipon result of LSECtin expression level by flow cytometric was shown in FIG. 2(g): LSECtin was highly expressed in tumor-associated macrophages of $CD45^+CD3^-CD15^-CD19^-CD56^-CD11b^+CD14^+$ from colorectal cancer.

VI. Detection of LSECtin Expression Level in Tumor Tissues of Patients with Giant-Cell Tumor Tissue cells were isolated from tumor samples from fresh clinical giant-cell tumor patients, and tumor infiltrating immune cell subpopulations were obtained by flow cytometry. The specific steps were as follows: the living cell population was sequentially passed through SSC-H/FSC-W and SSC-W/FSC-H to remove adhesion cells, SSC-A and FSC-A to remove cell debris, $CD45^+$ to obtain immune cell subpopulations, $CD3^-CD19^-CD56^-$ to obtain myeloid cell enrichment subpopulations, CD14. CD11b and CD15 to define TAM ($CD11b^+CD14^+CD15^-$), resulting in tumor associated macrophages of $CD45^+CD3^-CD15^-CD19^-CD56^-CD11b^+CD14^+$, which were labeled with LSECtin flow antibody as the experimental group; the isotype control antibody was used as the control group.

The detectipon result of LSECtin expression level by flow cytometric was shown in FIG. 2(h): LSECtin was highly expressed in tumor-associated macrophages of $CD45^+CD3^-CD15^-CD19^-CD56^-CD11b^+CD14^+$ from giant-cell tumor.

VII. Detection of LSECtin Expression Level in Tumor Tissues of Patients with Renal Cancer Tissue cells were isolated from tumor samples from fresh clinical renal cancer patients, and tumor infiltrating immune cell subpopulations were obtained by flow cytometry. The specific steps were as follows: the living cell population was sequentially passed through SSC-H/FSC-W and SSC-W/FSC-H to remove adhesion cells, SSC-A and FSC-A to remove cell debris. $CD45^+$ to obtain immune cell subpopulations, $CD3^-CD19^-CD56^-$ to obtain. myeloid cell enrichment subpopulations, CD14, CD11b and CD15 to define TAM ($CD11b^+CD14^+CD15^-$), resulting in tumor associated macrophages of $CD45^+CD3^-CD15^-CD19^-CD56^-CD11b^+CD14^+$, which were labeled with LSECtin flow antibody as the experimental group; the isotype control antibody was used as the control group.

The detectipon result of LSECtin expression level by flow cytometric was shown in FIG. 2(i): LSECtin was highly expressed in tumor-associated macrophages of $CD45^+CD3^-CD15^-CD19^-CD56^-CD11b^+CD14^+$ from renal cancer.

VIII. Detection of LSECtin Expression Level in Tumor Tissues of Patients with Laryngo Cancer Tissue cells were isolated from tumor samples from fresh clinical laryngo cancer patients, and tumor infiltrating immune cell subpopulations were obtained by flow cytometry. The specific steps were as follows: the living cell population was sequentially passed through SSC-H/FSC-W and SSC-W/FSC-H to remove adhesion cells, SSC-A and FSC-A to remove cell debris, $CD45^+$ to obtain immune cell subpopulations, CD3⁻CD19⁻CD56⁻ to obtain myeloid cell enrichment subpopulations, CD14, CD11b and CD15 to define TAM (CD11b⁺CD14⁺CD15⁻), resulting in tumor associated macrophages of CD45⁺CD3⁻CD15⁻CD19⁻CD56⁻CD11b⁺CD14⁺, which were labeled with LSECtin flow antibody as the experimental group; the isotype control antibody was used as the control group.

The detectipon result of LSECtin expression level by flow cytometric was shown in FIG. 2(j): LSECtin was highly expressed in tumor-associated macrophages of CD45⁺CD3⁻CD15⁻CD19⁻CD56⁻CD11b⁺CD14⁺ from laryngo cancer.

IX. Detection of LSECtin Expression Level in Tumor Tissues of Patients with Parotid Gland Cancer Tissue cells were isolated from tumor samples from fresh clinical parotid gland cancer patients, and tumor infiltrating immune cell subpopulations were obtained by flow cytometry. The specific steps were as follows: the living cell population was sequentially passed through SSC-H/FSC-W and SSC-W/FSC-H to remove adhesion cells, SSC-A and FSC-A to remove cell debris, CD45⁺ to obtain immune cell subpopulations, CD3⁻CD19⁻CD56⁻ to obtain myeloid cell non-granulocyte enrichment subpopulations, wherein CD11b⁺ defined TAM, resulting in tumor associated macrophages of CD45⁺CD3⁻CD15⁻CD11b⁺ (TAM group), CD45⁺CD3⁻CD15⁺CD19⁻CD56⁻CD11b⁺ was the non-TAM group.

The detectipon result of LSECtin expression level by flow cytometric was shown in FIG. 2(k): LSECtin was highly expressed in tumor-associated macrophages of CD45⁺CD3⁻CD15⁻CD19⁻CD56⁻CD11b⁺ from parotid gland cancer.

Example 3

Macrophage-Specific LSECtin-Knockout Inhibits Tumor Progression

The MMTV-PyMT in the following examples was a spontaneous breast cancer model mouse; LyZ2$^{Cre}$ was a mouse with LyZ2 gene Cre enzyme knock-in; LSECtin$^{fl/fl}$ was a mouse with LoxP gene knock-in; WT-PyMT-LyZ2 was wild-type spontaneous breast cancer model mouse, KO-PyMT-LyZ2 was a macrophage LSECtin knockout spontaneous breast cancer model mouse. The specific methods were as follows: mating C57B1/6J background wild type MMTV-PyMT spontaneous breast cancer model male mouse with C57B1/6J background LyZ2$^{Cre}$ female mouse to obtain the spontaneous breast cancer model male mouse with Cre enzyme knock-in by genotype identification. The mouse was mated with C57B1/6J background LSECtin$^{fl/fl}$ female mouse, obtaining the spontaneous breast cancer model male mouse with Cre knock-in and the LoxP gene heterozygosis by genotype identification. The mouse was mated with the mouse with LoxP gene knock-in to obtain WT-PyMT-LyZ2 mouse (MMTV⁺LyZ2$^{Cre-}$LSECtin$^{fl/fl}$) and KO-PyMT-LyZ2 mouse (MMTV⁺LyZ2$^{Cre+}$LSECtin$^{fl/fl}$). In the above annotations, MMTV represented spontaneous breast cancer model transgene, Cre– represented Cre enzyme non-knock-in, Cre+ represented Cre enzyme knock-in, fl/-represented LoxP gene knock-in heterozygote, and fl/fl represented. LoxP gene knock-in homozygote. The above-mentioned Cre knock-in mouse can be purchased from Jackson, and. LoxP gene knock-in mouse can be purchased from TACONIC, and the public can also obtain them from the Beijing Proteome Research Center. The above C57B1/6J background wild type MMTV-PyMT spontaneous breast cancer model mouse has been published (Davie S A, Maglione J E, Manner C K, et al. Effects of FVB/NJ and C57BL/6J strain backgrounds on mammary tumor phenotype in inducible nitric oxide synthase deficient mice[J]. Transgenic research, 2007, 16(2): 193-201), and the public can obtain it from the Beijing Proteome Research Center.

1. Detection of Tumor Volume of Macrophage-Specific LSECtin-Knockout Spontaneous Breast Cancer Model Mouse The macrophage LSECtin-knockout spontaneous breast cancer model control group mouse WT-PyMT-LyZ2 and the experimental group KO-PyMT-LyZ2 were raised and propagated in the animal platform of the National Proteome Research Center. Tumor volume was measured starting at 13 weeks. Then, once a week, the long diameter a and the short diameter b of the mouse tumor were measured using a vernier caliper, and the tumor volume was calculated. The calculation formula of the tumor volume was $0.5 \times ab^2$. The mice were sacrificed until 21 weeks.

The detection results of tumor volume in spontaneous breast cancer model mice were shown in FIG. 14. At the 11th, 12th, 13th, 14th, 15th, 16th, 17th, 18th, 19th, 20th, and 21st week, the tumor volumes of WT-PyMT-LyZ2 mouse were 0.00±0.000, 3.94±7.63, 17.16±23.96, 34.56±37.33, 81.59±79.46, 106.29±93.45, 188.42±127.41, 396.37±181.39, 599.75±224.66, 814.60±336.65, 1227.49±516.97 (mm³), respectively; and at the 11th, 12th, 13th, 14th, 15th, 16th, 17th, 18th, 19th, 20th, and 21st week, the tumor volumes of the KO-PyMT-LyZ2 group mouse were 0.000±0.000, 0.000±0.000, 3.00±11.25, 9.32±15.89, 11.01±19.49, 34.71±43.83, 96.71±98.74, 203.46±196.01, 272.47±254.20, 440.47±315.91, 653.70±419.70 (mm³), respectively. The above results indicated that the tumor volume of mouse in KO-PyMT-LyZ2 group was significantly smaller than that in WT-PyMT-LyZ2 group, indicating that knockout of macrophage LSECtin significantly inhibited tumor formation and tumor progression in mouse breast cancer.

2. Detection of Number of Tumor Foci of Macrophage-Specific LSECtin-Knockout Spontaneous Breast Cancer Mouse Model The macrophage LSECtin-knockout spontaneous breast cancer model control group WT-PyMT-LyZ2 and the experimental group KO-PyMT-LyZ2 were raised and propagated in the animal platform of the National Proteome Research Center. The number of single tumor foci was counted starting at 14 weeks, and then observed every two weeks until 20 weeks, and the mice were sacrificed.

The detection results of the number of tumor foci in spontaneous breast cancer mouse model were shown in FIG. 15. As can be seen from the figure, the number of tumor foci in KO-PyMT-LyZ2 single mouse was significantly less than that in WT-PMT-LyZ2 mouse, indicating that knockout of macrophage LSECtin significantly inhibited tumor formation and tumor progression in mouse breast cancer.

3. Detection of Number of Lung Tumor Metastasis Foci of Macrophage-Specific LSECtin-Knockout Spontaneous Breast Cancer Mouse Model A single spontaneous breast cancer model mouse WT-PyMT-LyZ2 and a single spontaneous breast cancer mouse model KO-PyMT-LyZ2 were raised and propagated in the animal platform of the National Proteome Research Center. At 25 weeks, the mice were sacrificed, and the lungs were removed. HE staining results were obtained by paraffin embedding, tissue sectioning and staining, and the number of lung metastases loci per section was obtained by counting.

The detection results of lung cancer metastasis foci in spontaneous breast cancer mice were shown in FIG. 16. As can be seen from the figure, the number of lung tumor metastasis foci in KO-PyMT-LyZ2 single mouse was significantly less than that in WT-PyMT- In LyZ2 mouse, indicating that the knockout of macrophage LSECtin significantly inhibited the metastasis of spontaneous breast cancer to the lungs in mice.

Example 4

Various Tumor Cells of Clinical Samples Express BTN3A2 and BTN3A3

1. Isolation of Tumor Cells from Clinical Samples (1) Preparation for digestive juice: 20 ml of 1640 medium (Hyclone, SH30809), 20 mg of collagenase IV and 1 mg of RNase I were mixed to obtain a digestive juice, which was filtered through a 0.45 mm filter.

(2) The tumor tissues of fresh clinical patients were taken separately, and then tutted into small pieces and digested for 40 minutes at 37° C. in the digestive juice as shown in the Step (1) to obtain tumor digestive juice.

(3) The tumor digestive juice was filtered through a 70 μm filter and centrifuged at 250 g for 10 min.

(4) The tumor cells in the tumor digestive juice were washed 3 times with 1640 medium, and the tumor cell enrichment subpopulations were obtained by flow sorting respectively: the specific steps were as follows: the living cell population was sequentially passed through SSC-H/FSC-W and SSC-W/FSC-H to remove adhesion cells, SSC-A and FSC-A to remove cell debris. CD45$^-$ to obtain tumor cell enrichment subpopulations, and the expression of BTN3A was detected by anti-CD277 antibody (the antibody simultaneously recognizes BTN3A1, BTN3A2, BTN3A3 in membrane form).

2. Detection of Tumor Cell BTN3A Expression Level in Tumor Tissues of Patients with Breast Cancer According to the above description, the expression level of tumor cell BTN3A in tumor tissues of patients with breast cancer was detected.

Figures 3A, 3B, 3C, 3D, 3E, 3F:
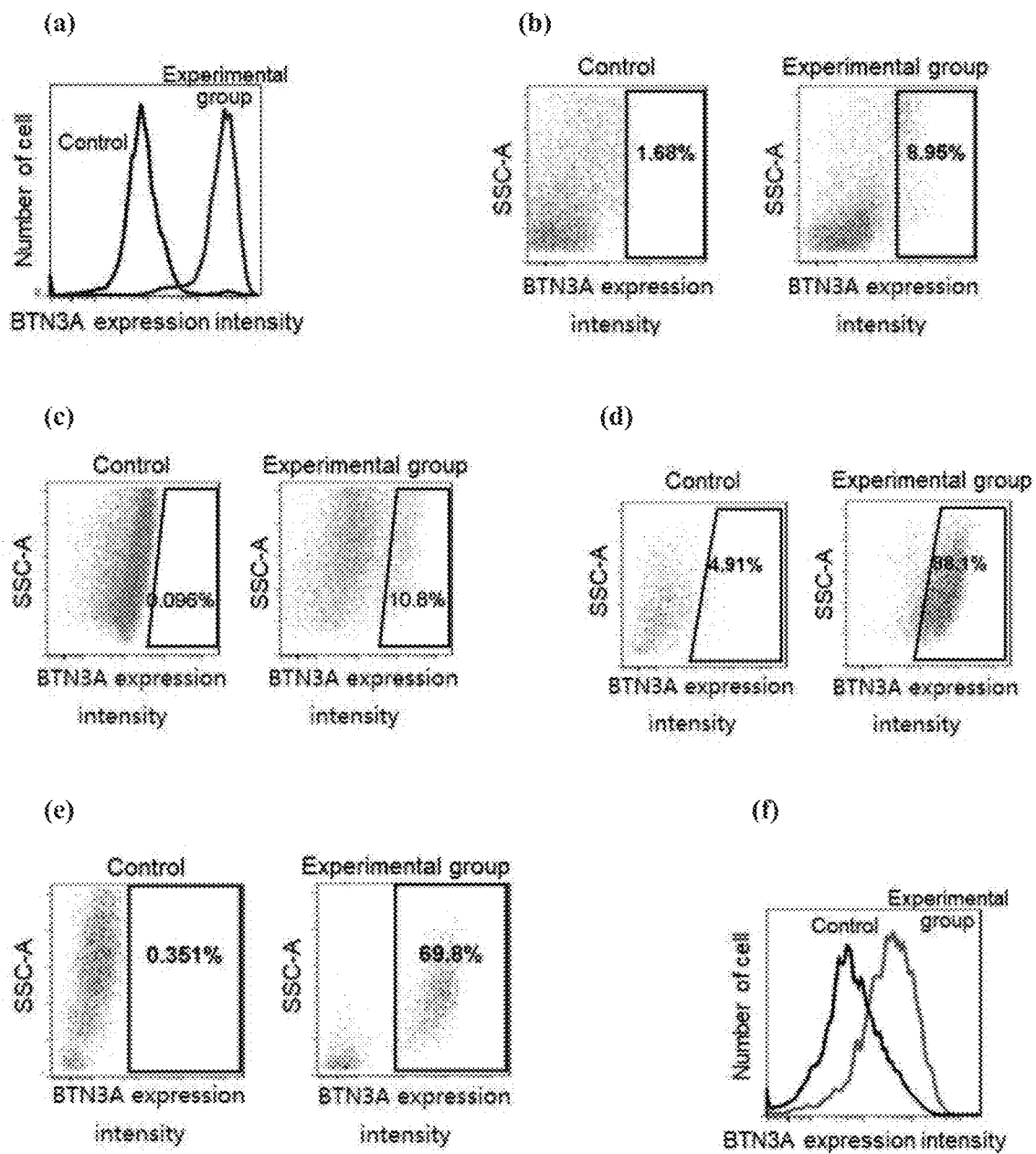
FIG. 3(a) is a peak diagram of BTN3A expression level of breast cancer patient by flow cytometric analysis, showing the BTN3A expression level on the surface of the tumor cells in tumor tissue.
FIG. 3(b) is a scatter diagram of BTN3A expression level by flow cytometric analysis, showing the BTN3A expression level on the surface of the tumor cells in tumor tissue from lung cancer patient.
FIG. 3(c) is a scatter diagram of BTN3A expression level by flow cytometric analysis, showing the BTN3A expression level on the surface of the tumor cells in tumor tissue from colorectal carcinoma patient.
FIG. 3(d) is a scatter diagram of BTN3A expression level by flow cytometric analysis, showing the BTN3A expression level on the surface of the tumor cells in tumor tissue from giant-cell tumor patient.
FIG. 3(e) is a scatter diagram of BTN3A expression level by flow cytometric analysis, showing the BTN3A expression level on the surface of the tumor cells in tumor tissue from renal carcinoma patient.
FIG. 3(f) is a peak diagram of BTN3A expression level by flow cytometric analysis, showing the BTN3A expression level on the surface of the tumor cells in tumor tissue from parotid gland carcinoma patient.
Figure 4A:
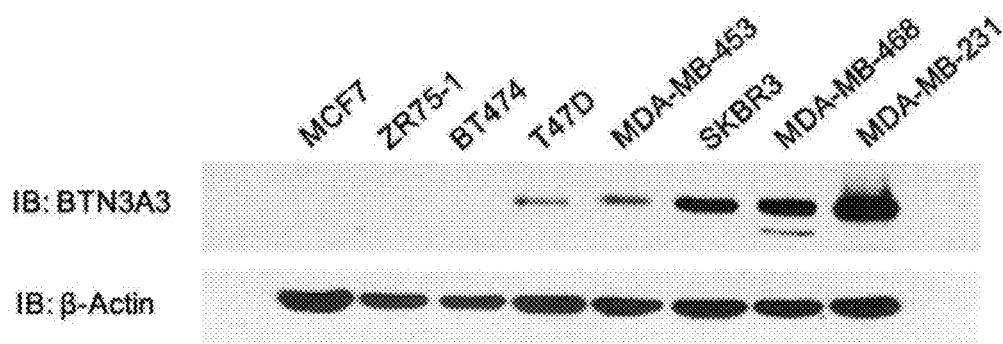
FIG. 4(a) is Western blot results of BTN3A3 expression in the various breast cancer cell lines.
Figure 4B:
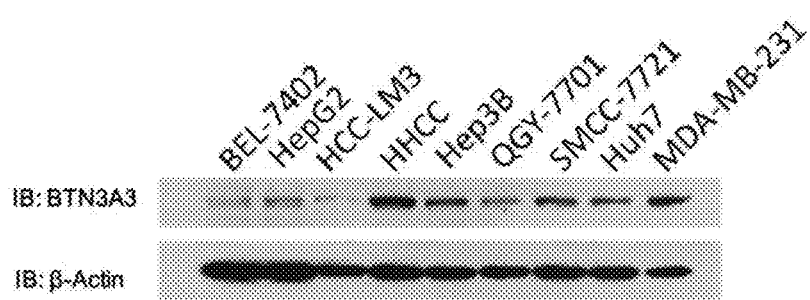
FIG. 4(b) is Western blot results of BTN3A3 expression in the various liver cancer cell lines.
Figure 4C:
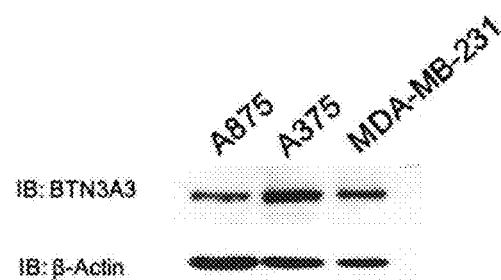
FIG. 4(c) is Western blot results of BTN3A3 expression in the human melanoma cell lines.
Figure 4D:
FIG. 4(d) is Western blot results of BTN3A3 expression in the various gastric carcinoma cell lines.
Figure 4E:
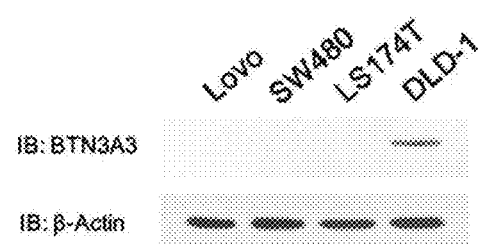
FIG. 4(e) is Western blot results of BTN3A3 expression in the various colorectal carcinoma cell lines.

The results of flow cytometry analysis of BTN3A expression level in patients with breast cancer were shown in FIG. 3(a): breast cancer tumor cells defined by CD45$^-$, cells labeled with anti-CD277 antibody were used as the experimental group to express BTN3A, and the control group was cell labeled with isotype control antibody.

3. Detection of Tumor Cell BTN3A Expression Level in Tumor Tissues of Patients with Lung Cancer According to the above description, the expression level of tumor cell BTN3A in tumor tissues of patients with lung cancer was detected.

The results of flow cytometry analysis of BTN3A expression level were shown in FIG. 3(b): lung cancer tumor cells defined by CD45$^-$, cells labeled with anti-CD277 antibody were used as the experimental group to express BTN3A, and the control group was cell labeled with isotype control antibody.

4. Detection of Tumor Cell BTN3A Expression Level in Tumor Tissues of Patients with Colorectal Cancer According to the above description, the expression level of tumor cell BTN3A in tumor tissues of patients with colorectal cancer was detected.

The results of flow cytometry analysis of BTN3A expression level were shown in FIG. 3(c): colorectal cancer tumor cells defined by CD45$^-$, cells labeled with anti-CD277 antibody were used as the experimental group to express BTN3A, and the control group was cell labeled with isotype control antibody.

5. Detection of Tumor Cell BTN3A Expression Level in Tumor Tissues of Patients with Giant-Cell Tumor According to the above description, the expression level of tumor cell BTN3A in tumor tissues of patients with giant-cell tumor was detected.

The results of flow cytometry analysis of BTN3A expression level were shown in FIG. 3(d): giant-cell tumor cells defined by CD45$^-$, cells labeled with anti-CD277 antibody were used as the experimental group to express BTN3A, and the control group was cell labeled with isotype control antibody.

6. Detection of Tumor Cell BTN3A Expression Level in Tumor Tissues of Patients with Renal Cancer According to the above description, the expression level of tumor cell BTN3A in tumor tissues of patients with renal cancer was detected.

The results of flow cytometry analysis of BTN3A expression level were shown in FIG. 3(e): renal cancer tumor cells defined by CD45$^-$, cells labeled with anti-CD277 antibody were used as the experimental group to express BTN3A, and the control group was cell labeled with isotype control antibody.

7. Detection of Tumor Cell BTN3A Expression Level in Tumor Tissues of Patients with Parotid Gland Cancer According to the above description, the expression level of tumor cell BTN3A in tumor tissues of patients with parotid gland cancer was detected.

The results of flow cytometry analysis of BTN3A expression level were shown in FIG. 3(f): parotid gland cancer tumor cells defined by CD45$^-$, cells labeled with anti-CD277 antibody were used as the experimental group to express BTN3A, and the control group was cell labeled with isotype control antibody, Example 5

Various Tumor Cell Lines Express BTN3A3

1. The culture of tumor cell lines

Culturing he following breast cancer cell lines: MCF7 (3111C0001CCC000013), ZR75-1 (3111C0001CCC000090), BT474(3111C0001CCC000129), T47D(3111C0001CCC000265), MDA-MB-453 (3111C0001CCC000016), SKBR3 (3111C0001CCC000085), MDA-MB-468 (3111C0001CCC000249), MDA-MB-436 (3111C0001CCC000352) MDA-MB-231 (3111C0001CCC000013); the following liver cancer cell lines: BEL -7402(3131C0001000700010), HepG2 (3111C0001CCC 000035), HCC-LM3 (3142C0001000000316), HHCC(3111C 0002000000069), Hep3B(3111C0001CCC 000376), QGY7701 (3131C0001000700042), SMCC7721 (3111C0001CCC000087), Huh7(3131C0001000700182); the following melanoma cell lines: A875 (3111C0001CCC000094), A375(3131C0001000700004); the following gastric cancer cell lines: MKN28 (3111C0001CCC000482), NCI-N87 (3111C0001CCC000481), MGC-803(311 C0001CCC000227), SGC-7901(3131C0001000700046); the following colorectal cancer cell lines LOVO (3111C0001CCC000164), SW480(3142C0001000000064), LS174T(3111C0001CCC000248), DLD-1 (3131C0001000700134). The above cells were purchased from the National Experimental Cell Resource Sharing Platform. The above cell culture conditions were cultured according to the method on the website of the "National Experimental Cell Resource Sharing Platform".

2. Each of the above cell lines was lysed with RIPA lysate (Thermofisher, 89901) to obtain cell lysates, and the cell lysate was subjected to Western Blot detection, and the expression level of BTN3A3 was detected by anti-BTN3A3 antibody (Sigma, HPA007904).

Western Blot results were shown in FIGS. 4(a)-(e): As can be seen from the Figures, various tumor cell lines express BTN3A3.

Example 6

Expression of BTN3A2 and BTN3A3 on Breast Cancer Cells

I. OCR Detection of BTN3A2 and BTN3A3 Expression Levels on Breast Cancer Cell Lines
1. RNA Extraction and Reverse Transcription of cDNA The RNA extract kit was used to extract RNA from the following breast cancer cells: MCF7, ZR75-I, BT474, T47D, SKBR3, MDA-MB-468, MDA-MB-231, MDA-MB-436, and according to the method of cDNA synthesis kit to synthesize cDNA.

2. qPCR Detection of BTN3A3 Expression Level on Breast Cancer Cell Lines

Using the cDNA obtained in step 1 as a template, BTN3A2, BTN3A3 and GAPDH were amplified using a realtime fluorescent quantitative nucleic acid amplification detection system (qPCR), and the relative expression levels of BTN3A2 and BTN3A3 were analyzed by software. The above BTN3A2, BTN3A3 and GAPDH primers were purchased from Qiagen.

The result was shown in FIG. 5(a). The results of qPCR detection showed that BTN3A2 and BTN3A3 were highly expressed on breast cancer cells MDA-MB-231, MDA-MB-468 and MDA-MB-436.

II. Flow Cytometry Shows that BTN3A Molecules were Expressed on the Surface of Breast Cancer Cells The anti-CD277 antibody (which simultaneously recognizes BTN3A1, BTN3A2, BTN3A3 in membrane form) was used to flow detect the following breast cancer cell lines: MCF7, ZR75-1, BT474, MDA-MB-468, MDA-MB-231, MDA-MB- 436. The specific steps were as follows: the experimental group diluted anti-CD277 antibody (eBioscience, 14-2779) in a volume ratio of 1:50 with 1×PBS, and the control group diluted the isotype control antibody (eBioscience, 14-4714-82) in a volume ratio of 1:50 with 1×PBS, and both incubated for 30 min at 4° C. After washing the cells 3 times with 1×PBS, the supernatant was discarded. The cells were labeled with goat anti-mouse PE-labeled fluorescent secondary antibody (Biolegend, 405307) which was diluted at a ratio of 1:50 and incubated for 30 min at 4° C. After washing the cells 3 times with 1×PBS, the supernatant was discarded. The residuum was resuspended in 300 μl of PBS, and subjected to flow detection.

The results were shown in FIG. 5(b). It could be seen from the figure that BTN3A was expressed on the surface of breast cancer cells MDA-MB-468, MDA-MB-231 and MDA-MB-436.

III. Cellular Immunofluorescence Detection Shows that BTN3A3 Localized to the Breast Cancer Cell Surface Membrane MDA-MB-231 cells in the cultured state were collected, washed three times with PBS, and excess serum was washed away. Diluted a 10×permeabilizing solution (Dakko, 421002) into a 1×working solution. The cells were resuspended in the permeabilizing solution and centrifuged at 350 g for 10 min, and then the supernatant was discarded. The procedure was repeated once. The cells immobilized and ruptured membrane were resuspended by 100 ul permeabilizing solution, and incubated with anti-BTN3A3 antibody (Sigma, HPA007904) which was diluted in volume ratio of 1:200 with the permeabilizing solution at 4° C. for 30 min. After washing the cells three times with the permeabilized solution, the supernatant was discarded. Rabbit TRITC fluorescent antibody (Zhongsu Jinqiao, ZF-0318) diluted in a volume ratio of 1:200 was added and incubated at 4° C. for 30 min in the dark. After washing the cells three times with the permeabilized solution, the cells were placed in a glass slide, and the expression of BTN3A3 was observed under a fluorescence microscope.

The results were shown in FIG. 5(c). It can be seen from the figure that MDA-MB-231 cells expressed BTN3A3, which mainly localized to the cell membrane.

Example 7

BTN3A2 and BTN3A3 Expressed by Tumor Cells Promote Tumor Formation

The effect of tumor-expressed BTN3A3 on tumor progression was verified using 231-NC cell and 231-sh4 cell. The specific steps were as follows:
1. Construction of Human Breast Cancer Cell MDA-MB-231 with BTN3A3-Knockdown Both 231-sh3 cell and 231-sh4 cell were human breast cancer cells MDA-MB-231, which stably expressed green fluorescent protein and knocked down BTN3A3. 231-NC cell was human breast cancer cell MDA-MB-231, which stably expressed green fluorescent protein. The specific construction steps were as follows:

(1) Entrust the company of Suzhou Jima to complete the steps of construction of sh expression plasmid with BTN3A3-knockdown, and packaging and purification of the lentivirus. The sh RNA sequence was as follows: sh3: GCCACAGATGGArCTCANATC (SEQ ID NO: 4); sh4: CCCTTCTGCCAACCAATCA (SEQ ID NO: 5); NC (negative control sequence): TTCTCCGAACGTGTCACGTTTC (SEQ ID NO: 21).

(2) The constructed sh3 expression plasmid was transfected into the target cell (human breast cancer cell MDA-MB-231) by lentivirus, and screened by fluorescent protein to obtain a stable cell line 231-sh3 with BTN3A3-knockdown.

The constructed sh4 expression plasmid was transfected into the target cell (human breast cancer cell MDAMB-231) by lentivirus, and screened by fluorescent protein to obtain a stable cell line 231-sh4 with BTN3A3-knockdown.

The constructed NC expression plasmid was transfected into the target cell (human breast cancer cell MDA-MB-231) by lentivirus, and screened by fluorescent protein to obtain a control cell line 231-NC.

The specific procedure for the above transfection was as follows: 18-24 hours before virus transfection, adherent cells were plated into 24-well plates at 1×10$^5$ cells/well. The number of cells were about 2×10$^5$ MOI/well when transfected with lentivirus. On the next day, the original medium was replaced with 2 ml of fresh medium containing 6 μg/ml of polybrene (Suzhou Jima), and an appropriate amount of virus suspension was added. The culture was continued for 24 hours, and the virus-containing medium was replaced with fresh medium, Significant fluorescence was observed after 48 hours of viral infection, which was more pronounced after 72 hours. The culture was expanded for one week, and cells with GFP were obtained by flow sorting.

(3) Detection the mRNA Expression Level of BTN3A2 and BTN3A3

$10^5$ 231-sh4 cells and 231-NC control cells were collected, and the expression levels of BTN3A1, BTN3A2 and BTN3A3 mRNA in 231-sh4 cells and 231-NC control cells were detected by qPCR. The specific steps were as follows: RNA extraction and reverse transcription were according to the method described in the kit instructions, and the obtained cDNA was subjected to qPCR using qPCR primers. Wherein, the RNA Mini Kit (74034) was purchased from Qiagen. The RNA Reverse Transcription Kit (Promega) was purchased from Promega. BTN3A1 (QF00264803), BTN3A2 (QT00060039), BTN3A3 (QF00264803) gene OCR primers were purchased from Qiagen.

Figures 6A, 6B, 6C:
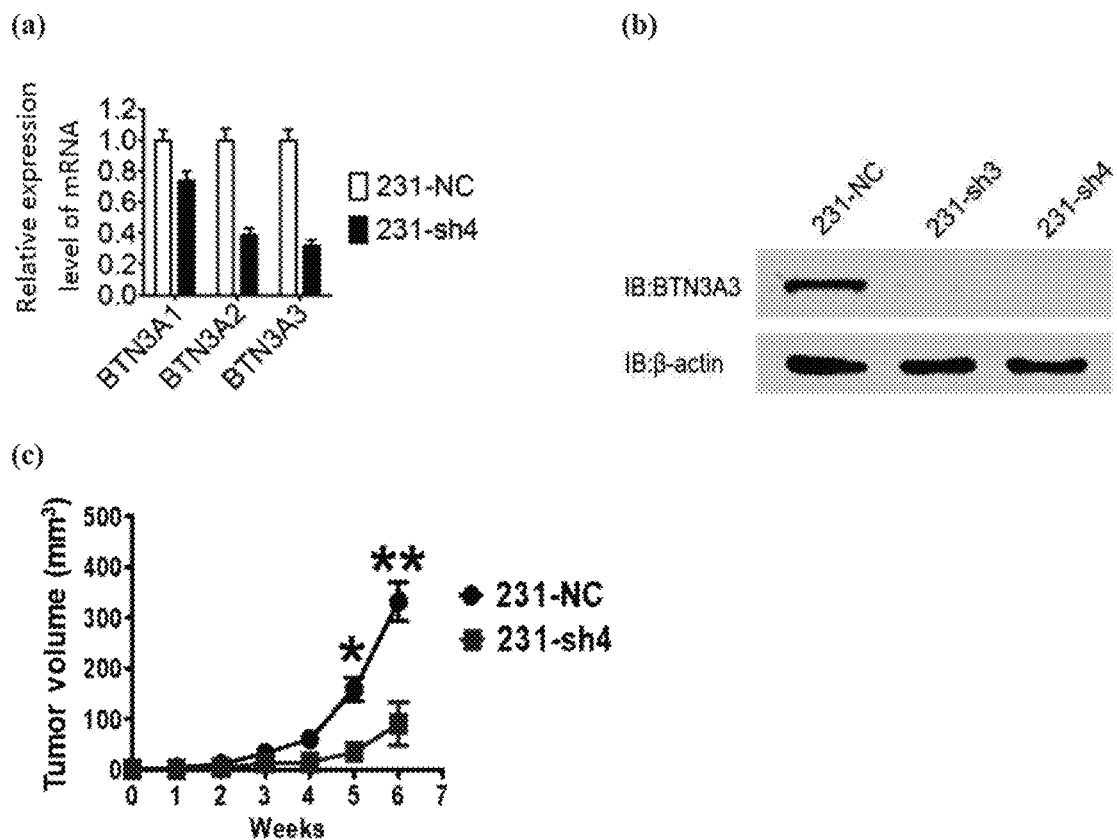
FIG. 6(a) is a histogram of OCR detection of BTN3A2 and BTN3A3, showing the knockdown of BTN3A2 and BTN3A3 by shRNA.
FIG. 6(b) is Western blot results of BTN3A3 expression level, showing the effect of shRNA knockdown on the expression of BTN3A3.
FIG. 6(c) is the detection result curves of tumor growth in human breast cancer xenografts in nude mice, showing a tumor volume comparison of 231-NC and 231-sh4.

The results were shown in FIG. 6(a). Compared with the control cell 231-NC, the relative expression levels of BTN3A2 and BTN3A3 in the stable cell line 231-sh4 with BTN3A3-knockdown were lower than 0.4, indicating that expression levels of BTN3A2 and BTN3A3 in the stable cell line 231-sh4 with BTN3A3-knockdown were significantly decreased.

(4) Detection of Protein Level Expression of BTN3A3

$10^5$ 231-sh3 cells, 231-sh4 cells and 231-NC control cells were separately collected, and BTN3A3 protein level expression was detected in 231-sh3 cells, 231-sh4 cells and 231-NC control cells. The specific steps were as follows: RIPA lysate (Thermofisher, 89901) was used to lyse the above each cell line, to obtain cell lysate, respectively, and the cell lysate was detected by Western Blot, and the BTN3A3 expression level was detected by anti-BTN3A3 antibody (Sigma, HPA007904). The specific method refers to the antibody specification.

The results were shown in FIG. 6(b). Compared with the control cell 231-NC, the expression level of BTN3A3 in the stable cell line 231-sh3 with BTN3A3- knockdown and the stable cell line 231-sh4 with BTN3A3-knockdown were significantly decreased.

2. Control cells 231-NC and 231-sh4 cells were implanted in situ in mammary fat pads of nude mice at 1000 cells/one mouse. After inoculation of the cells, observation was started on the 8th day, and then observed once a week, and the long diameter a and the short diameter b of the mouse tumor were respectively measured using a vernier caliper, and the tumor volume and the tumor formation rate were calculated. The tumor volume calculation formula is 0.5× $ab^2$. The mice were sacrificed until 6 weeks.

The results of tumor volume were shown in FIG. 6(c). At the 0th, 1th, 2th, 3th, 4th, 5th, and 6th week after inoculation, the tumor volumes of 231-NC cells were 0.000±0.000, 3.398±5.829, 10.627±10.152, 32.637±20.258, 60.116±24.670, 158.550±59.933 and 331.362±100.745 (respectively; at the 0th, 1th, 2th, 3th, 4th, 5th, and 6th week after inoculation, the tumor volumes of 231-sh4 cells were 0.000±0.000, 0.000±0.000, 4.068±6.957, 14.460±20.532, 13.208±17.609, 36.183±48.657 and 96.543±127.005 (mm$^3$).

The results of the tumor formation rate were shown in Table 2. The tumor formation rate of the control cells 231-NC group was significantly higher than that of the 231-sh4 group.

TABLE 2 the detection result of tumor formation rate

| Group | Mouse Number with Tumor/ Total Mouse Number | Tumor Formation Rate (%) |
|---|---|---|
| 231-NC | 5/10 | 50 |
| 231-sh4 | 2/10 | 20 |

All the above results indicated that the tumor formation rate and tumor formation volume of breast cancer cells in nude mice decreased significantly after knocking down BTN3A2 and BTN3A3. This indicated that BTN3A2 and BTN3A3 promote tumor formation.

Example 8

Direct and Specific Interaction Exists Between LSECtin and BTN3A2 and BTN3A3

Adhesion experiments verified that direct and specific interaction existed between LSECtin and BTN3A2 and BTN3A3.

1. Construction of Vectors Overexpressing BTN3A1, BTN3A2, BTN3A3

Using the BTN3A1 sequence (SEQ ID NO: 6), BTN3A2 sequence (SEQ ID NO: 7), and BTN3A3 sequence (SEQ ID NO: 8) to substitute the DNA fragments between the NdeI and XhoI cleavage sites of the pIRES2-EGFP vector (Clotech, 6029-1), respectively, the vector pIRES2-EGFP-BTN3A1 expressing BTN3A1, pIRES2-EGFP-BTN3A2 expressing BTN3A2, and pIRES2-EGFP-BTN3A3 expressing BTN3A3 were obtained, respectively.

2. BTN3A1-expressing vector pIRES2-EGFP-BTN3A1, BTN3A2-expressing pIRES2-EGFP-BTN3A2, BTN3A3-expressing pIRES2-EGFP-BTN3A3 and empty vector pIRES2-EGFP were transfected into BT474 cells (National Experimental Cell Resource Sharing Platform, 3111C0001CCC000129), respectively. After transfection for 36 h, BT474-BTN3A1 overexpressing BTN3A1, BT474-BTN3A2 overexpressing BTN3A2, BT474-BTN3A3 overexpressing BTN3A3, and BT474-EGFP overexpressing empty vector were obtained.

3. Each cell in the step 2 was obtained by digestion and collection, and then was adhered to human LSECtin protein (R&D, 2947-CL) and mouse LSECtin-Fc protein, respectively, and the human LSECtin adhesion rate was detected by mouse anti-human LSECtin antibody CCB059. The adhesion rate of the murine, and the mouse LSECtin adhesion rate was detected by anti-IgG (Biolegend, 405307), and the adhesion ratio was detected by flow cytometry. Details of adhesion assay have been published in the method of "Tang L, Yang J, Tang X, et al. The DC-SIGN family member LSECtin is a novel ligand of CD44 on activated T cells[J], European journal of immunology. 2010, 40(4): 1185-1191".

Figures 7A, 7B:
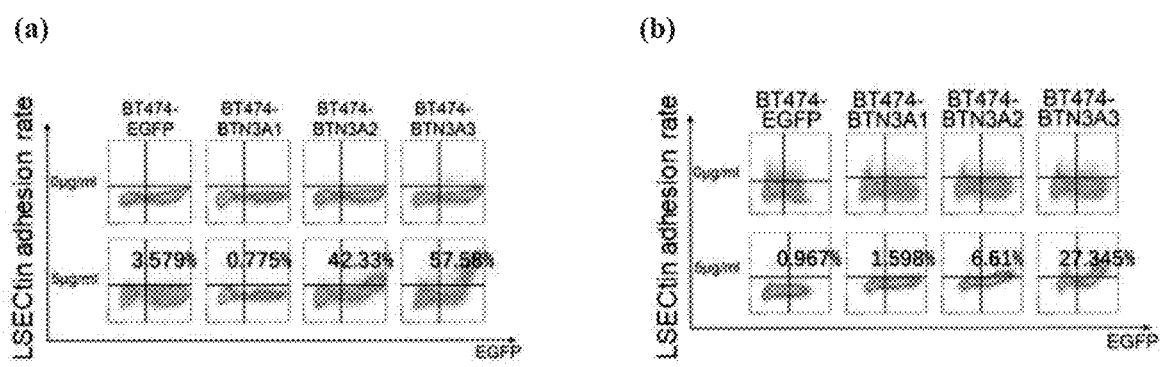
FIG. 7(a) is an adhesion scatter diagram of human LSECtin and BTN3A3 expressed by tumor cell by the flow cytometric analysis, showing direct and specific interaction exist between human recombinant protein LSECtin and BTN3A3.
FIG. 7(b) is an adhesion scatter diagram of murine LSECtin and BTN3A3 expressed by tumor cell by the flow cytometric analysis, showing direct and specific interaction exist between murine LSECtin and BTN3A3.

The results of adhesion experiments which verified that direct and specific interactions existed between LSECtin and BTN3A3 were shown in FIGS. 7(a) and 7(b). Wherein, the human LSECtin adhesion results were shown in FIG. 7(a), LSECtin did not adhere to the cell BT474-EGFP overexpressing the empty vector (adhesion rate was 3.579%), and the cell BT474-BTN3A1 overexpressing BTN3A1 (adhesion rate was 0.775%), and weakly adhered to the cell BT474-BTN3A2 overexpressing BTN3A2 (adhesion rate was 42.33%), strongly adhered to the cell BT474-BTN3A3 overexpressing BTN3A3 (adhesion rate was 57.587%). The results of murine LSECtin-Fc adhesion were shown in FIG. 7(b). LSECtin did not adhere to the cell BT474-EGFP overexpressing the empty vector (adhesion rate was 0.967%), and the cell BT474-BTN3A1 overexpressing BTN3A1, and the cell BT474-BTN3A2 overexpressing BTN3A2 (adhesion rate was 6.61%), and adhered to BT474-BTN3A3 (adhesion rate was 27.345%).These results indicated that there was a direct and specific strong interaction between human and murine LSECtin and BTN3A3 expressed on the surface of human tumor cells. Human LSECtin had strong interaction with BTN3A3 expressed on the surface of human tumor cells.

Example 9

Interactions of LSECtin with BTN3A2 and BTN3A3 Promote Maintance of Tumor Cell Sternness I. Sphere-formation experiments prove that interactions of LSECtin with BTN3A2 and BTN3A3 promote maintance of tumor cell sternness.

In this example, the sphere-formation experiment proved that the interaction of LSECtin BTN3A2 and BTN3A3 promoted the maintenance of tumor cell sternness. The specific steps were as follows:

1. 231-sh3 cell, 231-sh4 cell and 231-NC cell, and BT474-BTN3A1 cell overexpressing BTN3A1, BT474-BTN3A2 cell overexpressing BTN3A2, BT474-BTN3A3 cell overexpressing BTN3A3, and BT474-EGFP cell overexpressing the empty vector obtained from 2 in the step 2 of Example 7 were made into a single cell suspension, and the first generation cells were plated at 20,000/mL, and passaged at 1.000/m L.

2. Mixing each of the above cells, B27 (Life, 17504044), bFGF (Sigam, SRP2092), EGF (Sigma, E9644), insulin (Sigma, I3536), heparin (sigma, 1228553) and DMEM/F12 serum-free medium to obtain the culture system separately, and the concentration of each component in the culture system was: B27 (10 ng/ml), bFGF (20 ng/ml), EGF (20 ng/ml), insulin (5 µg/ml), heparin (4 µg/ml). After 7-10 days of culture, the number of spheres which were larger than 75 µm in diameter was calculated and pictures were taken.

3. The spheres were collected by centrifugation at 800 rpm, digested with trypsin (Gibico, 25300120), and filtered through a 40 µm sieve to perform a secondary sphere formation experiment.

4. LSECitn-stimulated tumor cells were added to each of the above culture systems at a concentration of 100 ng/ml, and each cell after stimulation with LSECitn was obtained.

The results were shown in FIG. 8(a) and FIG. 8(b). At 100 ng of LSECtin stimulation concentration, LSECtin was able to promote the sphere-formation of control cell 231-NC. At 100 ng of LSECtin stimulation concentration, LSECtin wasn't able to promote the sphere-formation of cell BT474-EGFP overexpressing the empty vector, but it was able to promote the sphere-formation of cell BT474-BTN3A2 overexpressing BTN3A2 and cell BT474-BTN3A3 overexpressing BTN3A3.

II. Detection of Sternness Characteristic Molecular Expression Levels

The 231-sh4 cells and 231-NC cells in the sphere formation experiment obtained in the fourth step of step 1 were collected, and the expression changes of the tumor sternness-related characteristic molecules such as OCT4, NANOG, and SOX2 of the breast tumor were detected by qPCR. DC-SIGN represented a negative control, Control was a non-LSECtin-stimulated group, 231-sh4 was a cell that knocked down BTN3A3, and 231-NC was a control cell. The primer sequences were as follows:

```
OCT4:
                                 (SEQ ID NO: 22)
    Up-GCTCGAGAAGGATGTGGTCC;

(SEQ ID NO: 23)
    Down-GTTGTGCATAGTCGCTGCT;

NANOG:
                                 (SEQ ID NO: 24)
    Up-TCTGGACACTGGCTGAATCCT;

(SEQ ID NO: 25)
    Down-CGCTGATTAGGCTCCAACCATT;

SOX2:
                                 (SEQ ID NO: 26)
    Up-GCTCGCAGACCTACATGAAC;

(SEQ ID NO: 27)
    Down-GGGAGGAAGAGGTAACCACA.
```

The results were as shown in FIG. 8(c). At 100 ng of LSECtin stimulation concentration, LSECtin was able to promote the expression of the sternness key transcription factors Oct4, Nanog and Sox; however, these promotion effects were obtained after knocking out BTN3A3, otherwise could't.

The above results indicated that the interactions of LSECtin with BTN3A2 and BTN3A3 promoted tumor progression dependence and promoted the maintenance of tumor cell sternness.

Example 10

Interactions of LSECtin with BTN3A2 and BTN3A3 Promote Tumor Progression, Which Depends on Activation of STAT3 Phosphorylation in Tumor Cells I. LSECtin Stimulates STAT3 Phosphorylation in Breast Cancer Cells Expressing BTN3A3

The LSECtin-stimulated spheres obtained in the 4 of the step 1 in Example 8 were separately collected to form samples: 231-sh3 cell with BTN3A3-knockdown (LSECitn-231-sh3), 231-sh4 cell with BTN3A3-knockdown (LSECitn-231-sh4), 231-NC cell (LSECitn-231-NC) and the non-LSECtin-stimulated spheres obtained in 3 of the step 1 in Example 8 were separately collected to form samples: 231-sh3 cell with BTN3A3-knockdown (231-sh3), 231-sh4 cell with BTN3A3-knockdown (231-sh4), 231-NC cell (231-NC). After digestion with trypsin, centrifugation at 1000 rpm at 4° C., the supernatant was discarded, the cells were collected, and the cells were washed three times with PBS. The cells were lysed on ice by RIPA lysate for 30 min, centrifuged at 12,000 rpm, and the supernatant was taken to obtain a cell lysate. The background levels of STAT1, STAT3, STAT5, and STAT6 in the lysates were detected by Western blotting using the Stat Antibody Sampler Kit (Cell signaling technology, 9939). The Phosphorylation levels of STAT1, STAT3, STAT5, and STAT6 in the lysates were detected by Phospho-Stat Antibody Sampler Kit (Cell signaling technology, 9914). The specific detection methods were according to the instructions in the kits.

The results were shown in FIG. 9(a). Under the stimulation of LSECtin, the p-STAT3 levels of 231-NC cells expressing BTN3A2 and BTN3A3 normally were significantly up-regulated, but in the 231-sh3 cells with BTN3A2-knockdown and BTN3A3-knockdown (LSECitn-231-sh3), and in the 231-sh4 cells with BTN3A2-knockdown and BTN3A3-knockdown (LSECitn-231-sh4), LSECtin could not stimulate the up-regulation of p-STAT3 levels; but whether or not the BTN3A3 was knocked down, the phosphorylation levels of other molecule such as STAT1, STAT5, and STAT6 in STAT family did not upregulate.

The above results indicated that LSECtin was able to stimulate the up-regulation of p-STAT3 levels by interacting with BTN3A3.

II. LSECtin promote the sphere-formation of breast cancer cells expressing BTN3A2 and BTN3A3, which depends on the STAT3 phosphorylation.

The following sphere-formation samples obtained from the fourth step of the step 1 in Example 8 were separately collected: cells 231-sh3 with BTN3A3-knockdown, cells 231-sh4 with BTN3A3-knockdown, and cells 231-NC with BTN3A3-knockdown. The STAT3 inhibitor (selleck, S1155) was added after collecting samples for three days and the number of sphere-formation was measured on the tenth day.

The results were shown in FIG. 9(b). After the addition of STAT3 inhibitor, the ability of LSECtin promoting the sphere-formation of 231-NC cells expressing BTN3A2 and BTN3A3 normally was significantly descended. In the 231-sh3 and 231-sh4 cells with BTN3A2-knockdown and BTN3A3-knockdown, the addition of a STAT3 inhibitor completely prevented the LSECtin from promoting the sphere-formation.

The above results indicated that the interaction of LSECtin with BTN3A2 and BTN3A3 expressed by breast cancer cells promoted tumor progression, which depended on the level of STAT3 phosphorylation inside the cell.

It was proved by the above Example 1-Example 10 that LSECtin expressed by tumor-associated macrophages and BTN3A2 and/or BNT3A3 expressed by tumor cells promote tumor progression by promoting the maintenance of tumor cell sternness, which was embodied in promoting tumor cell sphere-formation, the expression of sternness transcription factors and the promotion of tumor progression in mouse tumor models, indicating that LSECtin expressed by tumor-associated macrophages and BNT3A3 expressed by tumors were able to be used as targets for tumor immunotherapy, respectively. The common characteristic of these tumors was that they could infiltrate LSECtin expressed by tumor-associated macrophages:

In the above examples, the LSECtin was a protein consisting of the amino acid sequence shown in SEQ ID NO: 1 in the Sequence Listing; or a protein derived from SEQ ID NO: 1, which was obtained by substituting and/or deleting and/or adding one or more amino acid residues in the amino acid sequence of SEQ ID NO: 1 and had the same function. BTN3A2 was a protein consisting of the amino acid sequence shown in SEQ ID NO: 2 in the Sequence Listing; or a protein derived from SEQ ID NO: 2, which was obtained by substituting and/or deleting and/or adding one or more amino acid residues in the amino acid sequence of SEQ ID NO: 2 and had the same function. BTN3A3 was a protein consisting of the amino acid sequence shown in SEQ ID NO: 3 in the Sequence Listing; or a protein derived from SEQ ID NO: 3, which was obtained by substituting and/or deleting and/or adding one or more amino acid residues in the amino acid sequence of SEQ ID NO: 3 and had the same function.

The above examples also demonstrated that inhibition of interaction of LSECtin with BTN3A2 and/or BTN3A3 could effectively slow tumor progression, which was reflected in reducing tumor incidence and slowing tumor volume growth, thus suggesting that LSECtin and BTN3A3 were able to be used together as targets for immunotherapy of tumor in which tumor-associated macrophages expressed LSECtin and tumor cells expressed BTN3A3. These tumors included but not limited to breast cancer, myeloma, liver cancer, gastric cancer, colon cancer, lung cancer, giant cell tumor of bone, kidney cancer, larynx cancer or parotid cancer.

According to the results that interactions between LSECtin and BTN3A2 or interactions between LSECtin and BTN3A3promoted tumor progression, the present invent further proposed substance to inhibit the interactions between LSECtin and BTN3A2 or the interactions between LSECtin and BTN3A3. These substance were the products having at least anyone of the function described in (b1)-(b5) below:

(b1) treating tumor and/or preventing tumor;
(b2) inhibiting tumor progression;
(b3) inhibiting the maintenance or promotion of tumor cell sternness;
(b4) inhibiting the expression of tumor cell sternness-related characteristic molecules; and
(b5) inhibiting STAT3 phosphorylation in the tumor cells.

Here, the substance to inhibit the interactions between LSECtin and BTN3A2 or the interactions between LSECtin and BTN3A3 were anyone of the followings: RNA molecules that interfere with BTN3A2 and BTN3A3 expression, anti-LSECtin antibody, small molecule inhibitor of LSECtin, LSECtin soluble protein, RNA molecules that interfere with LSECtin expression, anti-BTN3A2 antibody, small molecule inhibitor of BTN3A2, BTN3A2 soluble protein, RNA molecules that interfere with BTN3A2 expression, anti-BTN3A3 antibody, small molecule inhibitor of BTN3A3, BTN3A3 soluble protein and RNA molecules that interfere woth BTN3A3 expression. Wherein, The RNA molecule that interferes with BTN3A2. and BTN3A3 expression or the RNA molecules that interferes with BTN3A3 expression was the shRNA molecule shown in SEQ ID NO: 4 or the nucleotide obtained by deleting or adding or changing one or more nucleotides in SEQ ID NO: 4, and having the same function with sequence 4; or the shRNA molecule shown in SEQ ID NO: 5 or the nucleotide obtained by deleting or adding or changing one or more nucleotides in SEQ ID NO: 5. and having the same function with SEQ ID NO: 5.

Hereinafter, the substance capable of inhibiting the interaction between LSECtin and BTN3A3 will be specifically described by way of examples. Example 11-Example 18 was described in detail for the fusion protein BTN3A3-Ig which was able to block the interaction of LSECtin with BTN3A3.

Example 11

Expression of Fusion Protein BTN3A3-Ig

The substance to block the interaction between LSECtin and BTN3A3 was fusion protein BTN3A3-Ig, and the expression method thereof comprises the following steps:

1) Construction of the fusion gene BTN3A3-Ig: BTN3A3 extracellular domain protein (in this example, considering that LSECtin interacted with the extracellular domain of BTN3A3, the protein that blocked its interaction needed to compete with the membrane form BTN3A for binding to LSECtin, so BTN3A3 extracellular domain protein was selected) was selected based on the human BTN3A3 gene sequence (GenBank No.: BT007251.1) and human IgG1 gene sequence (GenBank No.: AY623427.1) searched in the gene bank. Then the appropriate linker coding sequence was selected, and fusion gene BTN3A3-1g was obtained by artificial synthesis. The fusion gene BTN3A3-Ig had a nucleotide sequence as shown in SEQ ID NO: 10 in the Sequence Listing, and the 1-1470 bp from the N-terminus was the coded sequence of the amino acid sequence of SEQ ID NO: 9 in the Sequence Listing. The 48-786 bp from the N-terminus was human BTN3A3-coding sequence. The 787-798 bp from the N-terminus was the linker sequence. The 799-1470 bp from the N-terminus was the human IgG-coding sequence.

2) Construction of recombinant expression vector: the fusion gene BTN3A3-Ig was ligated between the NheI and SalI cleavage sites of the vector pIRES2-EGFP (purchased from Clotech) to obtain the recombinant expression vector pIRES2-EGFP-BTN3A3-Ig.

3) Expression of the fusion protein BTN3A3-Ig: The recombinant expression vector pIRES2-EGFP-BTN3A3-Ig containing the fusion gene BTN3A3-Ig was transfected into 293T cells (derived from the National Experimental Cell Resource Sharing Platform), and serum-free medium M293TI (purchased from Beijing Yiqiao Shenzhou Technology Co., Ltd., filtered with 0.45 µm filter (PN4614, Pall), stored on ice) was used to culture recombinant 293T cells at 37° C. (±0.5° C.). The cell supernatant was collected and the medium was changed every 24 hours until 96 hours (24-120 hours). Ended the culture, and the fusion gene BTN3A3-Ig obtained expression;

4) Purification: Protein G Sepharose column (purchased from Kangwei Century Biotechnology Co., Ltd.) (Protein G agarose gel column, Protein G is a cell surface protein isolated from G or C type Streptococcus, It can bind to most mammalian IgGs by interacting with the Fc region of immunoglobulin (Ig) primarily. Native protein G has albumin and cell surface binding domains. Recombinant Protein G removes albumin and cell surface binding domains to reduce non-specific binding. This protein can be used to purify IgG after coupling with Sepharose.) was used to purify recombinant expression protein. The purification methods were as follows: the culture supernatant of the cell (recombinant 293T cells containing the fusion gene BTN3A3-Ig) was added with equilibration buffer (20 mM PBS, 150 mM NaCl, pH 8.0) to pH 8.0, and the cell supernatant was added into the Protein G Sepharose column that had been equilibrated with equilibration buffer, and washed the column with equilibration buffer, until no impure protein was detected in the effluent. Eluted with elution buffer (0.1 M glycine, pH 3.0) and the effluent was collected, neutralized immediately with neutralizing buffer (1 M Tris.HCl, pH 9.0), and dialyzed against pH 7.2 0.01 mol/L PBS for 72 h to obtain the fusion protein BTN3A3-Ig, which was consistent with the expected results. The amino acid sequence of the fusion protein BTN3A3-Ig was shown in SEQ ID NO: 9 in the Sequence Listing. The SEQ ID NO: 9 was composed of 490 amino acid residues, and the first amino acid from the N-terminus was start codon, the 2-15 amino acid from the N-terminus was the signal peptide, the 16-262 amino acid from the N-terminus was human BTN3A3, the 263-266 amino acid from the N-terminus was the linker and the 267-490 amino acid from the N-terminus was the human IgG1. The samples were measured for OD260 and OD280 on a UV spectrophotometer, and the protein content was calculated using a BCA protein quantification kit (purchased from Kangwei Century Biotechnology Co., Ltd.), and the result was 1 mg/ml, and stored at −80° C., after dispensing.

Example 12

Coomassie Blue Staining and Western Blot Detection of Fusion Protein BTN3A3-Ig

I. Coomassie Blue Staining of Fusion Protein BTN3A3-Ig

The recombinantly expressed BTN3A3-Ig fusion protein sample of Example 11 was collected, and a 10% SDSPAGE gel was prepared and electrophoresed for Coomassie blue staining. The control was a lysate of cells (recombinant 293T cells containing the fusion gene BTN3A3-Ig).

The results of Coomassie brilliant blue staining were shown in FIG. 10. The protein with a molecular weight of about 55 kD was obtained by expression, which was consistent with the expected results.

II. Western Blot Detection of Fusion Protein BTN3A3-Ig

The recombinantly expressed BTN3A3-Ig fusion protein sample of Example 10 was collected, and a 10% SDSPAGE gel was prepared. The sample was electrophoresed, transferred, and blocked with a TBST solution containing 5% skim milk powder, primary antibody incubated with anti-CD277 (the antibody specification indicated that it was able to identify BTN3A3) (purchased from Thermo Scientific), and secondary antibody incubated with Mouse IgG HRP-conjugated Antibody (purchased from R&D, HAF007). The experimental control protein was human IgG (purchased from R&D).

The results of Western Blot detection were shown in FIG. 11. It can be seen that the fusion protein BTN3A3-Ig recombinantly expressed in Example 11 could specifically bind to the anti-human BTN3A3 antibody, while the control protein human IgG could not recognize, indicating that the BTN3A3-Ig protein was able to be obtained in the above protein expression and purification system.

Example 13

Elisa Detects the Binding Activity of Fusion Protein BTN3A3-Ig to LSECtin Protein The plate was coated with LSECtin protein (2947-CL, R&D) at a concentration of 1 µg/mL and at 4° C. overnight. The blocking solution was prepared with PBST at a concentration of 5% skim milk powder, and after washing the plate, 300 µL of blocking solution per well was used to block the plate at room temperature for 2 h. After washing the plate, the fusion protein BTN3A3-Ig was diluted into gradient solutions according to a certain multiple proportion with a concentration of 2 µg/mL as the start concentration, and incubated for 3 h at room temperature. After washing the plate, which was incubated with the primary antibody anti-CD277 (the antibody specification indicates that it can recognize BTN3A3) (purchased from Thermo Scientific) for 40 min. After washing the plate, which was incubated with the secondary antibody Mouse IgG HRP-conjugated. Antibody (purchased from R&D, HAF007). After washing plate, the following procedures were as follows: developing color, terminating, and OD450 reading. The experimental control protein was human IgG.

The results of Elisa assay were shown FIG. 12. It could be seen that LSECtin protein could directly interact with the fusion protein BTN3A3-Ig, while the control protein human IgG could not be recognized by the anti-CD277 antibody. The BTN3A3-Ig antibody exhibited a gradient indicating that the purity of the BTN3A3-Ig protein purified from the above system was good.

Example 14

Adhesion Assay Showing Fusion Protein BTN3A3-Ig Blocks the Interaction Between the LSECtin Protein and the Membrane Form BTN3A3

During the adhesion experiment, the purified fusion protein BTN3A3-Ig and LSECtin protein were mixed at a ratio of 1:1, and BT474 overexpressing BTN3A3 cells BT474-BTN3A3 were incubated, and then the adhesion experiment was conducted. Methods of adhesion experiment had published in: "Tang L, Yang J, Tang X, et al. The DC-SIGN family member LSECtin is a novel ligand of CD44on activated I cells [J]. Tang L, Yang J, Tang X, et al.. The DC-SIGN family member LSECtin is a novel ligand of CD44 on activated T cells[J]. European journal of immunology, 2010, 40(4): 1185-1191). The experimental control protein was human IgG.

The results that the fusion protein BTN3A3-Ig blocked the interaction between LSECtin and BTN3A3 were shown in FIG. 13. The LSECtin adhesion rate was calculated as LSECtin adhesion positive cells/ZSG positive cells. When added to control IgG the adhesion rate of LSECtin to cells overexpressing BTN3A3 was 33.9%, and the formula was 11.5/(11.5+22.4). After adding the fusion protein BTN3A3-Ig, the adhesion rate of LSECtin to cells overexpressing BTN3A3 was only 3.2%, and the formula was 0.969/(0.969+29.3). The results showed that BTN3A3-Ig blocked the interaction between LSECtin and BTN3A3.

Example 15

Fusion Protein BTN3A3-Ig Blocks LSECtin to Promote Tumor Cell Sternness

The B27 (purchased from Life), bFGF (purchased from Sigma), EGF (purchased from Sigma), insulin (purchased from Sigma), heparin (purchased from Sigma), and DMEM/F12 serum-free medium were mixed to obtain a culture system. The concentrations of the each component in the culture system were: B27 (10 ng/mL), bFGF (20 ng/mL), EGF (20 ng/mL), insulin (5 µg/mL), and heparin (4 µg/mL).

The breast cancer cell MDA-MB-231 (derived from the National Experimental Cell Resource Sharing Platform) was made into a single cell suspension, and plated at 20,000 cells/mL, and 100 ng of BTN3A3-Ig, LSECtin+IgG and LSECtin+BTN3A3-Ig were added respectively. The blank was as control, and after the culture of 7-10 days, the number of spheres larger than 75 µm in diameter was calculated and photographed.

The results were shown in FIG. 17. At 100 ng of LSECtin-stimulated concentration, LSECtin promoted the sphere-formation of MDA-MB-231 cells, but did not promote the sphere-formation of MDA-MB-231 cells after the addition of the fusion protein BTN3A3-Ig, indicating fusion protein BTN3A3-Ig blocked LSECtin from promoting tumor cell sternness.

Example 16

Fusion Protein BTN3A3-Ig Inhibits Tumor Progression 10000 human breast cancer cells MDA-MB-231, Matrigel (BD, 354230) and PBS (Hyclone, SH30256.01.) were mixed to obtain a mixture; the mixture was separately planted in the lower mammary gland of 5 weeks female nude mice to establish human breast cancer xenografts in nude mice. Observed once every other week for two months, and the long diameter a and the short diameter h of the mouse tumor were measured using vernier calipers, and the tumor volume and tumor formation rate were calculated. The calculation formula of tumor volume was $0.5 \times ab^2$, and the calculation formula of the tumor formation rate was the number of tumor-formation / total number of models.

One day before the establishment of model by planting cells in nude mice, the nude mice were divided into the following groups according to the different injections:

IgG control group: intraperitoneal injection of IgG (10 µg/mouse)

BTN3A3-Ig group: intraperitoneal injection of BTN3A3-Ig (10 µg mouse)

MDA-MB-231 cells were planted separately into each of the above wild type nude mice. After modeling, the protein was injected intraperitoneally every 3 days, and the inhibitory effect of BTN3A3-Ig on tumor progression was observed by measuring the tumor volume.

The tumor volumes at 1, 2, 3, 4, 5, 6, 7, and 8 weeks after modeling were as follows: The IgG group was 0±0.35, 9,83±9.22, 18.13±12.68, 41.54±26.64, 134.08±66.72, 362.16±186.56, 661.32±359.54, and 1089.43±584.70 ($mm^3$), respectively;

The BTN3A3-Ig group was 0.00±0.00, 3.72±5.15, 4.25±6.01, 6.23±8.53, 30.45±9.44, 71.80±48.32, 125.24±106.49, and 240.17±255.17 ($mm^3$), respectively.

As shown in FIG. 18, the tumor volume of the injected BTN3A3-Ig group was significantly smaller than that of the injected IgG group, indicating that the injection of the fusion protein BTN3A3-Ig could inhibit tumor growth and could be used for the preparation of antitumor drugs and treatment of tumors.

Example 17

Fusion Protein BTN3A3-Ig Inhibiting Tumor Progression Depends on LSECtin

In the following examples, LSECtin$^{+/+}$Nude$^{-/-}$ was wild-type nude mice, and LSECtin$^{-/-}$Nude$^{--}$ was nude mice with LSECtin-knockout. The specific methods to obtain were as follows: mating BALB/c background male nude mouse LSECtin$^{+/+}$Nude$^{-/-}$ (purchased from Vitalius) with BALB/c background female LSECtin$^{+/+}$Nude$^{-/-}$ mouse to obtain LSECtin$^{+/-}$Nude mouse. Mating male LSECtin$^{+/-}$Nude$^{+/-}$ mouse with female LSECtin$^{+/-}$Nude$^{+/-}$ mouse to obtain LSECtin$^{+/+}$Nude$^{-/-}$(LSECtin-expressed wild type nude mouse) and LSECtin$^{-/-}$Nude$^{-/-}$ (LSECtin-knockout nude mouse) by genotype identification from their offspring. The above BALB/c background female LSECtin$^{-/-}$Nude$^{+/+}$ mouse information had been published in "Zuo Y, Ren S, Wang M, et al. Novel roles of liver sinusoidal endothelial cell lectin in colon carcinoma cell adhesion, migration [J] Gut, 2013, 62(8): 1169-1178", and the public can obtain it from the National Proteome Research Center.

MDA-MB-231 cells were planted into the above-mentioned groups of LSECtin-knockout nude mice according to the method of Example 16. After modeling, the protein was injected intraperitoneally every 3 days, and the inhibitory effect of BTN3A3-Ig on tumor progression was observed by measuring the tumor volume.

The tumor volumes at 1, 2, 3, 4, 5, 6, 7, and 8 weeks after modeling were as follows:

The IgG group was 0.00±0.00, 14.08±11.03, 23.89+ 21.31, 66.90±8.90, 143.47±34.76, 240.21±42.42 and 400.47±28.29 (mm³), respectively;

The BTN3A3-Ig group was 0.00±0.00, 9.93±11.47, 28.19±32.63, 52.12±33.41, 100.68±63.98, 199.67±78.36 and 350.12±45.83 (mm³), respectively.

As shown in FIG. 19, in the case where LSECtin was deleted, the fusion protein BTN3A3-Ig could not exert an effect of inhibiting tumor growth, and therefore BTN3A3-Ig exerted an inhibitory effect on tumor growth depending on the LSECtin in the body.

Example 18

The Fusion Protein BTN3A3-Ig Inhibits Tumors without Toxic Side Effects

The model in Example 16 was used for this example. After treatment with the experimental drug IgG or the fusion protein BTN3A3-Ig, the heart, liver, spleen, lung and kidney tissues of the mice were placed in formalin solution and sent to Beijing Jiasi Jiayang for tissue embedding, sectioning, and HE staining.

After the experimental drug action, the tissue sections were as shown in FIG. 20. After intraperitoneal injection of IgG or fusion protein BTN3A3-Ig, the heart, liver, spleen, lung and kidney tissues of the mice were not damaged, and no obvious inflammatory cell infiltration occurred, indicating that the intraperitoneal injection of the fusion protein BTN3A3-Ig had no toxic side effects.

Example 19-Example 26 further provided a substance capable of blocking the interaction between LSECtin and BTN3A3, thereby inhibiting the occurance and progression of tumors (inhibiting tumor progression). This substance was monoclonal antibodies capable of blocking the interaction between LSECtin and BTN3A3 and having an activity of inhibiting tumor progression.

Example 19

Expression of Fusion Protein BTN3A3-mIg

In order to obtain the monoclonal antibody having the activity of inhibiting tumor progression, the present example first obtained an immunogen for preparing the antibody. The immunogen was a specially designed fusion protein, named BIN 3A3-mIg, which was a recombinant protein obtained by ligating human BTN3A3 to mouse IgG2a by a linker peptide.

The expression method of the fusion protein BTN3A3-mIg comprised the following steps:

1) Construction of the fusion gene BTN3A3-mIg: BTN3A3 extracellular domain protein (in the present invention, considering that LSECtin interacted with the extracellular domain of BTN3A3, the protein that blocked its interaction needed to compete with the membrane form BTN3A for binding to LSECtin, so BTN3A3 extracellular domain protein was selected) was selected based on the human BTN3A3 gene sequence (GenBank No.: BT007251.1) and mouse IgG2a gene sequence (GenBank No.: BC018535.1) searched in the gene bank. Then the appropriate linker coding sequence was selected, and fusion gene BTN3A3-mIg was obtained by artificial synthesis. The fusion gene BTN3A3-Ig had a nucleotide sequence as shown in SEQ ID NO: 12 in the Sequence Listing, and the 1-1497 by from the N-terminus was the coded sequence of the amino acid sequence of SEQ ID NO: 11 in the Sequence Listing. The 1-3 bp from 5' terminus was start codon, the 4-45 bp from 5' terminus coded signal peptide, the 46-786 bp from 5' terminus coded human BTN3A3, the 787-798 bp from 5' terminus coded linker peptide, the 799-1494 bp from 5' terminus coded mouse IgG2a, and the 1495-1497 bp from 5 terminus was termination codon.

2) Construction of recombinant expression vector: the fusion gene BTN3A3-mIg was ligated between the NheI and SalI cleavage sites of the vector pIRES2-EGFP (purchased from Clotech) to obtain the recombinant expression vector pIRES2-EGFP-BTN3A3-mIg.

3) Expression of the fusion protein BTN3A3-mIg: The recombinant expression vector pIRES2-EGFP-BTN3A3-mIg containing the fusion gene BTN3A3-mIg was transfected into 293T cells (derived from the National Experimental Cell Resource Sharing Platform), and serum-free medium M293TI (purchased from Beijing Yiqiao Shenzhou Technology Co., Ltd.. filtered with 0.45 μm filter (PN4614, Pall), stored on ice) was used to culture recombinant 293T cells at 37° C. (±0.5° C.). The cell supernatant was collected and the medium was changed every 24 hours until 96 hours (24-120 hours). Ended the culture, and the fusion gene BTN3A3-mIg obtained expression;

4) Purification: Protein G Sepharose column (purchased from Kangwei Century Biotechnology Co., Ltd.) (Protein G agarose gel column, Protein G is a cell surface protein isolated from G or C type Streptococcus, it can bind to most mammalian IgGs by interacting with the Fc region of immunoglobulin (Ig) primarily. Native protein G has albumin and cell surface binding domains. Recombinant Protein G removes albumin and cell surface binding domains to reduce non-specific binding. This protein can be used to purify IgG after coupling with Sepharose.) was used to purify recombinant expression protein. The purification methods were as follows: the culture supernatant of the cell (recombinant 293T cells containing the fusion gene BTN3A3-Ig) was added with equilibration buffer (20 mM PBS, 150 mM NaCl, pH 8.0) to pH 8.0, and the cell supernatant was added into the Protein G Sepharose column that had been equilibrated with equilibration buffer, and washed the column with equilibration buffer, until no impure protein was detected in the effluent. Eluted with elution buffer (0.1 M glycine, pH 3.0) and the effluent was collected, neutralized immediately with neutralizing buffer (1 M Tris HCl, pH 9.0), and dialyzed against pH 7.2 0.01 mol/L PBS for 72 h to obtain the fusion protein BTN3A3-mIg, which was consistent with the expected results. The amino acid sequence of the fusion protein BTN3A3-mIg was shown in SEQ ID NO: 11 in the Sequence Listing. SEQ ID NO:11 was composed of 499 amino acid residues, and the first amino acid from the N-terminus was start codon, the 2-15 amino acid from the N-terminus was the signal peptide, the 16-262 amino acid from the N-terminus was human BTN3A3, the 263-266 amino acid from the N-terminus was the linker and the 267-498 amino acid from the N-terminus was the mouse IgG2a, and the 499 amino acid from the N-terminus was termination codon.

The samples were measured for OD260 and OD280 on a UV spectrophotometer, and the protein content was calculated using a BCA protein quantification kit (purchased from Kangwei Century Biotechnology Co., Ltd.), and the result was 1 mg/ml, and stored at −80° C. after dispensing.

Example 20

Coomassie Blue Staining and Western Blot Detection of Fusion Protein BTN3A3-mIg

I. Coomassie Blue Staining of Fusion Protein BTN3A3-mIg

The recombinantly expressed BIN fusion protein sample of Example 19 was collected, and a 10% SDSPAGE gel was prepared and electrophoresed for Coomassie blue staining. The control was a lysate of cells (recombinant 293T cells containing the fusion gene BTN3A3-mIg).

The results of Coomassie brilliant blue staining were shown in FIG. 21. The protein with a molecular weight of about 55 kD was obtained by expression, which was consistent with the expected results.

II. Western Blot Detection of Fusion Protein BTN3A3-mIg

The recombinantly expressed. BTN3A3-mIg fusion protein sample of Example 19 was collected, and a 10% SDSPAGE gel was prepared. The sample was electrophoresed, transferred, and blocked with a TBST solution containing 5% skim milk powder, primary antibody incubated with anti-human anti-CD277 (purchased from Thermo Fisher), and secondary antibody incubated with Mouse IgG HRP-conjugated Antibody (purchased from R&D, HAF007). The experimental control protein was mouse IgG (purchased from Abcam, ab37355).

The results of Western Blot detection were shown in FIG. 22. It could be seen that the fusion protein BTN3A3-mIg recombinantly expressed in Example 19 could specifically bind to the anti-human BTN3A3 antibody, indicating that the BTN3A3-mIg protein was able to be obtained in the above protein expression and purification system. The fusion protein BTN3A3-mIg could be used as an immunizing antigen for the preparation of BTN3A3 antibody.

Example 21

Obtaintion of a hybridoma Cell Line Anti-P3 (5E08) which Continuously and Stably Secretes Monoclonal Antibody 5E08 which has the Activity of Inhibiting Tumor Progression The method for obtaining the hybridoma cell line anti-P3 (5E08) comprised the following steps:

I. Animal Immunizing

1. Preparation of Antigen

100 μg (50-100 μg of the fusion protein) BTN3A3-mIg was diluted with physiological saline to 0.25 mL (0.25-0.50 mL), and mixed with an equal volume of Freund's complete adjuvant (purchased from Sigma), and stirred, and emulsified.

2. Immunizing Scheme

First immunization: mice were immunized with the fusion protein BTN3A3-mIg as the antigen at a concentration of 400 μg/mL (200-400 μg/mL), the immunization dose was 0.25 mL (0.25-0.50 mL), and the antigen was injected subcutaneously into the back and the neck of the Balb/c healthy female mice (6-8 weeks old, purchased from Beijing Weitong Lihua Experimental Animal Technology Co., Ltd.), and the others were subjected by intraperitoneal injection;

Secondary immunization: 30 days after the first immunization, the immunization method was the same as the first immunization;

Determination of serum titer: 7 days after the second immunization, blood was collected from the tail vein, and serum titer was determined by ELISA;

Strengthened the immunization: 3-4 days before the fusion, strengthened the immunization, without immunization adjuvant, by intraperitoneal injection or tail vein injection, and the immune concentration and immune dose were the same as the first immunization.

3. Elisa Detection of Peripheral Blood and Ascites Titer in Immunized Mice 3.1 The recombinant BTN3A3-his recombinant protein (purchased from Beijing Yiqiao Shenzhou Technology Co., Ltd.) was used to coat an enzyme plate at a concentration of 1 μg/mL, 200 μl/well, overnight (12-16 hours) at 4° C., and washed three times with PBST wash solution;

3.2 Added 150 μL of blocking solution to each well, overnight (12-16 hours) at 4° C., washed 3 times, patted dry, and stored in a refrigerator at 4° C. for use;

3.3 When the titer was detected, the peripheral blood serum or ascites of the immunized mice was diluted based on 4 multiple proportions (dilutions were 500, 2000, 8000, 32000, 128000, 512000, 2048000, 8192000), and the sample was added into the elisa plate coated at 100 μl/well. At the same time, unimmunized mouse and normal IgG were selected as negative control for each plate, and incubated at 37° C. for 30 minutes, washed plate 4 times and patted dry;

3.4 Secondary antibody Mouse IgG HRP-conjugated Antibody (purchased from R&D HAF007) was added, incubated at 37° C. for 40 minutes, washed the plate 8 times, and patted dry;

3.5 Color solution (purchased from Thermo Fisher Company) was added for 10-20 minutes for color development;

3.6 A stop solution (sulphuric acid solution at a concentration of 2 mol/L) was added to terminate the color reaction;

3.7 The $OD_{450}$ nm value was measured, and the detection result was obtained.

By visual comparison, the highest dilution of ascites darker than the negative control was used as the ascites titer.

The ratio of the serum of the immunized mouse to the non-immunized mouse serum was greater than 2 (ie, the $OD_{450}$ nm value was greater than the negative control 2 times as a positive judgment basis), and could be used for preparing hybridoma cells.

II. Fusion and Screening of Hybridoma Cells

1. Preparation of Trophoblast

The Balb/c mice were euthanized by cervical dislocation and immersed in 75% alcohol for 5 minutes, then placed in a clean bench. The mice were placed in a dish with abdomen upwards or fixed on a anatomical plate. Use a pair of tweezers to clip the skin of the mouse's abdomen and cut a small opening with scissors. Be careful not to cut the peritoneum to prevent the peritoneal fluid from flowing out. Then, use the scissors to make a blunt separation on the upper and lower sides, fully expose the peritoneum, and wipe the peritoneum with an alcohol cotton ball to disinfect. Pipette 5 mL of RPMI1640 base medium (purchased from Hyclone), inject into the abdominal cavity of the mouse. Stop the syringe, shake the mouse or repeatedly pump more times, and use the original syringe to withdraw the liquid in the abdominal cavity, and inject the centrifuge tube. Repeat the above steps 3-4 times. Centrifuge at 1000 rpm for 10 minutes, discard the supernatant, and leave the bottom cells for use. The cells were resuspended in 20-50 mL of complete medium (RPMI1640 medium containing 10% FBS, FBS was purchased from Gibico), and then were added dropwise to the plate at 100 μL/well, and placed in a 37° C.; incubator as trophoblast cells for use.

2. Fusion of Spleen Cells with Myeloma Cells 2.1 One mouse of booster immunization was taken and euthanized by cervical dislocation after blood collection from the eye socket. After sterilizing in 75% alcohol, the spleen was taken to prepare spleen cell suspension (cell concentration: $2.5 \times 10^6 - 5.0 \times 10^6$ cells/mL). Transfer to a 50 mL centrifuge tube, add RPMI1640 medium to 30 mL, centrifuge at 1500-2000 rpm for 5 minutes, discard the supernatant, count, and take 1×10⁸ cells for use. Take 2 bottles of myeloma cells (from the national experim ental cell resource sharing platform) with good growth (>95% viable cells). Completely blow down the myeloma cells, transfer to a 50 mL centrifuge tube, add RPMI1640 medium to 30 mL. Centrifuge at 1500-2000 rpm for 5 minutes, discard the supernatant, add RPMI1640 medium to 30 mL, count, and take 1×10⁷ cells for use.

2.2 Splenocytes and Myeloma cells were mixed at a ratio of 10:1 and centrifuged at 2000 rpm for 3 minutes. The supernatant was poured out, and the cell precipitate was bounced into a paste, and placed in a 37° C. water bath. Add 1 ml. of the fusion agent (purchased from Sigma) in 1 minute, stir the cells, and bath for 45 seconds at 37° C. Add 1 mL of RPMI1640 medium 1 minute and stir the cells. Add 5 mL of RPMI1640 medium evert 2 minutes and stir the cells.

2.3 Gently bounce the cells, resuspend the cells by slowly adding HAT medium (purchased from Sigma) to a volume of 40 ml-50 ml, mix gently, and the cells were added to the prepared trophoblast plates in step 1. 80-100 μL (with 10 mL/plate) was added to the plates by volley, which were cultured in a incubator at 37° C. with $CO_2$, and observed.

From the first day after cell fusion, the cells were carefully observed, and the growth state of the cells, the number of hybridoma cells per well, the number of blocks, the presence or absence of contamination of the culture solution, and the trophoblast cells were recorded. After 3-5 days of culture, the culture solution was changed by HAT medium, and after 10 days, the culture solution was changed by HT medium (purchased from Sigma), and after 20 days, the culture solution was changed by RPMI1640 medium for further 48 hours of culture. The supernatant was collected and numbered in the order of arrangement on the cloning plate. For example, 5E08, etc.

3. Screening of Hybridoma Cells Secreting Monoclonal Antibody 5E08 that Specifically Binds to BTN3A3

The cell supernatant was subjected to Elisa detection according to the method in the step 1, and the clone with positive value greater than 1.5 (5E08, etc.)was selected for flow detection, and the specific method was as follows:

3.1 Construction of BTN3A3 Overexpression Vector

The BTN3A3 gene sequence (GenBank No.: BC018535.1, BTN3A3 cDNA full length) was used to replace the DNA fragment between the NheI and SalI cleavage sites in the pIRES2-EGFP vector (purchased from Clotech) to obtain the BTN3A3 overexpression vector, named pIRES2-EGFP-BTN3A3, whose nucleotide sequence was shown in SEQ ID NO: 8 in the Sequence Listing, 3.2 BTN3A3 overexpression vector pIRES2-EGFP-BTN3A3 and pIRES2-EGFP empty vector were transfected into BT474 cells (from the national experim ental cell resource sharing platform). After transfection for 36 h, recombinant cells were obtained: the cell BT474-BTN3A3 overexpressing BTN3A3 and the cell BT474-EGFP overexpressing the pIRES2-EGFP empty vector.

3.3 The recombinant cells obtained in step 3.2 were digested and antibody labeled with mouse IgG (purchased from Thermo Scientific), commercialized BTN3A3 flow antibody (purchased from Thermo Scientific), and monoclonal antibodies (collected in step 2.3) secreted by hybridoma cells. The cells labeled by goat anti-mouse PE-labeled fluorescent secondary antibody (purchased from Biolegend) were diluted at a ratio of 1:50 by volume and incubated at 4° C. for 30 minutes. After washing the cells 3 times with 1×PBS, the supernatant was discarded. Incubated at 4° C. for 30 minutes, and after washing the cells 3 times with 1×PBS, the supernatant was discarded. Resuspended in 300 μL of PBS, and subjected to flow cytometry.

3.4 The hybridoma cell line was subcloned by making the hybridoma cell line into a single cell suspension, diluenting and dropping it into a 96-well plate plated with trophoblast cells so that the number of hybridoma cells per well was not more than one. After 10 days of normal culture, the supernatant was taken for Elisa detection, and the cells in the 5 wells with the highest positive value were subcloned again until five subclones were completed, thereby obtaining a hybridoma cell which continuously and stably secreted the antibody. The results of the assay were shown in FIG. 23, in which the monoclonal antibody 5E08 secreted by the hybridoma cells was able to recognize BTN3A3 expressed on the surface of human tumor cells, indicating that a hybridoma cell secreting a monoclonal antibody 5E08 specifically binding to BTN3A3 was obtained, named anti-P3 (5E08). This cell line had been deposited on Sep. 26, 2017 in the China General Microbiology Culture Collection Center, whose address was: No. 3, yard 1, Beichen West Road, Chaoyang District, Beijing, China. The deposit number was CGMCC No.14723.

Example 22

Characteristic Detection and Purification of Monoclonal Antibody 5E08 Secreted by Hybridoma Canine Anti-P3 (5E08)

1. Preparation of Ascites and Purification of Monoclonal Antibody 5E08

1. Preparation of Ascites

One or two weeks before the inoculation of the hybridoma cell anti-P3 (5E08), the mice were intraperitoneally injected with 0.5 mL of liquid paraffin, and the pretreated mice were used in 2-3 months. The hybridoma cell anti-P3 (5E08) with good culture state was blown down, centrifuged at 1000 rpm for 5 minutes at room temperature, the supernatant was discarded, and the hybridoma cell anti-P3 (5E08) was resuspended and mixed with serum-free RPMI1640 medium, and the concentration of the cells was adjusted to 2×10⁶ cells/mL, and each mouse was intraperitoneally injected with 0.5 mL. 7-12 days after inoculation of hybridoma cell anti-P3 (5E08), the abdomen of the mouse was obviously enlarged. After the abdomen was enlarged to a certain extent, the mice were executed by dislocating cervical vertebrae, and cutted a small mouth on the abdominal cavity. The ascites was collected with a I mL pipette. The ascites extracted was centrifuged at 3000 rpm for 20 minutes, and the supernatant was collected and stored at −20° C. for use.

2. Purification of Monoclonal Antibody 5E08

Monoclonal antibody 5E08 in mouse ascites collected in step 1 was purified using the IgM monoclonal antibody purification kit (purchased from Beijing Boaolong Immunotechnology Co., Ltd.).

3. Identification of Purified Monoclonal Antibody 5E08

The purified monoclonal antibody 5E08 was subjected to flow cytometry as described in Example 3.

The results showed that the monoclonal antibody 5E08 was able to recognize BTN3A3 expressed on the surface of human tumor cells, indicating that the purified monoclonal antibody 5E08 was obtained.

II. The Characteristic Detection of Monoclonal Antibody 5E08

1. Subtype Detection

The 8 microplate wells were coated with BTN3A3-his recombinant protein (purchased from Beijing Yiqiao Shenzhou Technology Co., Ltd.) using PBS buffer, placed at 4° C. for 12 hours, and then washed once with a washing plate machine PBST. Next, 100 μL of hybridoma cell anti-P3 (5E08) culture supernatant was added to each well, incubated at 37° C. for 30 minutes, and then washed 5 times with a washing plate machine PBST. Thereafter, 100 μL of Goat Anti-Mouse Ig (G-1\G2a\G2b\G3\M\A\κ\λ)-HRP secondary antibody (purchased from Beijing Boaolong Immunotechnology Co., Ltd.) was added to each well and incubated at 37° C. After 30 minutes, continue to wash with PBST for 5 times, then add TMB color solution (purchased from Thermo Scientific), and at 37° C. in the dark for color development. The result could be judged in 20 minutes. The blue hole observed by the naked eye was the positive.

The subtype test results showed that the heavy chain of the monoclonal antibody 5E08 secreted by the hybridoma cell anti-P3 (5E08) was IgM, and the light chain was Kappa.

2. Determination of the Variable Region Sequence of Monoclonal Antibody 5E08

The Kingsray Company was commissioned to sequence the variable region of the monoclonal antibody 5E08 secreted by the hybridoma cell anti-P3 (5E08). The results showed that the heavy chain variable region encoding gene of 5E08 had the DNA sequence of SEQ ID NO: 15 in the Sequence Listing, encoding the amino acid sequence shown in SEQ ID NO: 13 in the Sequence Listing; the light chain variable region encoding gene had the DNA sequence of SEQ ID NO: 16 in the Sequence Listing, encoding the amino acid sequence shown in SEQ ID NO: 14 in the Sequence Listing.

SEQ ID NO: 13 in the Sequence Listing consists of 141 amino acid residues. SEQ ID NO: 14 in the Sequence Listing consists of 130 amino acid residues. SEQ ID NO: 15 in the Sequence Listing consists of 423 bases, encoding a protein having the amino acid sequence of SEQ ID NO: 13 in the Sequence Listing. SEQ ID NO: 16 in the Sequence Listing consists of 390 bases, encoding a protein having the amino acid sequence of SEQ ID NO: 14 in the Sequence Listing.

It will be appreciated that those skilled in the art can obtain the expression vector of monoclonal antibody 5E08 by conventional molecular cloning using the heavy chain variable region and the light chain variable region amino acid sequence or DNA sequence of the monoclonal antibody 5E08 described above, and can obtain a monoclonal antibody having an activity of inhibiting tumor progression more easily by using conventional method of proteins expression. The monoclonal antibody having an activity of inhibiting tumor progression prepared by this method belongs to the disclosure of the present example.

Example 23

Adhesion Assay to Detect the Activity of Monoclonal Antibody 5E08 Blocking the Interaction of LSECtin Protein with Membrane form BTN3A3

During the adhesion assay, the purified monoclonal antibody 5E08 and LSECtin protein were mixed at a. ratio of 1:1 according to the amount of the substance, and the BT474 cell line BT474-BTN3A3 expressing BTN3A3 was incubated, and then the adhesion test was performed. The specific steps of the adhesion assay refered to the method described in the literature "Tang L, Yang J, Tang X, et al. The DC-SIGN family member LSECtin is a novel ligand of CD44 on activated T cells [J]. European journal of immunology, 2010, 40(4): 1185-1191". The experimental control protein was human IgG.

The adhesion assay results of monoclonal antibody 5E08 blocking the interaction between LSECtin protein and membrane form BTN3A3 were shown in FIG. 24. The calculation method of LSECtin adhesion rate was LSECtin adhesion positive cells and ZSG positive cells/ZSG positive cells. When the control human IgG was added, the adhesion rate of LSECtin to cells overexpressing BTN3A3 was 16.1%, and the calculation formula was 9.72/(9.72+50.6). However, when the monoclonal antibody 5E08 was added, the adhesion rate of LSECtin to cells overexpressing BTN3A3 was 1.4%, the calculation formula was 0.828/(0.828±58.8).

The results showed that monoclonal antibody 5E08 was able to block the interaction between LSECtin and BTN3A3.

Example 24

Detection of Monoclonal Antibody 5E08 Blocking LSECtin to Promote Tumor Cell Sternness B27 (purchased from Lite), bfGF (purchased from Sigma), EGF (purchased from Sigma), insulin (purchased from Sigma). heparin (purchased from Sigma), and DMEM/F12 serum-free medium were mixed to obtain a culture system, and the concentration of each component in the culture system was: B27 (10 ng/mL), bFGF (20 ng/mL), EGF (20 ng/mL), insulin (5 μg/mL), and heparin (4 μg/mL).

The breast cancer cells MDA-MB-231 (derived from the National Experimental Cell Resource Sharing Platform) were prepared into single cell suspensions and plated at 20,000/mL. After adding 100 ng of LSECtin, 0 μg/mL, 12.5 μg/mL, 25 μg/mL, 50 μg/mL, 100 μg/mL, of monoclonal antibody 5E08 was added, respectively, and human IgG was used as control. After 7-10 days of culture, calculate the number of spheres larger than 75 μm in diameter and take pictures.

The results were shown in FIG. 25. At the stimulation concentration, LSECtin was able to promote the sphere-formation of MDA-MB-231 cells, but it wasn't able to promote the sphere-formation of MDA-MB-231 cells with the addition of 50 μg/mL, and 100 μg/mL monoclonal antibody 5E08.

The results showed that monoclonal antibody 5E08 was able to blocking LSECtin to promote tumor cell sternness.

Example 25

Detection of Monoclonal Antibody 5E08 Inhibiting Tumor Progression

I. Inhibition Effect of Monoclonal Antibody 5E08 on Tumor Progression by Mouse Prevention Model 10000 human breast cancer cells MDA-MB-231. Matrigel (BD, 354230) and PBS (Hyclone, SH30256.01) were mixed to obtain a mixture. The mixture was separately planted into the lower mammary gland of 5-week-old female nude mice to establish human breast cancer xenografts in nude mice. Observed once every other week for two months, the long diameter a and the short diameter b of the mouse tumor were measured using vernier calipers, and the tumor volume and tumor formation rate were calculated. The calculation formula of tumor volume was 0.5×ab². The calculation formula of tumor formation rate was the number of tumor formation/total number of models.

One day before the establishment of model by planting cells in nude mice, the nude mice were divided into the following groups according to the different injections:

IgG control group: intraperitoneal injection of human IgG (50 µg/mouse)

5E08 group: intraperitoneal injection of monoclonal antibody 5E08 (50 µg/mouse)

MDA-MB-231 cells were planted separately into each mouse of the above group. After modeling, the protein was injected intraperitoneally every 3 days, and the inhibitory effect of monoclonal antibody 5E08 on tumor progression was observed by measuring the tumor volume.

The tumor volumes at 1, 2, 3, 4, 5, 6, and 7 weeks after modeling were as follows:

The IgG group was 0.00±0.00, 0.00±0.00, 0.00±0.00, 0.00±0.00, 20.67±18.82, 64.98±34.16, 124.03±47.41, 350.71±165.45 and 848.36±243.67 (mm³), respectively;

The 5E08 group was 0.00±0.00, 0.00±0.00, 0.00±0.00, 0.00±0.00, 4.38±12.37, 24.49±24.97, 35.57±37.09, 110.98±86.41 and 325.89±233.46 (mm³), respectively.

As shown in FIG. 26. the tumor volume of the injected monoclonal antibody 5E08 group was significantly smaller than that of the injected IgG group.

The detection results indicated that the monoclonal antibody 5E08 was able to inhibit tumor growth and could be used for the preparation of antitumor drugs and treatment of tumors.

II. Inhibition Effect of Monoclonal Antibody 5E08 on Tumor Progression by the Mouse Treatment Model When the mice planted MBA-MB-231 cells were modeled for 1 month, they were divided into IgG control group, ie intratumoral injection of human IgG (50 µg/mouse) and 5E08 group, ie intratumoral injection of monoclonal antibody 5E08 (50 µg/only) according to the equal mean tumor volume. The inhibition effect of monoclonal antibody 5E08 on tumor progression was observed by measuring tumor volume.

The tumor volume after treatment was as follows:

The IgG group was 197.40±47.98, 270.52±28.76, 389.69±17.26, 571.45±59.02, 933.05±158.71 and 1202.53±60.31 (mm³), respectively;

The 5E08 group was 179.87±42.91, 269.22±54.97, 276.68±58.52, 331.02±94.42, 443.16±48.3 and 492.66±71.39 (mm³), respectively.

The detection results were shown in FIG. 27, the tumor volume of the injected monoclonal antibody 5E08 group was significantly smaller than that of the injected IgG group. The detection results indicated that the monoclonal antibody 5E08 was able to inhibit tumor growth and could be used for the preparation of antitumor drugs and treatment of tumors.

Example 26

Monoclonal Antibody 5E08 Inhibits Tumors without Toxic Side Effects

I. Monoclonal Antibody 5E08 Inhibits Tumor without Toxic Side Effects in Mouse Prevention Model The prevention model in Example 25 was used for this example. After treatment with the experimental drug IgG or 5E08, the heart, liver, spleen, lung and kidney tissues of the mice were placed in formalin solution and sent to Beijing Jiasi Jiayang for tissue embedding, sectioning, and HE staining.

After the experimental drug action, the tissue sections were as shown in FIG. 28. After intraperitoneal injection of IgG or monoclonal antibody 5E08, the heart, liver, spleen, lung and kidney tissues of the mice were not damaged, and no obvious inflammatory cell infiltration occurred, indicating that the intraperitoneal injection of the monoclonal antibody 5E08 had no toxic side effects.

II. Monoclonal Antibody 5E08 Inhibits Tumor without Toxic Side Effects in Mouse Treatment Model The treatment model in Example 25 was used for this example. After treatment with the experimental drug IgG or 5E08, the heart, liver, spleen, lung and kidney tissues of the mice were placed in formalin solution and sent to Beijing Jiasi Jiayang for tissue embedding, sectioning, and HE staining.

After the experimental drug action, the tissue sections were as shown in FIG. 29, After intraperitoneal injection of IgG or monoclonal antibody 5E08, the heart, liver, spleen, lung and kidney tissues of the mice were not damaged, and no obvious inflammatory cell infiltration occurred, indicating that the intraperitoneal injection of the monoclonal antibody 5E08 had no toxic side effects,

INDUSTRIAL APPLICATION

The present invention provides an use of LSECtin expressed by infiltrating tumor-associated macrophage and BTN3A3 expressed by tumor solely or in combination as a target in tumor immunotherapy, and further provides a substance capable of inhibiting the activity of LSECtin expressed by infiltrating tumor-associated macrophage, the activity of BTN3A3 expressed by tumor, or the interaction of the LSECtin with BTN3A3, including RNA molecule, fusion protein BTN3A3-Ig, and monoclonal antibody 5E08, which can be used as an active ingredient to prepare a tumor immunotherapy drug, and is suitable for industrial applications.

The invention claimed is:

1. A method for cancer immunotherapy, wherein the method comprises administering an effective amount of a recombinant protein named BTN3A3-Ig to a cancer patient to block the interaction between LSECtin and BTN3A3, wherein the amino acid sequence of the BTN3A3-Ig is set forth in SEQ ID NO: 9; and wherein the cancer is a cancer in which tumor-associated macrophages express LSECtin and tumor cells express BTN3A3.

2. The method according to claim 1, wherein the cancer is selected from the group consisting of breast cancer, myeloma, liver cancer, gastric cancer, colorectal cancer, lung cancer, giant-cell tumor, renal cancer, throat cancer and parotid gland cancer.

* * * * *

SEQUENCE LISTING

```
<160> NUMBER OF SEQ ID NOS: 27

<210> SEQ ID NO 1
<211> LENGTH: 293
<212> TYPE: PRT
<213> ORGANISM: Artificial Sequence
<220> FEATURE:
<223> OTHER INFORMATION: LSECtin protein

<400> SEQUENCE: 1
```

```
Met Asp Thr Thr Arg Tyr Ser Lys Trp Gly Ser Ser Glu Glu Val
1               5                   10                  15

Pro Gly Gly Pro Trp Gly Arg Trp Val His Trp Ser Arg Pro Leu
            20                  25                  30

Phe Leu Ala Leu Ala Val Leu Val Thr Thr Val Leu Trp Ala Val Ile
        35                  40                  45

Leu Ser Ile Leu Leu Ser Lys Ala Ser Thr Glu Arg Ala Ala Leu Leu
50                  55                  60

Asp Gly His Asp Leu Arg Thr Asn Ala Ser Lys Gln Thr Ala Ala
65              70                  75                  80

Leu Gly Ala Leu Lys Glu Glu Val Gly Asp Cys His Ser Cys Cys Ser
            85                  90                  95

Gly Thr Gln Ala Gln Leu Gln Thr Thr Arg Ala Glu Leu Gly Glu Ala
            100                 105                 110

Gln Ala Lys Leu Met Glu Gln Glu Ser Ala Leu Arg Glu Leu Arg Glu
            115                 120                 125

Arg Val Thr Gln Gly Leu Ala Glu Ala Gly Arg Gly Arg Glu Asp Val
            130                 135                 140

Arg Thr Glu Leu Phe Arg Ala Leu Glu Ala Val Arg Leu Gln Asn Asn
145                 150                 155                 160

Ser Cys Glu Pro Cys Pro Thr Ser Trp Leu Ser Phe Glu Gly Ser Cys
            165                 170                 175

Tyr Phe Phe Ser Val Pro Lys Thr Thr Trp Ala Ala Ala Gln Asp His
            180                 185                 190

Cys Ala Asp Ala Ser Ala His Leu Val Ile Val Gly Gly Leu Asp Glu
            195                 200                 205

Gln Gly Phe Leu Thr Arg Asn Thr Arg Gly Arg Gly Tyr Trp Leu Gly
            210                 215                 220

Leu Arg Ala Val Arg His Leu Gly Lys Val Gln Gly Tyr Gln Trp Val
225                 230                 235                 240

Asp Gly Val Ser Leu Ser Phe Ser His Trp Asn Gln Gly Glu Pro Asn
            245                 250                 255

Asp Ala Trp Gly Arg Glu Asn Cys Val Met Met Leu His Thr Gly Leu
            260                 265                 270

Trp Asn Asp Ala Pro Cys Asp Ser Glu Lys Asp Gly Trp Ile Cys Glu
            275                 280                 285

Lys Arg His Asn Cys
            290

<210> SEQ ID NO 2
<211> LENGTH: 334
<212> TYPE: PRT
<213> ORGANISM: Artificial Sequence
<220> FEATURE:
<223> OTHER INFORMATION: BTN3A2 protein

<400> SEQUENCE: 2

Met Lys Met Ala Ser Ser Leu Ala Phe Leu Leu Leu Asn Phe His Val
1               5                   10                  15

Ser Leu Leu Leu Val Gln Leu Leu Thr Pro Cys Ser Ala Gln Phe Ser
            20                  25                  30

Val Leu Gly Pro Ser Gly Pro Ile Leu Ala Met Val Gly Glu Asp Ala
            35                  40                  45

Asp Leu Pro Cys His Leu Phe Pro Thr Met Ser Ala Glu Thr Met Glu
50                  55                  60
```

```
Leu Lys Trp Val Ser Ser Ser Leu Arg Gln Val Val Asn Val Tyr Ala
 65                  70                  75                  80

Asp Gly Lys Glu Val Glu Asp Arg Gln Ser Ala Pro Tyr Arg Gly Arg
                 85                  90                  95

Thr Ser Ile Leu Arg Asp Gly Ile Thr Ala Gly Lys Ala Ala Leu Arg
            100                 105                 110

Ile His Asn Val Thr Ala Ser Asp Ser Gly Lys Tyr Leu Cys Tyr Phe
        115                 120                 125

Gln Asp Gly Asp Phe Tyr Glu Lys Ala Leu Val Glu Leu Lys Val Ala
    130                 135                 140

Ala Leu Gly Ser Asn Leu His Val Glu Val Lys Gly Tyr Glu Asp Gly
145                 150                 155                 160

Gly Ile His Leu Glu Cys Arg Ser Thr Gly Trp Tyr Pro Gln Pro Gln
                165                 170                 175

Ile Gln Trp Ser Asn Ala Lys Gly Glu Asn Ile Pro Ala Val Glu Ala
            180                 185                 190

Pro Val Val Ala Asp Gly Val Gly Leu Tyr Glu Val Ala Ala Ser Val
        195                 200                 205

Ile Met Arg Gly Gly Ser Gly Glu Gly Val Ser Cys Ile Ile Arg Asn
    210                 215                 220

Ser Leu Leu Gly Leu Glu Lys Thr Ala Ser Ile Ser Ile Ala Asp Pro
225                 230                 235                 240

Phe Phe Arg Ser Ala Gln Pro Trp Ile Ala Ala Leu Ala Gly Thr Leu
                245                 250                 255

Pro Ile Leu Leu Leu Leu Leu Ala Gly Ala Ser Tyr Phe Leu Trp Arg
            260                 265                 270

Gln Gln Lys Glu Ile Thr Ala Leu Ser Ser Glu Ile Glu Ser Glu Gln
        275                 280                 285

Glu Met Lys Glu Met Gly Tyr Ala Ala Thr Glu Arg Glu Ile Ser Leu
    290                 295                 300

Arg Glu Ser Leu Gln Glu Leu Lys Arg Lys Ile Gln Tyr Leu
305                 310                 315                 320

Thr Arg Gly Glu Glu Ser Ser Ser Asp Thr Asn Lys Ser Ala
                325                 330
```

<210> SEQ ID NO 3
<211> LENGTH: 584
<212> TYPE: PRT
<213> ORGANISM: Artificial Sequence
<220> FEATURE:
<223> OTHER INFORMATION: BTN3A3 protein

<400> SEQUENCE: 3

```
Met Lys Met Ala Ser Ser Leu Ala Phe Leu Leu Leu Asn Phe His Val
  1               5                  10                  15

Ser Leu Phe Leu Val Gln Leu Leu Thr Pro Cys Ser Ala Gln Phe Ser
                 20                  25                  30

Val Leu Gly Pro Ser Gly Pro Ile Leu Ala Met Val Gly Glu Asp Ala
             35                  40                  45

Asp Leu Pro Cys His Leu Phe Pro Thr Met Ser Ala Glu Thr Met Glu
         50                  55                  60

Leu Arg Trp Val Ser Ser Ser Leu Arg Gln Val Val Asn Val Tyr Ala
 65                  70                  75                  80

Asp Gly Lys Glu Val Glu Asp Arg Gln Ser Ala Pro Tyr Arg Gly Arg
                 85                  90                  95
```

-continued

```
Thr Ser Ile Leu Arg Asp Gly Ile Thr Ala Gly Lys Ala Ala Leu Arg
                100                 105                 110

Ile His Asn Val Thr Ala Ser Asp Ser Gly Lys Tyr Leu Cys Tyr Phe
            115                 120                 125

Gln Asp Gly Asp Phe Tyr Glu Lys Ala Leu Val Glu Leu Lys Val Ala
        130                 135                 140

Ala Leu Gly Ser Asp Leu His Ile Glu Val Lys Gly Tyr Glu Asp Gly
145                 150                 155                 160

Gly Ile His Leu Glu Cys Arg Ser Thr Gly Trp Tyr Pro Gln Pro Gln
                165                 170                 175

Ile Lys Trp Ser Asp Thr Lys Gly Glu Asn Ile Pro Ala Val Glu Ala
            180                 185                 190

Pro Val Val Ala Asp Gly Val Gly Leu Tyr Ala Val Ala Ala Ser Val
        195                 200                 205

Ile Met Arg Gly Ser Ser Gly Gly Val Ser Cys Ile Ile Arg Asn
210                 215                 220

Ser Leu Leu Gly Leu Glu Lys Thr Ala Ser Ile Ser Ile Ala Asp Pro
225                 230                 235                 240

Phe Phe Arg Ser Ala Gln Pro Trp Ile Ala Ala Leu Ala Gly Thr Leu
                245                 250                 255

Pro Ile Ser Leu Leu Leu Leu Ala Gly Ala Ser Tyr Phe Leu Trp Arg
            260                 265                 270

Gln Gln Lys Glu Lys Ile Ala Leu Ser Arg Glu Thr Glu Arg Glu Arg
        275                 280                 285

Glu Met Lys Glu Met Gly Tyr Ala Ala Thr Glu Gln Glu Ile Ser Leu
290                 295                 300

Arg Glu Lys Leu Gln Glu Leu Lys Trp Arg Lys Ile Gln Tyr Met
305                 310                 315                 320

Ala Arg Gly Glu Lys Ser Leu Ala Tyr His Glu Trp Lys Met Ala Leu
                325                 330                 335

Phe Lys Pro Ala Asp Val Ile Leu Asp Pro Thr Ala Asn Ala Ile
            340                 345                 350

Leu Leu Val Ser Glu Asp Gln Arg Ser Val Gln Arg Ala Glu Glu Pro
        355                 360                 365

Arg Asp Leu Pro Asp Asn Pro Glu Arg Phe Glu Trp Arg Tyr Cys Val
370                 375                 380

Leu Gly Cys Glu Asn Phe Thr Ser Gly Arg His Tyr Trp Glu Val Glu
385                 390                 395                 400

Val Gly Asp Arg Lys Glu Trp His Ile Gly Val Cys Ser Lys Asn Val
                405                 410                 415

Glu Arg Lys Lys Gly Trp Val Lys Met Thr Pro Glu Asn Gly Tyr Trp
            420                 425                 430

Thr Met Gly Leu Thr Asp Gly Asn Lys Tyr Arg Ala Leu Thr Glu Pro
        435                 440                 445

Arg Thr Asn Leu Lys Leu Pro Glu Pro Pro Arg Lys Val Gly Ile Phe
450                 455                 460

Leu Asp Tyr Glu Thr Gly Glu Ile Ser Phe Tyr Asn Ala Thr Asp Gly
465                 470                 475                 480

Ser His Ile Tyr Thr Phe Pro His Ala Ser Phe Ser Glu Pro Leu Tyr
                485                 490                 495

Pro Val Phe Arg Ile Leu Thr Leu Glu Pro Thr Ala Leu Thr Ile Cys
            500                 505                 510

Pro Ile Pro Lys Glu Val Glu Ser Ser Pro Asp Pro Asp Leu Val Pro
```

```
        515                 520                 525
Asp His Ser Leu Glu Thr Pro Leu Thr Pro Gly Leu Ala Asn Glu Ser
            530                 535                 540

Gly Glu Pro Gln Ala Glu Val Thr Ser Leu Leu Pro Ala His Pro
545                 550                 555                 560

Gly Ala Glu Val Ser Pro Ser Ala Thr Thr Asn Gln Asn His Lys Leu
                565                 570                 575

Gln Ala Arg Thr Glu Ala Leu Tyr
            580

<210> SEQ ID NO 4
<211> LENGTH: 21
<212> TYPE: DNA
<213> ORGANISM: Artificial Sequence
<220> FEATURE:
<223> OTHER INFORMATION: shRNA molecule interfering expression of BTN3A3

<400> SEQUENCE: 4
gccacagatg gatctcatat c                                           21

<210> SEQ ID NO 5
<211> LENGTH: 21
<212> TYPE: DNA
<213> ORGANISM: Artificial Sequence
<220> FEATURE:
<223> OTHER INFORMATION: shRNA molecule interfering expression of BTN3A3

<400> SEQUENCE: 5
cccttctgca acaaccaatc a                                           21

<210> SEQ ID NO 6
<211> LENGTH: 1542
<212> TYPE: DNA
<213> ORGANISM: Artificial Sequence
<220> FEATURE:
<223> OTHER INFORMATION: BTN3A1 gene

<400> SEQUENCE: 6
atgaaaatgg caagtttcct ggccttcctt ctgctcaact ttcgtgtctg cctcctttg     60 cttcagctgc tcatgcctca ctcagctcag ttttctgtgc ttggaccctc tgggcccatc   120
ctggccatgt gggtgaaga cgctgatctg ccctgtcacc tgttcccgac catgagtgca   180
gagaccatgg agctgaagtg ggtgagttcc agcctaaggc aggtggtgaa cgtgtatgca   240
gatggaaagg aagtggaaga caggcagagt gcaccgtatc gagggagaac ttcgattctg   300
cgggatggca tcactgcagg gaaggctgct ctccgaatac acaacgtcac agcctctgac   360
agtggaaagt acttgtgtta tttccaagat ggtgacttct atgaaaaagc cctggtggag   420
ctgaaggttg cagcactggg ttctgatctt cacgttgatg tgaagggtta caaggatgga   480
gggatccatc tggagtgcag gtccactggc tggtaccccc aaccccaaat acagtggagc   540
aacaacaagg gagagaacat cccgactgtg gaagcacctg tggttgcaga cggagtgggc   600
ctgtatgcag tagcagcatc tgtgatcatg agaggcagct ctgggggaggg tgtatcctgt   660 accatcagaa gttccctcct cggcctggaa aagacagcca gcatttccat cgcagacccc   720
ttcttcagga gcgcccagag gtggatcgcc gccctggcag ggaccctgcc tgtcttgctg   780
ctgcttcttg ggggagccgg ttacttcctg tggcaacagc aggaggaaaa aaagactcag   840
ttcagaaaga aaagagaga gcaagagttg agaaaatgg catggagcac aatgaagcaa   900
gaacaaagca aagagtgaa gctcctggag gaactcagat ggagaagtat ccagtatgca   960
```

```
tctcggggag agagacattc agcctataat gaatggaaaa aggccctctt caagcctgcg    1020
gatgtgattc tggatccaaa acagcaaac cccatcctcc ttgtttctga ggaccagagg    1080
agtgtgcagc gtgccaagga gccccaggat ctgccagaca accctgagag atttaattgg    1140
cattattgtg ttctcggctg tgagagcttc atatcaggga cattactg ggaggtggag    1200 gtaggggaca ggaaagagtg gcatataggg gtgtgcagta agaatgtgca gagaaaaggc    1260
tgggtcaaaa tgcacctga gaatggattc tggactatgg ggctgactga tgggaataag    1320
tatcggactc taactgagcc cagaaccaac ctgaaacttc ctaagccccc taagaaagtg    1380
ggggtcttcc tggactatga gactggagat atctcattct acaatgctgt ggatggatcg    1440
catattcata ctttcctgga cgtctccttc tctgaggctc tatatcctgt tttcagaatt    1500
ttgaccttgg agcccacggc cctgactatt tgtccagcgt ga                      1542

<210> SEQ ID NO 7
<211> LENGTH: 1005
<212> TYPE: DNA
<213> ORGANISM: Artificial Sequence
<220> FEATURE:
<223> OTHER INFORMATION: BTN3A2 gene

<400> SEQUENCE: 7
atgaaaatgg caagttccct ggctttcctt ctgctcaact ttcatgtctc cctcctcttg     60
gtccagctgc tcactccttg ctcagctcag ttttctgtgc ttggaccctc tgggcccatc   120
ctggccatgg tgggtgaaga cgctgatctg ccctgtcacc tgttcccgac catgagtgca   180
gagaccatgg agctgaagtg ggtaagttcc agcctaaggc aggtggtgaa cgtgtatgca   240
gatggaaagg aagtggaaga caggcagagt gcaccgtatc gagggagaac ttcgattctg   300
cgggatggca tcactgcagg gaaggctgct ctccgaatac acaacgtcac agcctctgac   360
agtgaaaagt acttgtgtta tttccaagat ggtgacttct atgaaaaagc cctggtggag   420
ctgaaggttg cagcactggg ttctaatctt cacgtcgaag tgaagggtta tgaggatgga   480
gggatccatc tggagtgcag gtccaccggc tggtaccccc aaccccaaat acagtggagc   540
aacgccaagg gagagaacat cccagctgtg gaagcacctg tggttgcaga tggagtgggc   600
ctatatgaag tagcagcatc tgtgatcatg agaggcggct ccggggaggg tgtatcctgc   660
atcatcagaa attccctcct cggcctggaa agacagccaa gcatttccat cgcagacccc   720
ttcttcagga gcgcccagcc ctggatcgca gccctggcag ggaccctgcc tatcttgctg   780
ctgcttctcg ccggagccag ttacttcttg tggagacaac agaaggaaat aactgctctg   840
tccagtgaga tagaaagtga gcaagagatg aaagaaatgg gatatgctgc aacagagcgg   900
gaaataagcc taagagagag cctccaggag gaactcaaga ggaaaaaaat ccagtacttg   960
actcgtggag aggagtcttc gtccgatacc aataagtcag cctga                 1005

<210> SEQ ID NO 8
<211> LENGTH: 1755
<212> TYPE: DNA
<213> ORGANISM: Artificial Sequence
<220> FEATURE:
<223> OTHER INFORMATION: BTN3A3 gene

<400> SEQUENCE: 8
atgaaaatgg caagttccct ggctttcctt ctgctcaact ttcatgtctc cctcttcttg     60
gtccagctgc tcactccttg ctcagctcag ttttctgtgc ttggaccctc tgggcccatc   120
```

-continued

| | |
|---|---|
| ctggccatgg tgggtgaaga cgctgatctg ccctgtcacc tgttcccgac catgagtgca | 180 |
| gagaccatgg agctgaggtg ggtgagttcc agcctaaggc aggtggtgaa cgtgtatgca | 240 |
| gatggaaagg aagtggaaga caggcagagt gcaccgtatc gagggagaac ttcgattctg | 300 |
| cgggatggca tcactgcagg gaaggctgct ctccgaatac acaacgtcac agcctctgac | 360 |
| agtggaaagt acttgtgtta tttccaagat ggtgacttct acgaaaaagc cctggtggag | 420 |
| ctgaaggttg cagcattggg ttctgatctt cacattgaag tgaagggtta tgaggatgga | 480 |
| gggatccatc tggagtgcag gtccactggc tggtaccccc aaccccaaat aaagtggagc | 540 |
| gacaccaagg agagaacat cccggctgtg aagcacctg tggttgcaga tggagtgggc | 600 |
| ctgtatgcag tagcagcatc tgtgatcatg agaggcagct ctggtggggg tgtatcctgc | 660 |
| atcatcagaa attccctcct cggcctggaa aagacagcca gcatatccat cgcagacccc | 720 |
| ttcttcagga gcgcccagcc ctggatcgcg gccctggcag ggaccctgcc tatctcgttg | 780 |
| ctgcttctcg caggagccag ttacttcttg tggagacaac agaaggaaaa aattgctctg | 840 |
| tccagggaga cagaaagaga gcgagagatg aaagaaatgg gatacgctgc aacagagcaa | 900 |
| gaaataagcc taagagagaa gctccaggag gaactcaagt ggaggaaaat ccagtacatg | 960 |
| gctcgtggag agaagtcttt ggcctatcat gaatggaaaa tggccctctt caaacctgcg | 1020 |
| gatgtgattc tggatccaga cacggcaaac gccatcctcc ttgtttctga ggaccagagg | 1080 |
| agtgtgcagc gtgctgaaga gccgcgggat ctgccagaca accctgagag atttgaatgg | 1140 |
| cgttactgtg tccttggctg tgaaaacttc acatcaggga gacattactg ggaggtggaa | 1200 |
| gtggggggaca gaaagagtg gcatattggg gtatgtagta agaacgtgga gaggaaaaaa | 1260 |
| ggttgggtca aaatgacacc ggagaacgga tactggacta tgggcctgac tgatgggaat | 1320 |
| aagtatcggg ctctcactga gcccagaacc aacctgaaac ttcctgagcc tctaggaaa | 1380 |
| gtggggatct tcctggacta tgagactgga gagatctcgt tctataatgc cacagatgga | 1440 |
| tctcatatct acacctttcc gcacgcctct ttctctgagc tctatatcc tgttttcaga | 1500 |
| attttgacct ggagcccac tgccctgacc atttgcccaa taccaaaaga gtagagagt | 1560 |
| tcccccgatc ctgacctagt gcctgatcat tccctggaga caccactgac cccgggctta | 1620 |
| gctaatgaaa gtggggagcc tcaggctgaa gtaacatctc tgcttctccc tgcccaccct | 1680 |
| ggagctgagg tctccccttc tgcaacaacc aatcagaacc ataagctaca ggcacgcact | 1740 |
| gaagcacttt actga | 1755 |

<210> SEQ ID NO 9
<211> LENGTH: 490
<212> TYPE: PRT
<213> ORGANISM: Artificial Sequence
<220> FEATURE:
<223> OTHER INFORMATION: fusion protein BTN3A3-Ig

<400> SEQUENCE: 9

Met Ser Ala Leu Leu Ile Leu Ala Leu Val Gly Ala Ala Val Ala Lys
1               5                   10                  15

Met Ala Ser Ser Leu Ala Phe Leu Leu Leu Asn Phe His Val Ser Leu
                20                  25                  30

Phe Leu Val Gln Leu Leu Thr Pro Cys Ser Ala Gln Phe Ser Val Leu
            35                  40                  45

Gly Pro Ser Gly Pro Ile Leu Ala Met Val Gly Glu Asp Ala Asp Leu
        50                  55                  60

Pro Cys His Leu Phe Pro Thr Met Ser Ala Glu Thr Met Glu Leu Arg

```
                65                  70                  75                  80
Trp Val Ser Ser Ser Leu Arg Gln Val Val Asn Val Tyr Ala Asp Gly
                    85                  90                  95

Lys Glu Val Glu Asp Arg Gln Ser Ala Pro Tyr Arg Gly Arg Thr Ser
                100                 105                 110

Ile Leu Arg Asp Gly Ile Thr Ala Gly Lys Ala Ala Leu Arg Ile His
                115                 120                 125

Asn Val Thr Ala Ser Asp Ser Gly Lys Tyr Leu Cys Tyr Phe Gln Asp
130                 135                 140

Gly Asp Phe Tyr Glu Lys Ala Leu Val Glu Leu Lys Val Ala Ala Leu
145                 150                 155                 160

Gly Ser Asp Leu His Ile Glu Val Lys Gly Tyr Glu Asp Gly Gly Ile
                165                 170                 175

His Leu Glu Cys Arg Ser Thr Gly Trp Tyr Pro Gln Pro Gln Ile Lys
                180                 185                 190

Trp Ser Asp Thr Lys Gly Glu Asn Ile Pro Ala Val Glu Ala Pro Val
                195                 200                 205

Val Ala Asp Gly Val Gly Leu Tyr Ala Val Ala Ser Val Ile Met
210                 215                 220

Arg Gly Ser Ser Gly Gly Val Ser Cys Ile Ile Arg Asn Ser Leu
225                 230                 235                 240

Leu Gly Leu Glu Lys Thr Ala Ser Ile Ser Ile Ala Asp Pro Phe Phe
                245                 250                 255

Arg Ser Ala Gln Pro Trp Ser Arg Leu Glu Thr Cys Pro Pro Cys Pro
                260                 265                 270

Ala Pro Glu Leu Leu Gly Gly Pro Ser Val Phe Leu Phe Pro Pro Lys
                275                 280                 285

Pro Lys Asp Thr Leu Met Ile Ser Arg Thr Pro Glu Val Thr Cys Val
                290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
                340                 345                 350

Gln Asp Trp Leu Asn Gly Lys Glu Tyr Lys Cys Lys Val Ser Asn Lys
                355                 360                 365

Ala Leu Pro Ala Pro Ile Glu Lys Thr Ile Ser Lys Ala Lys Gly Gln
                370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
                420                 425                 430

Tyr Lys Thr Thr Pro Pro Val Leu Asp Ser Asp Gly Ser Phe Phe Leu
                435                 440                 445

Tyr Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys Glx
                485                 490
```

<210> SEQ ID NO 10
<211> LENGTH: 1470
<212> TYPE: DNA
<213> ORGANISM: Artificial Sequence
<220> FEATURE:
<223> OTHER INFORMATION: fusion gene BTN3A3-Ig

<400> SEQUENCE: 10

```
atgtctgctc tgctgatcct ggcgctggtg ggcgccgcgg tggctaaaat ggcaagttcc      60
ctggctttcc ttctgctcaa ctttcatgtc tccctcttct tggtccagct gctcactcct     120
tgctcagctc agttttctgt gcttggaccc tctgggccca tcctggccat ggtgggtgaa     180
gacgctgatc tgccctgtca cctgttcccg accatgagtg cagagaccat ggagctgagg     240
tgggtgagtt ccagcctaag gcaggtggtg aacgtgtatg cagatggaaa ggaagtggaa     300
gacaggcaga gtgcaccgta tcgagggaga acttcgattc tgcgggatgg catcactgca     360
gggaaggctg ctctccgaat acacaacgtc acagcctctg acagtggaaa gtacttgtgt     420
tatttccaag atggtgactt ctacgaaaaa gccctggtgg agctgaaggt tgcagcattg     480
ggttctgatc ttcacattga agtgaagggt tatgaggatg agggatcca tctggagtgc     540
aggtccactg gctggtaccc ccaaccccaa ataaagtgga gcgacaccaa gggagagaac     600
atcccggctc tggaagcacc tgtggttgca gatggagtgg gcctgtatgc agtagcagca     660
tctgtgatca tgagaggcag ctctggtggg ggtgtatcct gcatcatcag aaattccctc     720
ctcggcctgg aaaagacagc cagcatatcc atcgcagacc ccttcttcag gagcgcccag     780
ccctggtcaa gactcgagac atgcccaccg tgcccagcac ctgaactcct gggggaccg     840
tcagtcttcc tcttccccc aaaacccaag gacaccctca tgatctcccg gacccctgag     900
gtcacatgcg tggtggtgga cgtgagccac gaagaccctg aggtcaagtt caactggtac     960
gtggacggcg tggaggtgca taatgccaag acaaagccgc gggaggagca gtacaacagc    1020
acgtaccgtg tggtcagcgt cctcaccgtc ctgcaccagg actggctgaa tggcaaggag    1080
tacaagtgca aggtctccaa caaagccctc ccagccccca tcgagaaaac catctccaaa    1140
gccaaagggc agccccgaga accacaggtg tacaccctgc ccccatcccg ggatgagctg    1200
accaagaacc aggtcagcct gacctgcctg gtcaaaggct tctatcccag cgacatcgcc    1260
gtggagtggg agagcaatgg gcagccggag aacaactaca agaccacgcc tcccgtgctg    1320
gactccgacg gctccttctt cctctacagc aagctcaccg tggacaagag caggtggcag    1380
caggggaacg tcttctcatg ctccgtgatg catgaggctc tgcacaacca ctacacgcag    1440
aagagcctct ccctgtctcc gggtaaataa                                    1470
```

<210> SEQ ID NO 11
<211> LENGTH: 499
<212> TYPE: PRT
<213> ORGANISM: Artificial Sequence
<220> FEATURE:
<223> OTHER INFORMATION: fusion protein BTN3A3-mIg

<400> SEQUENCE: 11

Met Ser Ala Leu Leu Ile Leu Ala Leu Val Gly Ala Ala Val Ala Lys
1               5                   10                  15

Met Ala Ser Ser Leu Ala Phe Leu Leu Leu Asn Phe His Val Ser Leu
            20                  25                  30

Phe Leu Val Gln Leu Leu Thr Pro Cys Ser Ala Gln Phe Ser Val Leu
        35                  40                  45

-continued

Gly Pro Ser Gly Pro Ile Leu Ala Met Val Gly Glu Asp Ala Asp Leu
            50                  55                  60

Pro Cys His Leu Phe Pro Thr Met Ser Ala Glu Thr Met Glu Leu Arg
65                  70                  75                  80

Trp Val Ser Ser Ser Leu Arg Gln Val Val Asn Val Tyr Ala Asp Gly
                    85                  90                  95

Lys Glu Val Glu Asp Arg Gln Ser Ala Pro Tyr Arg Gly Arg Thr Ser
                100                 105                 110

Ile Leu Arg Asp Gly Ile Thr Ala Gly Lys Ala Ala Leu Arg Ile His
            115                 120                 125

Asn Val Thr Ala Ser Asp Ser Gly Lys Tyr Leu Cys Tyr Phe Gln Asp
            130                 135                 140

Gly Asp Phe Tyr Glu Lys Ala Leu Val Glu Leu Lys Val Ala Ala Leu
145                 150                 155                 160

Gly Ser Asp Leu His Ile Glu Val Lys Gly Tyr Glu Asp Gly Gly Ile
                165                 170                 175

His Leu Glu Cys Arg Ser Thr Gly Trp Tyr Pro Gln Pro Gln Ile Lys
            180                 185                 190

Trp Ser Asp Thr Lys Gly Glu Asn Ile Pro Ala Val Glu Ala Pro Val
            195                 200                 205

Val Ala Asp Gly Val Gly Leu Tyr Ala Val Ala Ser Val Ile Met
210                 215                 220

Arg Gly Ser Ser Gly Gly Val Ser Cys Ile Ile Arg Asn Ser Leu
225                 230                 235                 240

Leu Gly Leu Glu Lys Thr Ala Ser Ile Ser Ile Ala Asp Pro Phe Phe
            245                 250                 255

Arg Ser Ala Gln Pro Trp Ser Arg Leu Glu Pro Arg Gly Pro Thr Ile
            260                 265                 270

Lys Pro Cys Pro Pro Cys Lys Cys Pro Ala Pro Asn Leu Leu Gly Gly
            275                 280                 285

Pro Ser Val Phe Ile Phe Pro Pro Lys Ile Lys Asp Val Leu Met Ile
290                 295                 300

Ser Leu Ser Pro Ile Val Thr Cys Val Val Val Asp Val Ser Glu Asp
305                 310                 315                 320

Asp Pro Asp Val Gln Ile Ser Trp Phe Val Asn Asn Val Glu Val His
            325                 330                 335

Thr Ala Gln Thr Gln Thr His Arg Glu Asp Tyr Asn Ser Thr Leu Arg
            340                 345                 350

Val Val Ser Ala Leu Pro Ile Gln His Gln Asp Trp Met Ser Gly Lys
            355                 360                 365

Glu Phe Lys Cys Lys Val Asn Asn Lys Asp Leu Pro Ala Pro Ile Glu
            370                 375                 380

Arg Thr Ile Ser Lys Pro Lys Gly Ser Val Arg Ala Pro Gln Val Tyr
385                 390                 395                 400

Val Leu Pro Pro Pro Glu Glu Met Thr Lys Lys Gln Val Thr Leu
                405                 410                 415

Thr Cys Met Val Thr Asp Phe Met Pro Glu Asp Ile Tyr Val Glu Trp
            420                 425                 430

Thr Asn Asn Gly Lys Thr Glu Leu Asn Tyr Lys Asn Thr Glu Pro Val
            435                 440                 445

Leu Asp Ser Asp Gly Ser Tyr Phe Met Tyr Ser Lys Leu Arg Val Glu
            450                 455                 460

```
Lys Lys Asn Trp Val Glu Arg Asn Ser Tyr Ser Cys Ser Val Val His
465                 470                 475                 480

Glu Gly Leu His Asn His His Thr Thr Lys Ser Phe Ser Arg Thr Pro
                485                 490                 495

Gly Lys Glx

<210> SEQ ID NO 12
<211> LENGTH: 1497
<212> TYPE: DNA
<213> ORGANISM: Artificial Sequence
<220> FEATURE:
<223> OTHER INFORMATION: fusion gene BTN3A3-mIg

<400> SEQUENCE: 12
atgtctgctc tgctgatcct ggcgctggtg ggcgccgcgg tggctaagat ggcttcctcc      60
ctggcattcc tgctgctgaa ctttcacgtc tctctgtttc tggtccagct gctgactccc     120
tgctctgcac agttctccgt gctgggccct tctggcccaa tcctggcaat ggtgggagag     180
gacgcagatc tgccatgcca cctgtttccc accatgagcg ccgagacaat ggagctgcgg     240
tgggtgagct cctctctgag acaggtggtg aacgtgtacg ccgacggcaa ggaggtggag     300
gatcggcagt ctgccccctta tcggggcaga accagcatcc tgagggacgg aatcacagca     360
ggcaaggccg ccctgagaat ccacaatgtg accgcctctg atagcggcaa gtacctgtgc     420
tatttccagg acgcgacttt ctacgagaag gccctggtgg agctgaaggt ggccgccctg     480
ggatctgacc tgcacatcga ggtgaagggc tacgaggatg gcggcatcca cctggagtgt     540
cggagcaccg ctggtatcc tcagccacag atcaagtggt ccgacacaaa gggagagaac     600
atccctgcag tggaggcacc agtggtggca gatggagtgg gcctgtatgc agtggcagca     660
tccgtgatca tgaggggcag ctccggagga ggcgtgtcct gtatcatccg caattctctg     720
ctgggcctgg agaagaccgc ctccatctct atcgccgacc ccttctttag gagcgcccag     780
ccttggtcca ggctcgagcc agaggcccct acaatcaagc catgcccacc ttgcaagtgt     840
ccagcaccta acctgctggg aggacctagc gtgttcatct ttccacccaa gatcaaggac     900
gtgctgatga tcagcctgtc ccctatcgtg acctgcgtgg tggtggacgt gtccgaggac     960
gatccagatg tgcagatctc ttggttcgtg aacaatgtgg aggtgcacac cgcccagacc    1020
cagacacaca gggaggatta caatagcaca ctgagggtgg tgtccgccct gccaatccag    1080
caccaggact ggatgtccgg caaggagttt aagtgcaagg tgaacaataa ggatctgcca    1140
gcccccatcg agaggaccat ctctaagcca aagggaagcg tgcgcgcacc acaggtgtat    1200
gtgctgcctc cacccgagga ggagatgacc aagaagcagg tgaccctgac atgtatggtg    1260
acagacttca tgccagagga tatctacgtg gagtggacca acaatggcaa gacagagctg    1320
aactataaga tacagagcc cgtgctggac tctgatggca gctactttat gtatagcaag    1380
ctgcgggtgg agaagaagaa ctgggtggag agaaattctt acagctgctc cgtggtgcac    1440
gaaggactgc ataatcacca tacaaccaaa tcttttttcaa ggaccccctgg caaatga    1497

<210> SEQ ID NO 13
<211> LENGTH: 141
<212> TYPE: PRT
<213> ORGANISM: Artificial Sequence
<220> FEATURE:
<223> OTHER INFORMATION: heavy chain variable region of monoclonal
      antibody 5E08

<400> SEQUENCE: 13
```

Met Gly Trp Ile Trp Ile Phe Leu Phe Leu Ser Gly Thr Ala Gly
1               5                   10                  15

Val His Ser Glu Val Gln Leu Gln Gln Ser Gly Pro Glu Leu Val Lys
            20                  25                  30

Thr Gly Ala Ser Val Lys Ile Ser Cys Lys Ala Ser Gly Tyr Ser Phe
        35                  40                  45

Thr Gly Phe Tyr Met His Trp Val Lys Gln Ser His Gly Lys Ser Leu
    50                  55                  60

Glu Trp Ile Gly Tyr Val Ser Cys Tyr Asn Gly Ala Thr Ser Tyr Asn
65                  70                  75                  80

Gln Lys Phe Lys Gly Lys Ala Thr Phe Thr Val Asp Thr Ser Ser Ser
                85                  90                  95

Thr Ala Tyr Met Gln Phe Asn Ser Leu Thr Ser Glu Asp Ser Ala Val
            100                 105                 110

Tyr Tyr Cys Ala Arg Ala Gly Gly Tyr Asp Tyr Glu Gly Tyr Ala Leu
        115                 120                 125

Asp Tyr Trp Gly Gln Gly Thr Ser Val Thr Val Ser Ser
    130                 135                 140

<210> SEQ ID NO 14
<211> LENGTH: 130
<212> TYPE: PRT
<213> ORGANISM: Artificial Sequence
<220> FEATURE:
<223> OTHER INFORMATION: light chain variable region of monoclonal
      antibody 5E08

<400> SEQUENCE: 14

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Thr
            20                  25                  30

Met Ser Ala Ser Leu Gly Glu Arg Val Thr Met Thr Cys Thr Ala Ser
        35                  40                  45

Ser Ser Val Ser Ser Thr Tyr Leu His Trp Tyr Gln Gln Lys Pro Gly
    50                  55                  60

Ser Ser Pro Lys Leu Trp Ile Tyr Thr Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Leu Ser Ser Met Glu Ala Glu Asp Ala Ala Thr Tyr Tyr Cys His
            100                 105                 110

Gln Tyr His Arg Ser Pro Phe Thr Phe Gly Ser Gly Thr Lys Leu Glu
        115                 120                 125

Ile Lys
    130

<210> SEQ ID NO 15
<211> LENGTH: 423
<212> TYPE: DNA
<213> ORGANISM: Artificial Sequence
<220> FEATURE:
<223> OTHER INFORMATION: coding gene of heavy chain variable region of
      monoclonal antibody 5E08

<400> SEQUENCE: 15
atgggatgga tctggatctt tctcttcctc ctgtcaggaa ctgcaggtgt ccactctgag      60
gtccagctgc agcagtctgg acctgagcta gtgaagactg ggcttcagt gaagatatcc     120

```
tgcaaggctt ctggttactc attcactggt ttctacatgc actgggtcaa gcagagccat    180
ggaaagagcc ttgagtggat tggatatgtc agttgttaca atggtgctac tagctacaat    240
cagaagttca agggcaaggc cacatttact gtagacacat cctccagcac agcctacatg    300
cagttcaaca gcctgacatc tgaagactct gcggtctatt actgtgcaag agctggggga    360
tatgattacg aaggctatgc tctggactac tggggtcaag aacctcagt caccgtctcc    420 tca                                                                   423

<210> SEQ ID NO 16
<211> LENGTH: 390
<212> TYPE: DNA
<213> ORGANISM: Artificial Sequence
<220> FEATURE:
<223> OTHER INFORMATION: coding gene of light chain variable region of
      monoclonal antibody 5E08

<400> SEQUENCE: 16 atggatttc aggtgcagat tttcagcttc ctgctaatca gtgcctcagt cataatgtcc      60
agaggacaaa ttgttctcac ccagtctcca gcaaccatgt ctgcatctct aggggaacgg   120
gtcaccatga cctgcactgc agctcaagt gtaagttcca cttacttgca ctggtaccag   180
cagaagccag atcctcccc caaactctgg atctatacca catccaacct ggcttctgga    240
gtcccagctc gcttcagtgg cagtgggtct gggacctctt actctctcac actcagcagc   300
atggaggctg aagatgctgc cacttattac tgccaccagt atcatcgttc cccattcacg   360
ttcggctcgg gacaaagtt ggaaataaaa                                       390

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
ggtgcccatc tggtgattgt                                                  20

<210> SEQ ID NO 18
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 18
cagtggctga agttgagtga gg                                               22

<210> SEQ ID NO 19
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 19
aggtcggtgt gaacggattt g                                                21

<210> SEQ ID NO 20
<211> LENGTH: 23
<212> TYPE: DNA
<213> ORGANISM: Artificial Sequence
```

```
<220> FEATURE:
<223> OTHER INFORMATION: synthetic oligonucleotide

<400> SEQUENCE: 20
tgtagaccat gtagttgagg tca                                              23

<210> SEQ ID NO 21
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 21
ttctccgaac gtgtcacgtt tc                                               22

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
gctcgagaag gatgtggtcc                                                  20

<210> SEQ ID NO 23
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 23
gttgtgcata gtcgctgct                                                   19

<210> SEQ ID NO 24
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 24
tctggacact ggctgaatcc t                                                21

<210> SEQ ID NO 25
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 25
cgctgattag gctccaacca t                                                21

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
gctcgcagac ctacatgaac                                                  20
```

```
<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 27
gggaggaaga ggtaaccaca                                              20
```